US010385136B2

(12) United States Patent
Smith et al.

(10) Patent No.: US 10,385,136 B2
(45) Date of Patent: *Aug. 20, 2019

(54) USE OF SEMAPHORIN-4D BINDING MOLECULES FOR TREATING NEURODEGENERATIVE DISORDERS

(71) Applicant: Vaccinex, Inc., Rochester, NY (US)

(72) Inventors: Ernest S. Smith, W. Henrietta, NY (US); Maurice Zauderer, Pittsford, NY (US); William J. Bowers, Webster, NY (US); Alan Jonason, Pittsford, NY (US)

(73) Assignee: Vaccinex, Inc., Rochester, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/465,509

(22) Filed: Mar. 21, 2017

(65) Prior Publication Data

US 2017/0198053 A1 Jul. 13, 2017

Related U.S. Application Data

(63) Continuation of application No. 15/420,662, filed on Jan. 31, 2017, now abandoned, and a continuation of application No. 14/519,965, filed on Oct. 21, 2014, now Pat. No. 9,598,495.

(60) Provisional application No. 62/012,805, filed on Jun. 16, 2014, provisional application No. 61/979,384, filed on Apr. 14, 2014, provisional application No. 61/893,814, filed on Oct. 21, 2013.

(51) Int. Cl.
| | | |
|---|---|---|
| *A61K 31/31* | (2006.01) | |
| *C07K 16/28* | (2006.01) | |
| *A61K 39/395* | (2006.01) | |
| *A61K 45/06* | (2006.01) | |
| *A61K 39/00* | (2006.01) | |

(52) U.S. Cl.
CPC ...... *C07K 16/2896* (2013.01); *A61K 39/3955* (2013.01); *A61K 45/06* (2013.01); *C07K 16/2803* (2013.01); *A61K 2039/505* (2013.01); *C07K 2317/30* (2013.01); *C07K 2317/56* (2013.01); *C07K 2317/565* (2013.01); *C07K 2317/76* (2013.01)

(58) Field of Classification Search
None
See application file for complete search history.

(56) References Cited

U.S. PATENT DOCUMENTS

| | | | |
|---|---|---|---|
| 5,070,192 A | 12/1991 | Earnshaw et al. | |
| 5,595,756 A | 1/1997 | Bally et al. | |
| 6,497,872 B1 | 12/2002 | Weiss et al. | |
| 6,498,018 B1 | 12/2002 | Carpenter | |
| 6,541,255 B1 | 4/2003 | Snyder et al. | |
| 6,576,754 B2 | 6/2003 | Hall et al. | |
| 6,635,742 B1 | 10/2003 | Boyle et al. | |
| 6,638,501 B1 | 10/2003 | Bjornson et al. | |
| 6,777,233 B2 | 8/2004 | Carpenter | |
| 6,884,879 B1 | 4/2005 | Baca et al. | |
| 7,060,269 B1 | 6/2006 | Baca et al. | |
| 7,169,901 B2 | 1/2007 | Baca et al. | |
| 7,351,803 B2 | 4/2008 | Johnson et al. | |
| 7,407,766 B1 | 8/2008 | Fujisawa et al. | |
| 7,414,108 B2 | 8/2008 | Laus et al. | |
| 7,700,102 B2 | 4/2010 | Hall et al. | |
| 7,919,246 B2 | 4/2011 | Lai et al. | |
| 7,919,594 B2 | 4/2011 | Smith et al. | |
| 8,067,247 B2 | 11/2011 | Belin et al. | |
| 8,496,938 B2 | 7/2013 | Smith et al. | |
| 8,790,652 B2 | 7/2014 | Basile et al. | |
| 8,816,058 B2 | 8/2014 | Smith et al. | |
| 9,090,709 B2 | 7/2015 | Fisher et al. | |
| 9,243,068 B2 | 1/2016 | Evans et al. | |
| 9,249,227 B2 | 2/2016 | Smith et al. | |
| 9,598,495 B2 | 3/2017 | Smith et al. | |
| 2002/0012903 A1 | 1/2002 | Goldman et al. | |
| 2002/0037851 A1 | 3/2002 | Fleckenstein et al. | |
| 2003/0158402 A1 | 8/2003 | Hall et al. | |
| 2005/0147612 A1 | 7/2005 | Yayon et al. | |
| 2006/0147449 A1 | 7/2006 | Brass et al. | |
| 2006/0233793 A1 | 10/2006 | Belin et al. | |
| 2007/0098707 A1 | 5/2007 | Kong-Beltran et al. | |
| 2007/0148177 A1 | 6/2007 | Fyfe et al. | |
| 2007/0154483 A1 | 7/2007 | Fyfe et al. | |
| 2008/0219971 A1 | 9/2008 | Smith et al. | |
| 2009/0104193 A1 | 4/2009 | Lai et al. | |
| 2009/0181035 A1 | 7/2009 | Watts et al. | |

(Continued)

FOREIGN PATENT DOCUMENTS

| | | |
|---|---|---|
| EP | 1365018 A1 | 11/2003 |
| EP | 1442749 A1 | 8/2004 |

(Continued)

OTHER PUBLICATIONS

Tamagnone et al., "Plexins are a Large Family of Receptors for Transmembrane, Secreted, and GPI-Anchored Semaphorins in Vertebrates", Cell, Oct. 1999, pp. 71-80, vol. 99 No. 1, Cell Press, United States.

(Continued)

*Primary Examiner* — John D Ulm
(74) *Attorney, Agent, or Firm* — FisherBroyles, LLP

(57) ABSTRACT

Provided herein are methods for alleviating symptoms in a subject having a neurodegenerative disorder, comprising administering to the subject an effective amount of an isolated binding molecule which specifically binds to semaphorin-4D (SEMA4D) or to its Plexin-B1 or Plexin-B2 receptors.

15 Claims, 19 Drawing Sheets

Figure 1:
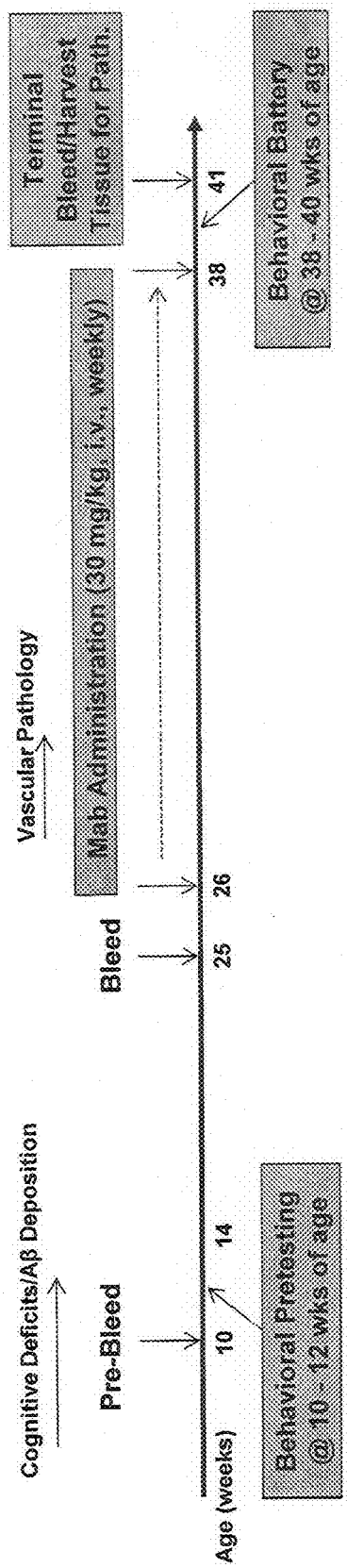

Specification includes a Sequence Listing.

(56) References Cited

U.S. PATENT DOCUMENTS

| | | |
|---|---|---|
| 2010/0040617 A1 | 2/2010 | Brass et al. |
| 2012/0027758 A1 | 2/2012 | Belin et al. |
| 2012/0064035 A1 | 3/2012 | Hadden et al. |
| 2012/0082663 A1 | 4/2012 | Dennis et al. |
| 2013/0095118 A1 | 4/2013 | Smith et al. |
| 2013/0274449 A1 | 10/2013 | Smith et al. |
| 2013/0288927 A1 | 10/2013 | Smith et al. |
| 2013/0302320 A1 | 11/2013 | Smith et al. |
| 2014/0072578 A1 | 3/2014 | Smith et al. |
| 2014/0099334 A1 | 4/2014 | Fisher et al. |
| 2014/0303358 A1 | 10/2014 | Takayanagi |
| 2015/0044219 A1 | 2/2015 | Evans et al. |
| 2015/0104462 A1 | 4/2015 | Zauderer |
| 2016/0115240 A1 | 4/2016 | Evans et al. |
| 2017/0306017 A1 | 10/2017 | Smith et al. |

FOREIGN PATENT DOCUMENTS

| | | |
|---|---|---|
| JP | 2001-157583 A | 6/2001 |
| JP | 2005-500034 A | 1/2005 |
| JP | 2007-308465 A | 11/2007 |
| WO | 93/14125 A1 | 7/1993 |
| WO | 95/07706 A1 | 3/1995 |
| WO | 97/17368 A1 | 5/1997 |
| WO | 2000/028016 A1 | 5/2000 |
| WO | 03/100041 A1 | 12/2003 |
| WO | 2004/067034 A1 | 8/2004 |
| WO | 2005/000900 A1 | 1/2005 |
| WO | 2006/110594 A2 | 10/2006 |
| WO | 2008/100995 A1 | 8/2008 |
| WO | 2010/129917 A2 | 11/2010 |
| WO | 2011/159704 A1 | 12/2011 |
| WO | 2012/157237 A1 | 11/2012 |
| WO | 2013/055922 A1 | 4/2013 |
| WO | 2013/148854 A1 | 10/2013 |
| WO | 2013/170221 A1 | 11/2013 |
| WO | 2014/209802 | 12/2014 |
| WO | 2015/054628 A1 | 4/2015 |
| WO | 2015/061330 A1 | 4/2015 |
| WO | 2017184951 | 10/2017 |
| WO | 2018026715 | 2/2018 |
| WO | 2018156509 | 8/2018 |

OTHER PUBLICATIONS

Taniguchi et al, "Sema4D Deficiency Results in an Increase in the Number of Oligodendrocytes in Healthy and Injured Mouse Brains", Journal of Neuroscience Research, Oct. 2009, pp. 2833-284, vol. 13, Wiley Interscience, United States.

Turner et al., "Plexin-Induced Collapse Assay in COS Cells", Methods in Enzymology, 2006, pp. 665-676, vol. 406, Elsevier Inc., United States.

U.S. Department of Health and Human Services, Food and Drug Administration, Center for Drug Evaluation and Research (CDER), Office of Orphan Products Development (OOPD), "Guidance for Industry—Interpreting Sameness of Monoclonal Antibody Products Under the Orphan Drug Regulations", Apr. 2014, pp. 1-6.

Vajdos et al., "Comprehensive Functional Maps of the Antigen-binding Site of an Anti-ErbB2 Antibody Obtained with Shotgun Scanning Mutagenesis", Journal of Molecular Biology, Jul. 5, 2002, pp. 415-428 at p. 416, vol. 320 No. 2.

Van Nostrand et al., "Enhanced Capillary Amyloid Angiopathy-Associated Pathology in Tg-SwDI Mice With Deleted Nitric Oxide Synthase 2," Stroke, 2010, pp. S135-S138, vol. 41, American Heart Association, Inc., United States.

Voet et al., Biochemistry, 1990, Sec. 6-3 "Chemical Evolution", pp. 126-128 and Sec. 9-3 "Abnormal Hemoglobins", pp. 228-234, Jon Wiley & Sons, Inc., United States.

Waikar et al., "Imperfect Gold Standards for Kidney Injury Biomarker Evaluation", Journal of the American Society of Nephrology, Jan. 2012, pp. 13-21, vol. 23 No. 1.

Wang et al., "Functional Soluble CD100/Sema4D Released from Activated Lymphocytes: Possible Role in Normal and Pathologic Immune Responses", Blood, Jun. 2001, pp. 3498-3504, vol. 97 No. 11, The American Society of Hematology, United States.

Watanabe et al., "Enhanced Immune Response in Transgenic Mice Expressing a Truncated Form of the Lymphocyte Semaphorin CD100", The Journal of Immunology, Aug. 2001, pp. 4321-4328, The American Association of Immunologists, United States.

Waubant, "Biomarkers indicative of blood-brain barrier disruption in multiple sclerosis," Disease Markers, 2006, pp. 235-244, vol. 22, IOS Press.

Westin et al., "Endothelial Proliferation and Increased Blood-Brain Barrier Permeability in the Basal Ganglia in a Rat Model of 3,4-Dihydroxyphenyl-L-Alanine-Induced Dyskinesia," The Journal of Neuroscience, 2006, pp. 9448-9461, vol. 26, No. 37, Society for Neuroscience, United States.

Whitham et al., "Lymphocytes from SJL/J Mice Immunized with Spinal Cord Respond Selectively to a Peptide of Proteolipid Protein and Transfer Relapsing Demyelinating Experimental Autoimmune Encephalomyelitis", The Journal of Immunology, Jan. 1, 1991, pp. 101-107, vol. 146 No. 1.

Whitton, "Inflammation as a causative factor in the aetiology of Parkinson's disease," British Journal of Pharmacology, 2007, pp. 963-976, vol. 150, Nature Publishing Group, England.

Wilcock et al., "Amyloid reduction by amyloid-b vaccination also reduces mouse tau pathology and protects from neuron loss in two mouse models of Alzheimer's disease," The Journal of Neuroscience, 2009, pp. 7957-7965, vol. 29 No. 25, Society for Neuroscience, United States.

Witherden et al., "The CD100 Receptor Interacts with Its Plexin B2 Ligand to Regulate Epidermal gs T Cell Function," Immunity, 2012, pp. 314-325, vol. 37 No. 2, Cell Press, United States.

Wolburg et al., "The Disturbed Blood-Brain Barrier in Human Glioblastoma", Molecular Aspects of Medicine, 2012, pp. 579-589, vol. 33.

Wu et al., "Humanization of a Murine Monoclonal Antibody by Simultaneous Optimization of Framework and CDR Residues", Journal of Molecular Biology, 1999, pp. 151-162, vol. 294.

Wu, "Simultaneous Humanization and Affinity Optimization of Monoclonal Antibodies", Methods in Molecular Biology, Jan. 2003, pp. 197-212, vol. 207, Humana Press, Inc., New Jersey, United States.

Xiao-Guang et al., "Preparation and Identification of Monoclonal Antibodies Against CD100 Molecule", Chinese Journal of Cellular and Molecular Immunology, Jan. 2003, pp. 80-82, vol. 19 No. 1, Abstract.

Young et al., "Efficient Isolation of Genes by Using Antibody Probes", Proceedings of the National Academy of Sciences, Mar. 1983, pp. 1194-1196, vol. 80, National Academy of Sciences, United States.

Zhang et al., "Sema 4D/CD100-plexin B is a Multifunctional Counter-Receptor", Cellular and Molecular Immunology, 2013, pp. 97-98, vol. 10.

Zhong et al., "ALS-causing SOD1 mutants generate vascular changes prior to motor neuron degeneration," Nature Neuroscience, 2008, pp. 420-422, vol. 11 No. 4, Nature Publishing Group, United States.

Zhou et al., "Semaphorin 4D Cooperates with VEGF to Promote Angiogenesis and Tumor Progression", Angiogenesis, 2012, pp. 391-407, vol. 15 Issue 3.

Zhu et al., "Semaphorin 4D (CD100) Is Expressed on the Surface of Human Platelets and Proteolytically Shed During Platelet Activation", Blood, Nov. 2003, Abstract No. 1043, vol. 102 No. 11, The American Society of Hematology, United States (Abstract Only).

Zlokovic, "Neurovascular Pathways to Neurodegeneration in Alzheimer's Disease and other Disorders", Nature Reviews-Neuroscience, Dec. 2011, pp. 723-738, vol. 12.

Zlokovic, B.V., "The Blood-Brain Barrier in Health and Chronic Neurodegenerative Disorders," Neuron, 2008, pp. 178-201, vol. 57, Elsevier Inc., United States.

Office Action for U.S. Appl. No. 13/842,523 dated Mar. 25, 2016.
Office Action for U.S. Appl. No. 13/649,651 dated Mar. 30, 2016.

(56) References Cited

OTHER PUBLICATIONS

Svendsen et al., Long-Term Survival of Human Central Nervous System Progenitor Cells Transplanted into a Rat Model of Parkinson's Disease, Exp. Neurol. 148(1): 135-146 (1997).
Palmer et al., "Progenitor Cells from Human Brain After Death", Nature, vol. 411, No. 6833, pp. :42-43 (2001).
Palmer et al., "The Adult Rat Hippocampus Contains Primordial Neural Stem Cells", Molecular Cell Neurosci , vol. 8, No. 6, pp. 389-404 (1997).
Shisabuddin, "The Search for Neural Progenitor Cells: Prospects for the Therapy of Neurodegenerative Disease", Molecular Medicine Today 5(1):474-480 (1999).
Office Action for U.S. Appl. No. 13/797,048 dated Jun. 17, 2016.
Witherden et al., "The CD100 Receptor Interacts with Its Plexin B2 Ligand to Regulate Epidermal ys T Cell Function," Immunity, 2012, pp. 314-325, vol. 37 No. 2.
Fabis et al., "Loss of Blood-Brain Barrier Integrity in the Spinal Cord is Common to Experimental Allergic Encephalomyelitis in Knockout Mouse Models", Proceedings of the National Academy of Sciences of the United States of America, Mar. 27, 2007, pp. 5656-5661, vol. 104, No. 13.
Okuno et al., "Examination of Effect of Sema4D Inhibitition Therapy Against Experimental Autoimmune Encephalomyelitis (EAE) and its Action Mechanism" , Department of Immunopathology, Research Institute for Microbial Diseases and Department of Neurology, Osaka University Graduate, School of Medicine, 2010, pp. 1094, vol. 50, No. 12.
Office Action for U.S. Appl. No. 13/842,523 dated Aug. 24, 2016.
Colangelo et al., "Astrogliosis as a Therapeutic Target for Neurodegenerative Diseases", Neuroscience Letters, 2014, pp. 59-64, No. 565.
Piore, "The Rouge Immune Cells that Wreck the Brain", MIT Technology Review 119, 2016, 12 pp. No. 3.
Maragakis et al., "Mechanisms of Disease: Astrocytes in Neurodegenerative Disease", Nature Clinical Practice Neurology, 2006, pp. 679-698, vol. 2, No. 12.
Brambilla et al., "Astrocyte Signaling and Neurodegeneration, New Insights into CNS Disorders", Prion, 2013, pp. 29-36, vol. 7, No. 1.
Vargas et al., "Astrogliosis in Amyotrophic Lateral Sclerosis: ROle and Therapeutic Potential of Astrocytes", Neurotherapeutics, 2010, pp. 471-481, vol. 7, No. 4.
Evans et al., "Inflammation and Neurovascular Changes in Amyotrophic Lateral Sclerosis", Molecular and Cellular Neuroscience, 2013, pp. 34-41, No. 53.
Anthony et al., "Special Issue Commentary: The Changing Face of Inflammation in the Brain", Molecular and Cellular Neuroscience, 2013, pp. 1-5, No. 53.
Okuno et al., "Roles of Sema4D_Plexin-B1 Interactions in the Central Nervouse System for Pathogenesis of Experimental Autoimmune Encephalomy Elitis", The Journal of Immunology, 2010, pp. 1499-1506, vol. 184, No. 3.
Vezzani et al., "The Role of Inflammation in Epilepsy", Nature Reviews Neurology, Jan. 2011, pp. 31-40, vol. 7 No. 1.
Office Action for U.S. Appl. No. 13/649,651 dated Sep. 28, 2016.
Fanning et al., "Development of the Immunoglobulin Repertoire", Clinical Immunology and Immunopathology, Apr. 1, 1996, pp. 1-14, vol. 79 No. 1.
Fisher et al., "Development of Anti-SEMA4D Monoclonal Antibody for the Treatment of Multiple Sclerosis", 5th Joint Triennial Congress of the European and Americas Committees for Treatment and Research in Multiple Sclerosis, Oct. 19, 2011-Oct. 22, 2011, Amsterdam, The Netherlands, Poster.
Fisher et al., "Development of Anti-SEMA4D Monoclonal Antibody for the Treatment of Multiple Sclerosis", 5th Joint Triennial Congress of the European and Americas Committees for Treatment and Research in Multiple Sclerosis, Oct. 19, 2011-Oct. 22, 2011, Amsterdam, The Netherlands, retrieved from http://registration.akm.ch/einsicht.php?XNABSTRACT_ID=1383468XNSPRACCHE on Jun. 10, 2015.

Fishwild et al., "High-Avidity Human IgGIC Monoclonal Antibodies from a Novel Strain of Minilocus Transgenic Mice", Nature Biotechnology, May 1996, pp. 845-851, vol. 14, Nature Publishing Group, United States.
Fujioka et al., "Neurotrophic Effect of Semaphorin 4D in PC12 Cells", Biochemical and Biophysical Research Communications, Feb. 2003, pp. 304-310, vol. 301 No. 2, Elsevier Science, United States.
Furuyama et al., "Identification of a Novel Transmembrane Semaphorin Expressed on Lymphocytes", Journal of Biological Chemistry, Dec. 27, 1996, pp. 33376-33381, vol. 271 No. 52.
Garbuzova-Davis et al., "Amyotrophic Lateral Sclerosis: A Neurovascular Disease", Brain Research, 2011, pp. 113-125, vol. 1398.
Gauld et al., "B Cell Antigen Receptor Signaling: Roles in Cell Development and Disease", Science, May 2002, pp. 1641-1642, vol. 296, The American Association for the Advancement of Science, Untied States.
Giordano et al., "The Semaphorin 4D Receptor Controls Invasive Growth by Coupling with Met", Nature Cell Biology, Sep. 2002, pp. 720-724, vol. 4 No. 9, Nature Publishing Group, England.
Giraudon et al., "Semaphorin CD100 from Activated T Lymphocytes Induces Process Extension Collapse in Oligodendrocytes and Death of Immature Neural Cells", Journal of Immunology, 2004, pp. 1246-1255, vol. 172 No. 2, The American Association of Immunologists, United States.
Giraudon et al., "T-Cells in Neuronal Injury and Repair: Semaphorins and Related T-Cell Signals", Neuromolecular Medicine, Jun. 2005, pp. 207-216, vol. 7 No. 3, Humana Press, Inc., United States.
Glaser et al., "Dissection of the Combining Site in a Humanized Anti-Tac Antibody", The Journal of Immunology, Oct. 15, 1992, pp. 2607-2614, vol. 149 No. 8.
Goldsby et al., "Autoimmunity", Kuby Immunology, 2000, pp. 502-504, vol. 4, W.H. Freeman and Company, United States.
Goldstein et al., "The Blood-Brain Barrier," Scientific American, 1986, pp. 74-83, vol. 255 No. 3, New York.
Gonzalez-Velasquez et al,, "Soluble aggregates of the amyloid-b protein selectively stimulate permeability in human brain microvascular endothelial monolayers," Journal of Neurochemistry, 2008, pp. 466-477, vol. 107, International Society for Neurochemistry, England.
Gouttefangeas et al., "Differential Proliferative Responses in Subsets of Human CD28+ Cells Delineated by BB27 mAb", International Immunology, Nov. 1993, pp. 423-430, vol. 6 No. 3, Oxford University Press, Oxford.
Gowdie et al., "Primary and Secondary Central Nervous System Vasculitis", Journal of Child Neurology, 2012, pp. 1448-1459, vol. 27 No. 11.
Guido et al., "Virtual Screening and its Integration with Modern Drug Design Technologies", Current Medicinal chemistry, 2008, pp. 37-46, vol. 15 No. 1, Bentham Science Publishers Ltd.
Gura, "Systems for Identifying New Drugs are Often Faulty", Science, Nov. 7, 1997, pp. 1041-1042, vol. 278 No. 5340.
Gursoy-Ozdemir et al., "Microvascular Protection is Essential for Successful Neuroprotection in Stroke", Journal of Neurochemistry, 2012, pp. 2-11, vol. 123 Suppl. 2.
Hajj-Ali et al., "Primary Angiitis of the Central Nervous System", Autoimmunity Reviews, 2013, pp. 463-466, vol. 12.
Hall et al., "Human CD100, A Novel Leukocyte Semaphorin That Promotes B-Cell Aggregation and Differentiation", Proceeding of the National Academy of Sciences, Oct. 1996, pp. 11780-11785, vol. 93, National Academy of Sciences.
Hawkins et al., "The Blood-Brain Barrier/Neurovascular Unit in Health and Disease," Pharmacological Reviews, 2005, pp. 173-185, vol. 57 No. 2, The American Society for Pharmacology and Experimental Therapeutics, United States.
Hebert et al., "The Molecular Dating Game: An Antibody Heavy Chain Hangs Loose with a Chaperone while Waiting for Its Life Partner", Molecular Cell, 2009, pp. 635-636, vol. 34 No. 6, Cell Press, United States.
Herold et al., "Activation Signals Are Delivered Through Two Distinct Epitopes of CD100, A Unique 150 kDa Human Lympho-

(56) References Cited

OTHER PUBLICATIONS cyte Surface Structure Previously Defined by BB18 mAb", International Immunology, Sep. 1994, pp. 1-8, vol. 7 No. 1, Oxford University Press, England.

Herold et al., "CD100 Defines a Newly Identified 150-kDa Human Lymphocyte Surface Structure" T-Cell Antigens-Papers, 1994, pp. 50-51, vol. T1.

Hinson et al., "Neurological Autoimmunity Targeting Aquaporin-4", Neuroscience, 2010, pp. 1009-1018, vol. 168.

International Preliminary Report on Patentability (Chapter I) for PCT/US2013/040661 dated Nov. 20, 2014.

International Search Report and Written Opinion for PCT/US2013/040661 dated Oct. 8, 2013.

International Search Report and Written Opinion for PCT/US2014/060129 dated Jan. 15, 2015.

International Search Report and Written Opinion for PCT/US2014/061592 dated Jan. 21, 2015.

Ishida et al., "Involvement of CD100, A Lymphocyte Semaphorin, in the Activation of the Human Immune System Via CD72: Implications for the Regulation of Immune and Inflammatory Responses", International Immunology, May 2003, pp. 17-23, vol. 15 No. 8, Oxford University Press, England.

Ito et al., "Sema4D/Plexin-B1 Activates GSK-3beta Through R-Ras GAP Activity, Inducing Growth Cone Collapse", EMBO Reports, 2006, pp. 704-709, vol. 7 No. 7.

Iwahashi et al., "CDR Substitutions of a Humanized Monoclonal Antibody (CC49): Contributions of Individual CDRs to Antigen Binding and Immunogenicity", Molecular Immunology, 1999, pp. 1079-1091, vol. 36.

Janssen et al., "Structural basis of semaphorin-plexin signaling," Nature, 2010, pp. 1118-1122, vol. 467, Nature Publishing Group, England.

Jenkins et al., "Antigen Presentation by Chemically Modified Splenocytes Induces Antigen-Specific T Cell Unresponsiveness In Vitro and In Vivo", Journal of Experimental Medicine, Feb. 1987, pp. 302-319, vol. 165 No. 2.

Jonason et al., "Development of an anti-SEMA4D monoclonal antibody for the treatment of Multiple Sclerosis", 5th Joint Triennial Congress of the European and Americas Committees for Treatment and Research in Multiple Sclerosis, Oct. 19-22, 2011, Amsterdam, The Netherlands.

Kalaria, "The Blood-Brain Barrier and Cerebral Microcirculation in Alzheimer Disease," Cerebrovascular and Brain Metabolism Reviews, 1992, pp. 226-260, vol. 4, Raven Press, Ltd., New York.

Kato et al., "Semaphorin 4D, a Lymphocyte Semaphorin, Enhances Tumor Cell Motility Through Binding its Receptor, Plexin B1, in Pancreatic Cancer", Cancer Science, 2011, pp. 2029-2037, vol. 102.

Kikutani et al., "Semaphorins in Interactions Between T Cells and Antigen-Presenting Cells", Nature Reviews Immunology, Feb. 2003, pp. 159-167, vol. 3, Nature Publishing Group, United States.

Kleinschmidt-Demasters et al., "Update on PML and PML-IRIS Occurring in Multiple Sclerosis Patients Treated with Natalizumab", Journal of Neuropathology & Experimental Neurology, Jul. 2012, pp. 604-617, vol. 71 No. 7.

Kornbluth et al., "Novel Tyrosine Kinase Identified by Phosphotyrosine Antibody Screening of cDNA Libraries", Molecular and Cellular Biology, Sep. 1988, pp. 5541-5544, vol. 8 No. 12, American Society for Microbiology, United States.

Kortekaas et al., "Blood-brain barrier dysfunction in parkinsonian midbrain in vivo.", Annals of Neurology, 2005, pp. 176-179, vol. 57, The American Neurological Association, United States.

Kruger et al., "Semaphorins Command Cells to Move", Nature Reviews Molecular Cell Biology, Oct. 2005, pp. 789-800, vol. 6, Nature Publishing Group, London.

Kumanogoh et al., "Class IV Semaphorin Sema4A Enhances T-Cell Activation and Interacts with Tim-2", Nature, Oct. 2002, pp. 629-633, vol. 419 No. 6907, Nature Publishing Group, London.

Kumanogoh et al., "Identification of CD72 as a Lymphocyte Receptor for the Class IV Semaphorin CD100: A Novel Mechanism for Regulating B Cell Signaling", Immunity, Nov. 2000, pp. 621-631, vol. 13 No. 5, Cell Press, Cambridge, Massachusetts.

Kumanogoh et al., "Immune Semaphorins: A New Area of Semaphorin Research", Journal of Cell Science, Sep. 2003, pp. 3463-3470, vol. 116, The Company of Biologists Ltd., United Kingdom.

Kumanogoh et al., "Requirement for CD100-CD72 Interaction in Fine-Tuning of B-Cell Antigen Receptor Signaling and Homeostatic Maintenance of the B-Cell Compartment", International Immunology, 2005, pp. 1277-1282, vol. 17 No. 10, The Japanese Society for Immunology, Oxford University Press, England.

Kumanogoh et al., "Requirement for the Lymphocyte Semaphorin CD100, in the Induction of Antigen-Specific T Cells and the Maturation of Dendritic Cells", Journal of Immunology, Aug. 2002, pp. 1175-1181, The American Association of Immunologists, United States.

Kumanogoh et al., "The CD100-CD72 Interaction: A Novel Mechanism of Immune Regulation" Trends in Immunology, Dec. 2011, pp. 670-676, vol. 22 No. 12, Elsevier Science Ltd., United States.

Aagaard et al., "RNAi Therapeutics: Principles, Prospects and Challenges", Advanced Drug Delivery Reviews, Mar. 4, 2007, pp. 75-86, vol. 59.

Alberts et al., "The Generation of Antibody Diversity", Molecular Biology of the Cell—4th Edition, 1-10, 2002, Garland Science, New York.

Argaw et al., "VEGF-mediated disruption of endothelial CLN-5 promotes blood-brain barrier breakdown," PNAS, 2009, 106(6): 1977-1982, The National Academy of Sciences of the USA, United States.

Banks et al., "The blood-brain barrier and immune function and dysfunction," Neurobiology of Disease, 2010, pp. 26-32, vol. 37, Elsevier Inc.

Basile et al., "Plexin-B1 Utilizes RhoA and Rho Kinase to Promote the Integrin-dependent Activation of Akt and Erk and Endothelial Cell Motility", Journal of Biological Chemistry, 2007, pp. 34888-34895, vol. 282 No. 48.

Basile, J. R, et al., "Semaphorin 4D provides a link between axon guidance processes and tumor-induced angiogenois," PNAS 103(24):9017-9022, The National Academy of Sciences of the USA, United States (2006).

Baxter et al., "Activation Rules: The Two-Signal Theories of Immune Activation", Nature Reviews Immunology, Jun. 2002, pp. 439-446, vol. 2 No. 6.

Beam et al., "Blood, Brain, and Cerebrospinal Fluid Concentrations of Several Antibiotics in Rabbits with Intact and Inflamed Meninges," Antimicrobial Agents and Chemotherapy, 1977, pp. 710-716, vol. 12 No. 6, American Society for Microbiology, United States.

Billard et al., "Switch in the Protein Tyrosine Phosphatase Associated with Human CD 100 Semaphorin at Terminal B-Cell Differentiation Stage", Blood, Feb. 2000, pp. 965-972, vol. 95 No. 3, The American Society of Hematology, United States.

Bleck et al., "An Alternative Method for the Rapid Generation of Stable, High-Expressing Mammalian Cell Lines", Bioprocessing Journal, Sep.-Oct. 2005, pp. 36-42, vol. 5 No. 4, International Society for BioProcess Technology, United States.

Bork "Powers and Pitfalls in Sequence Analysis: The 70% Hurdle", Genome Research, 2000, pp. 398-400, vol. 10, Cold Spring Harbor Laboratory Press.

Bougeret et al, "Increased Surface Expression of a Newly Identified 150-kDa Dimer Early After Human T Lymphocyte Activation" The Journal of Immunology, Jan. 1992, pp. 318-323, vol. 148 No. 2, The American Association of Immunologists, United States.

Bowie et al., "Deciphering the Message in Protein Sequences: Tolerance to Amino Acid Substitutions", Science, Mar. 16, 1990, pp. 1306-1310, vol. 247 No. 4948.

Brand et al., "Collagen-Induced Arthritis", Nature Protocols, May 2007, pp. 1269-1275, vol. 2 No. 5, Nature Publishing Group, England.

Bretscher et al., A Theory of Self-Nonself Discrimination, Science, Sep. 11, 1970, pp. 1042-1049, vol. 169 No. 3950.

Brown et al., "Tolerance to Single, but Not Multiple, Amino Acid Replacements in Antibody VH CDR2: A Means of Minimizing B Cell Wastage from Somatic Hypermutation?", Journal of Immunol-

(56) References Cited

OTHER PUBLICATIONS ogy, May 1996, pp. 3285-3291 at 3290 and Tables 1 and 2, vol. 156 No. 9, The American Association of Immunologists.

Burgess et al., "Possible Dissociation of the Heparin-Binding and Mitogenic Activities of Heparin-Binding (Acidic Fibroblast) Growth Factor-1 From Its Receptor-Binding Activities by Site-Directed Mutagenesis of a Single Lysine Residue", The Journal of Cell Biology, Nov. 1990, pp. 2129-2138, The Rockefeller University Press, United States.

Bussolino et al., "Molecular Mechanisms of Blood Vessel Formation," Trends in Biochemical Sciences, 1997, pp. 251-256, vol. 22 No. 7, Elsevier Trends Journals, England.

Carmeliet, "Angiogenesis in health and disease," Nature Medicine, 2003, pp. 653-660, vol. 9 No. 6, Nature Publishing Company, United States.

Ch'ng et al., "Prognostic Significance of CD100 Expression in Soft Tissue Progression", Cancer, 2007, pp. 164-172 vol. 110 Issue 3.

Chabbert-De Ponnat et al., "Soluble CD100 Functions on Human Monocytes and Immature Dendritic Cells Require Plexin C1 and Plexin B1, Respectively", International Immunology, 2005, pp. 439-447, vol. 4, Oxford University Press, England.

Chen et al., "Generation and Analysis of Random Point Mutations in an Antibody CDR2 Sequence: Many Mutated Antibodies Lose their Ability to Bind Antigen", Journal of Experimental Medicine, Sep. 1992, pp. 855-866, vol. 176.

Cheung et al., "Age-Related Macular Degeneration", Pharmacotherapy, 2013, pp. 838-855, vol. 33 No. 8 [Epub ahead of print], 18 pages.

Chodobski et al., "Blood-Brain Barrier Pathophysiology in Traumatic Brain Injury", Translational Stroke Research, Dec. 2011, pp. 492-516, vol. 2 No. 4.

Claesson-Welsh., "Novel Paths to Blood Vessel Formation", Blood, Jun. 2005, pp. 4153-4154, vol. 105 No. 11, The American Society of Hematology, United States.

Clark et al., "Discovery and Development of Janus Kinase (JAK) Inhibitors for Inflammatory Diseases", Journal of Medicinal Chemistry, Jan. 13, 2014, pp. 5023-5038, vol. 57, American Chemical Society.

Colman et al., "Effects of Amino Acid Sequence Changes on Antibody-Antigen Interactions", Research in Immunology, 1994, pp. 33-36, vol. 145.

Colton et al., "The Effects of NOS2 Gene Deletion on Mice Expressing Mutated Human AbPP," Journal of Alzheimer's Disease, 2008, pp. 571-587, vol. 15 No. 4, IOS Press, Netherlands.

Combes et al., "The Crossroads of Neuroinflammation in Infectious Diseases: Endothelial Cells and Astrocytes", Trends in Parasitology, Aug. 2012, pp. 311-319, vol. 28, No. 8.

Conrotto et al, "Sema4D Induces Angiogenesis Through Met Recruitment by Plexin B1", Blood, Jun. 2005, pp. 1321-4329, vol. 105 No. 11, The American Society of Hematology, United States.

Cornelius et al., "Abstract 936: Nonclinical Safety and Pharmacology of VX15/2503: a Humanized IgG4 Monoclonal Antibody to SEMA4D", Cancer Research, Apr. 15, 2012, retrieved from http://cancerres,aacrjournals.org/content/72/8_Supplement/936.short on Sep. 25, 2015, the whole document.

Cucullo et al., "A Dynamic In Vitro BBB Model for the Study of Immune Cell Trafficking into the Central Nervous System," Journal of Cerebral Blood Flow & Metabolism, 2011, pp. 767-777, vol. 31, Nature Publishing Group, United States, Epub. Sep. 15, 2010.

Cucullo et al., "A New Dynamic in Vitro Model for the Multidimensional Study of Astrocyte-endothelial Cell Interactions at the Blood-brain Barrier," Brain Research, 2002, pp. 243-254, vol. 951, Elsevier Science B.V.

Cucullo et al., "Development In Vitro Blood-Brain Barrier Model to Screen for Brain Penetration of Antiepileptic Drugs," Epilepsia, 2007, pp. 505-516, vol. 48 No. 3, Blackwell Publishing, Inc., England.

Curran et al., "Systemic 4-1BB Activation Induces a Novel T cell Phenotype Driven by High Expression of Eomesodermin", The Journal of Experimental Medicine, 2013, pp. 743-755, vol. 210.

Dacquin et al., "Control of Bone Resorption by Semaphorin 4D is Dependent on Ovarian Function", PLOS One, Oct. 26, 2011, pp. e26627, vol. 6 No. 10.

Database GenBank, Apr. 18, 2005, Adams, "M.Musculus mRNA for Semaphorin B", Data Accession No. X85991.

Database GenBank, Apr. 24, 1997, Hillier et al., "zt85a06.r1", Data Accession No. AA394007.

Database GenBank, Jan. 31, 1997, Strausberg, "zs16g08.r1", Data Accession No. AA262446.

De Pascalis et al., "Grafting of 'Abbreviated' Complementarity-Determining Regions Containing Specificity-Determining Residues Essential for Ligand Contact to Engineer a Less Immunogenic Humanized Monoclonal Antibody", Journal of Immunology, Sep. 15, 2002, pp. 3076-3084, vol. 169 No. 6.

Deaglio et al., "CD38 and CD100 Lead a Network of Surface Receptors Relaying Positive Signals for B-CLL Growth and Survival", Blood, Apr. 2005, pp. 3042-3050, The American Society of Hematology, United States.

Deane et al, "LRP/Amyloid b-Peptide Interaction Mediates Differential Brain Efflux of Ab Isoforms," Neuron, 2004, pp. 333-344, vol. 43, Cell Press, United States.

Delaire et al., "Biological Activity of Soluble CD100. II Soluble CD100, Similarly to H-Sema III, Inhibits Immune cell Migration", The Journal of Immunology, Jan. 2001, pp. 4348-4354, vol. 166, The American Association of Immunologists, United States.

Delaire et al., "Inhibition of Immune Cell Migration by Soluble CD100 and H-Sema III Semaphorins", Tissue Antigens, 2000, pp. 103, vol. 55 No. 1, Wiley-Blackwell, England (Abstract Only).

Duran-Struuck et al., "A Novel Role for the Semaphorin Sema4D in the Induction of Allo-Responses", Biological Blood Marrow Transplant, Nov. 2007, pp. 1294-1303, vol. 13 No. 11.

Elhabazi et al., "Biological Activity of Soluble CD100. I. The Extracellular Region of CD100 is Released from the Surface of T Lymphocytes by Regulated Proteolysis", The Journal of Immunology, Jan. 2001, pp. 4341-4347, vol. 166, The American Association of Immunologists, United States.

Elhabazi et al., "Structure and Function of the Immune Semaphorin CD100/SEMA4D", Critical Review in Immunology, 2003, pp. 65-81, vol. 23 No. 1-2, Begell House, Inc. United States.

Elhabazi et al., "The Human Semaphorin-Like Leukocyte Cell Surface Molecule CD100 Associates with a Serine Kinase Activity", The Journal of Biological Chemistry, Sep. 1997, pp. 23515-23520, vol. 272 No. 38, The American Society for Biochemistry and Molecular Biology, Inc., United States.

Engelhardt et al., "Capture, Crawl, Cross: The T Cell Code to Breach the Blood-Brain Barriers", Trends in Immunology, Dec. 2012, pp. 579-589, vol. 33 No. 12.

Extended European Search Report for EP Application 13787931.8 dated Oct. 16, 2015.

Lafferty et al., "A New Analysis of Allogeneic Interactions", Australian Journal Experimental Biology and Medical Science, 1975, pp. 27-42, vol. 53 No. 1.

Lamminmaki et al., "Crystal Structure of a Recombinant Anti-Estradiol Fab Fragment in Complex with 17?-Estradiol", Journal of Biological Chemistry, 2001, pp. 36687-36694, vol. 276 No. 39.

Lazar et al., "Transforming Growth Factor alpha: Mutation of Aspartic Acid 47 and Leucine 48 Results in Different Siological Activities"., Molecular Cell Biology, Mar. 1988, pp. 1247-1252, vol. 8 No. 3, The American Society for Microbiology, United States.

Levin et al., "Molecular Mimicry to Neurons Results in Neurological Disease", Abstract Viewer and Itinerary Planner, 2002, Program No. 415.3, Society for Neuroscience, Washington DC (Abstract Only).

Li et al., "CD72 Down-Modulates BCR-Induced Signal Transduction and Diminishes Survival in Primary Mature B Lymphocytes", The Journal of Immunology, May 2006, pp. 5321-5328, vol. 176, The American Association of Immunologists, United States.

Li et al., "Modulation of Peripheral B Cell Tolerance by CD72 in a Murine Model", Arthritis and Rheumatism, Oct. 2008, pp. 3192-3904, vol. 58 No. 10, The American College of Rheumatology, United States.

Lochhead et al., "Oxidative stress increases blood-brain barrier permeability and induces alterations in occludin luring hypoxia-

(56) References Cited

OTHER PUBLICATIONS reoxygenation," Journal of Cerebral Blood Flow & Metabolism, 2010, pp. 1625-1636, vol. 30, Nature Publishing Group, United States.

Love et al., "The ligand-binding face of the semaphorins revealed by the high-resolution crystal structure of SEMA4D," Nature Structural and Molecular Biology, 2003, pp. 843-848, vol. 10, Nature Pub. Co., United States.

Lu et al., "Targeting Metabolic Inflammation in Parkinson's Disease: Implications for Prospective Therapeutic Strategies", Clinical and Experimental Pharmacology and Physiology, 2012, pp. 577-585, vol. 39.

Lyketsos et al., "Neuropsychiatric Symptoms in Alzheimer's Disease", Alzheimer's & Dementia, Sep. 2011, pp. 1-14, vol. 7 No. 5.

Maccallum et al., "Antibody-Antigen Interactions: Contact Analysis and Binding Site Topography", Journal of Molecular Biology, 1996, pp. 732-745, vol. 262.

Machine-generated English language translation of the French Patent Publication No. FR 2686087 A1, filing date Jan. 13, 1993 (corresponds to International Patent Application No. WO 93/14125 A1), European Patent Office, espacenet database—Worldwide (1993) (equivalent of document FP1 cited on the accompanying form PTO/SB/08A).

Marco et al., "Amyloid b-peptide 1-42 alters tight junction protein distribution and expression in brain microvessel endothelial cells." Neuroscience Letters, 2006, pp. 219-224, vol. 401, Elsevier Ireland Ltd.

Maroso et al., "Toll-Like Receptor 4 and High-Mobility Group Box-1 are Involved in Ictogenesis and can be Targeted to Reduce Seizures", Nature Medicine, Apr. 2010, vol. 16 No. 4.

Miller et al., "Experimental autoimmune encephalomyelitis in the mouse" Current Protocols in Immunology, 2007, pp. 15.1.1-15.1.18, John Wiley & Sons, Inc.

Minagar et al., "Blood-brain barrier disruption in multiple sclerosis," Multiple Sclerosis, 2003, pp. 540-549, vol. 9, Arnold, England.

Mizrahi et al., "CD100 on NK Cells Enhance IFN[gamma] Secretion and Killing of Target Cells Expressing CD72", PLOS One, Jan. 2007, pp. e818, vol. 2 No. 9, New York University School of Medicine, United States.

Mogi et al., "Neurovascular Coupling in Cognitive Impairment Associated with Diabetes Mellitus", Circulation Journal, May 2011, pp. 1042-1048, vol. 75.

Moreau-Fauvarque et al., "The Transmembrane Semaphorin Sema4d/CD100, an Inhibitor of Axonal Growth, Is Expressed on Oligodendrocytes and Upregulated After CNS Lesion", Journal of Neuroscience, 2003, pp. 9229-9239, vol. 27, The Society for Neuroscience, United States.

Negishi-Koga et al., "Suppression of bone formation by osteoclastic expression of semaphorin 4D", Nature Medicine, 2011, pp. 1473-1480, vol. 17 No. 11.

Nelson, "Antibody Fragments", Landes Bioscience, Nov. 27, 2009, pp. 77-83, vol. 2 Issue 1.

Nuber et al., "Neurodegeneration and Motor Dysfunction in a Conditional Model of Parkinson's Disease", Journal of Neuroscience, Mar. 5, 2008, pp. 2471-2484, vol. 28 No. 10.

Oby et al., "The Blood-Brain Barrier and Epilepsy," Epilepsia, 2006, pp. 1761-1774, vol. 47 No. 11, Blackwell Publishing, Inc., England.

Office Action for U.S. Appl. No. 13/649,651 dated Jul. 28, 2015.
Office Action for U.S. Appl. No. 13/649,651 dated Mar. 5, 2014.
Office Action for U.S. Appl. No. 13/649,651 dated Oct. 31, 2014.
Office Action for U.S. Appl. No. 14/753,882 dated Sep. 18, 2015.

Oinuma et al., "Semaphorin 4D/Plexin-B1-Mediated R-Ras GAP Activity Inhibits Cell Migration by Regulating beta-1 Integrin Activity", The Journal of Cell Biology, 2006, pp. 601-613, vol. 173 No. 801.

Okuno et al., "Roles of Sema4D-Plexin-B1 Interactions in the Central Nervous System for Pathogenesis of Experimental Autoimmune Encephalomyelitis", The Journal of Immunology, Feb. 2010, pp. 1499-1506, vol. 184, The American Association of Immunologists, United States.

Okuno et al., "The Role of Immune Semaphorins in Multiple Sclerosis", Federation of European Biochemical Societies Letters, 2011, pp. 3829-3835, vol. 585.

Pardridge, "Receptor-Mediated Peptide Transport Through the Blood-Brain Barrier," Endocrine Reviews, 1986, pp. 314-330, vol. 7, The Endocrine Society.

Pasterkamp, "R-Ras Fills Another GAP in Semaphorin Signaling", Trends in Cell Biology, Feb. 2005, pp. 61-64, vol. 15 No. 2, Elsevier, England.

Ransohof et al., "Three or More Routes for Leukocyte Migration Into the Central Nervous System," Nature Reviews Immunology, 2003, pp. 569-581, vol. 3, Nature Publishing Group.

Regev et al., "Semaphorin-4D (Sema-4D), the Plexin-B1 Ligand, is Involved in Mouse Ovary Follicular Development", Reproductive Biology and Endocrinology, 2007, vol. 5 Issue 12, 8 pages.

Riemer et al., "Matching of Trastuzumab (Herceptin) Epitope Mimics Onto the Surface of Her-2/neu—A New Method of Epitope Definition", Molecular Immunology, 2005, pp. 1121-1124, vol. 42.

Risau, "Mechanisms of angiogenesis," Nature, 1997, pp. 671-674, vol. 386, No. 6626, Nature Publishing Group, England.

Roth et al., "The Many Faces of Semaphorins: From Development to Pathology", CMLS Cellular and Molecular Life Sciences, Oct. 27, 2008, pp. 649-666, vol. 66 No. 4.

Rudikoff et al., "Single Amino Acid Substitution Altering Antigen-Binding Specificity", Proceedings of the National Academy of Sciences, Mar. 1982, pp. 1979-1983, vol. 79, National Academy of Sciences United States.

Sagare et al., "Neurovascular Dysfunction and Faulty Amyloid beta-Peptide Clearance in Alzheimer Disease", 2012, Cold Spring Harbor Perspectives in Medicine, pp. a011452, vol. 2.

Sanchez-Del-Rio et al., "Migraine Aura: New Information on Underlying Mechanisms", Current Opinion in Neurology, 2004, pp. 289-293, vol. 17.

Santaguida et al., "Side by side comparison between dynamic versus static models of blood-brain barrier in vitro: a permeability study," Brain Research, 2006, pp. 1-13, vol. 1109, Elsevier B.V.

Shi et al., "The Class IV Semaphorin CD100 Plays Nonredundant Roles in the Immune System: Defective B and T sell Activation in CD100-Deficient Mice", Immunity, Nov. 2000, pp. 633-642, vol. 13, Cell Press, United States.

Shimada et al., "Isolation of Locally-derived Stem/Progenitor Cells From the Peri-infarct Area That Do Not Migrate From The Lateral Ventricle After Cortical Stroke", Stroke, Sep. 2010, pp. e552-e560, vol. 9 Issue 41.

Skolnick et al., "From Genes to Protein Structure and Function: Novel Applications of Computational Approaches in the Genomic Era", Trends in Biotechnology, Jan. 2000, pp. 34-39, vol. 18 No. 1, Elsevier Science Ltd., United States.

Smith et al., "SEMA4D Compromises Blood-Brain Barrier, Activates Microglia, and Inhibits Remyelination in Neurodegenerative Disease", Neurobiology of Disease, Jan. 2015, pp. 254-268, vol. 73, Elsevier Inc.

Southwell et al., "Anti-semaphorin 4D Immunotherapy Ameliorates Neuropathology and Some Cognitive Impairment in the YAC128 Mouse Model of Huntington Disease", Neurobiology of Disease, 2015, pp. 46-56, vol. 76.

Stamatovic et al., "Inflammation and brain edema: new insights into the role of chemokines and their receptors," Acta Neurochirurgica, 2006, 444-450, Supplement 96, Springer-Verlag, pp. Austria.

Steinman, "Multiple Sclerosis: A Two-Stage Disease", Nature Immunology, 2001, pp. 762-764, vol. 2 No. 9.

Suzuki et al., "Semaphorins and their Receptors in Immune Cell Interactions", Nature Immunology, Jan. 2008, pp. 17-23, vol. 9 No. 1, Nature Publishing Group, United States.

Swiercz et al., "ErbB-2 and Met Reciprocally Regulate Cellular Signaling via Plexin-B1", The Journal of Biological Chemistry, Jan. 2008, pp. 1893-1901, vol. 283 No. 4, The American Society for Biochemistry and Molecular Biology, Inc., United States.

(56) References Cited

OTHER PUBLICATIONS

Miller, John P., et al. "A Genome-Scale RNA-Interference Screen Identifies RRAS Signaling As a Pathologic Feature of Huntington's Disease", PLOS Genetics, 2012, vol. 8 (No. 11), e1003042, pp. 1-22.
ULM, Notice of Allowance and Notice of Allowibility issued in U.S. Appl. No. 14/519,965, 5 pages, dated Nov. 9, 2016.
Office Action for U.S. Appl. No. 14/519,965 dated Oct. 21, 2016.
Office Action for U.S. Appl. No. 14/519,965 dated May 10, 2016.
Suzumura, A., 2014. [Microglia in neurodegenerative disorders and neuroinflammation]. Rinsho Shinkeigaku 54, 1119-1121. https://doi.org/10.5692/clinicalneurol.54.1119 with English abstract.
Lin, C., et al., 2013, "Neurovascular abnormalities in humans and mice with Huntington's disease", Experimental Neurology 250: 20-30.
Stolp, H.B. et al., 2009, "Review: Role of developmental inflammation and blood-brain barrier dysfunction in neurodevelopmental an neurodegenerative diseases", Neuropathology and Applied Neurobiology, 35: 132-146.
Anonymous, "NCT01764737: Evaluation of Safety, Tolerability and PK of VX15/2503 in Patients with MS", Aug. 2, 2013, whole document, Retrieved from the Internet: URL:http://clinicaltrials.gov/archive/NCT01764737/2013_08_02 Retrieved on Apr. 25, 2017, 6 pages.

Alamed et al. *Nat. Protocols*, 2006

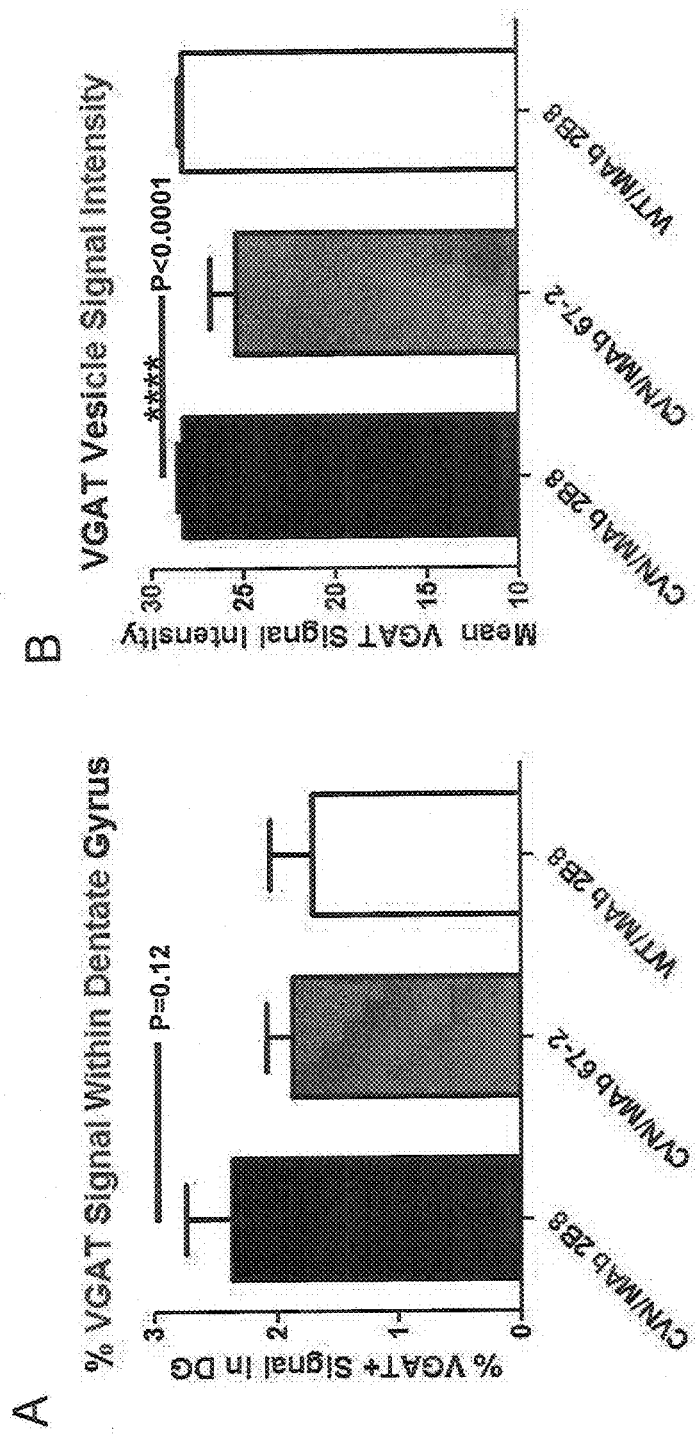
FIG. 4A,B

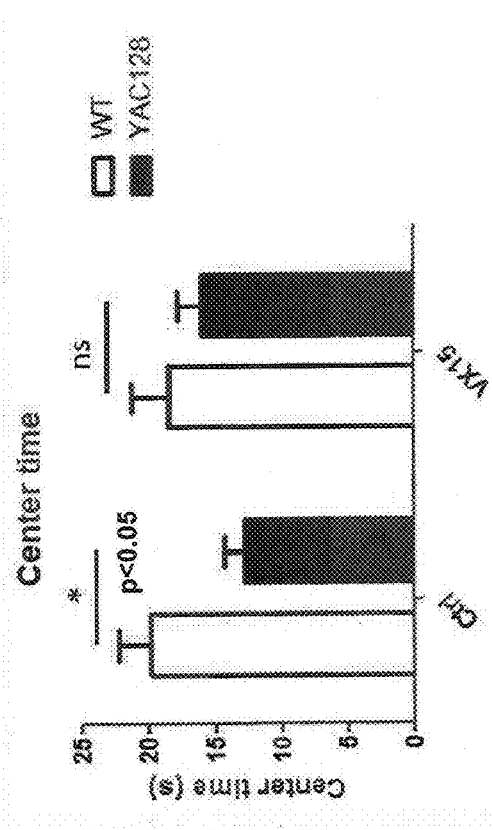
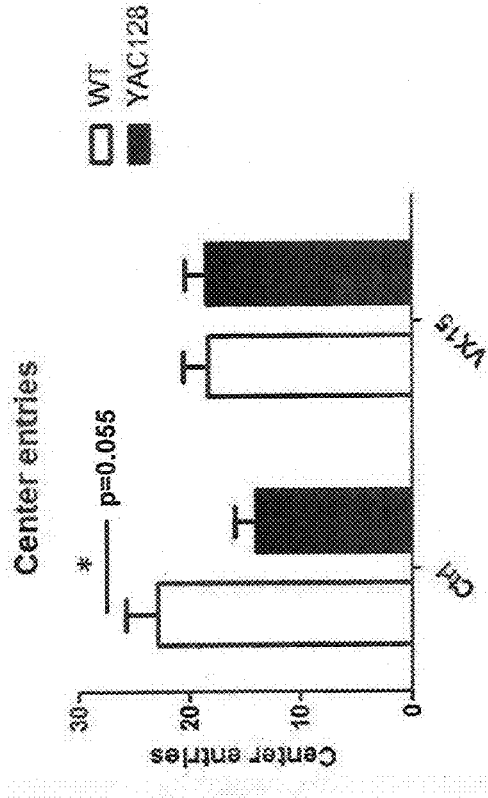
FIG. 5A
FIG. 5B

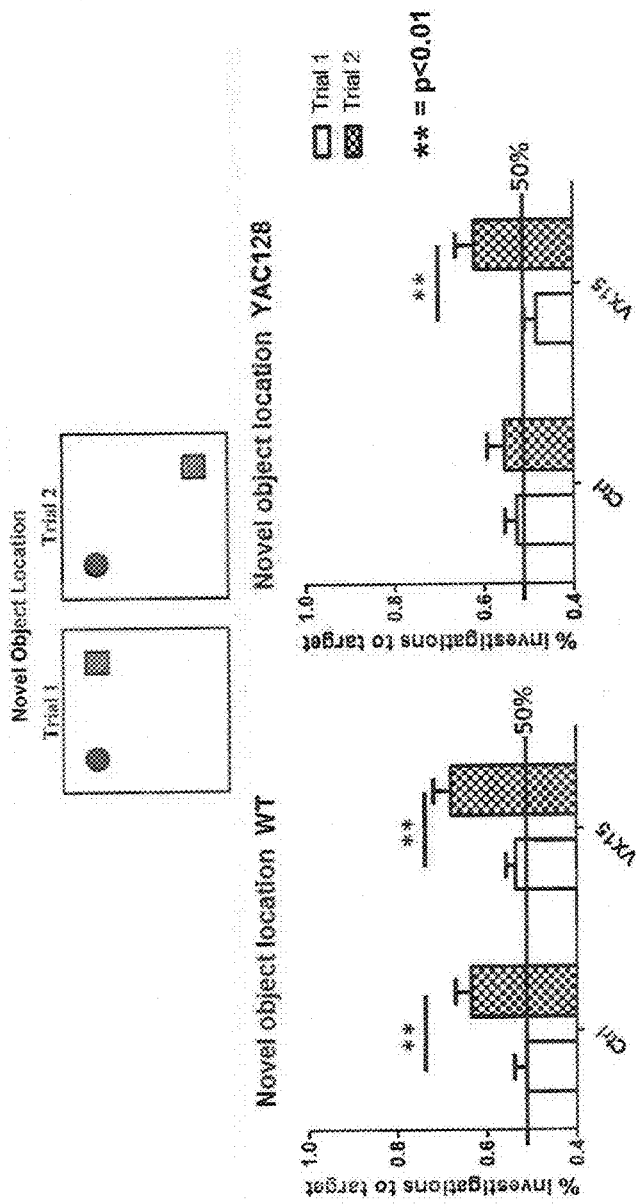

FIG. 9A,B,C,D,E,F,G,H,I,J,K,L,M,N,O,P

FIG. 15A,B,C,D

USE OF SEMAPHORIN-4D BINDING MOLECULES FOR TREATING NEURODEGENERATIVE DISORDERS

CROSS-REFERENCE TO RELATED APPLICATIONS

This application is a Continuation of and claims the benefit of both U.S. Non-Provisional patent application Ser. No. 15/420,662, filed on Jan. 31, 2017 and U.S. Non-Provisional patent application Ser. No. 14/519,965, filed on Oct. 21, 2014, now U.S. Pat. No. 9,598,495, issued Mar. 21, 2017, and also claims benefit to U.S. Provisional application No. 62/012,805, filed on Jun. 16, 2014, U.S. Provisional Appl. No. 61/979,384, filed on Apr. 14, 2014, and U.S. Provisional Appl. No. 61/893,814, filed on Oct. 21, 2013, the contents of which are each hereby incorporated by reference in their entireties.

REFERENCE TO SEQUENCE LISTING SUBMITTED ELECTRONICALLY

The content of the electronically submitted sequence listing in ASCII text file (Name 58008-163820seq-1stg_Div_ST25.txt; Size: 32,500 bytes; and Date of Creation: Mar. 1, 2017) filed with the application is incorporated herein by reference in its entirety.

BACKGROUND OF THE DISCLOSURE

Semaphorin 4D (SEMA4D), also known as CD100, is a transmembrane protein (e.g., SEQ ID NO: 1 (human); SEQ ID NO: 2 (murine)) that belongs to the semaphorin gene family. SEMA4D is expressed on the cell surface as a homodimer, but upon cell activation SEMA4D can be released from the cell surface via proteolytic cleavage to generate sSEMA4D, a soluble form of the protein, which is also biologically active. See Suzuki et al., *Nature Rev. Immunol.* 3:159-167 (2003); Kikutani et al., *Nature Immunol.* 9:17-23 (2008).

SEMA4D is expressed at high levels in lymphoid organs, including the spleen, thymus, and lymph nodes, and in non-lymphoid organs, such as the brain, heart, and kidney. In lymphoid organs, SEMA4D is abundantly expressed on resting T cells but only weakly expressed on resting B cells and antigen-presenting cells (APCs), such as dendritic cells (DCs). Its expression, however, is upregulated in these cells following activation by various immunological stimuli. The release of soluble SEMA4D from immune cells is also increased by cell activation.

SEMA4D has been implicated in the development of neurodegenerative disorders, autoimmune diseases, demyelinating diseases, and certain cancers. However, the effect of blocking SEMA4D signaling on the organization and function of the central nervous system (CNS) including brain and spinal cord and on behaviors controlled by the CNS remains to be elucidated. This is important because changes in the CNS have a profound influence on a subject's behavior and quality of life. In particular, such changes can impact a subject's neuropsychiatric behavior, cognitive behavior, and motor skills. There remains, therefore, a need for treatments for neurodegenerative disorders that alleviate the symptoms associated with the disorder.

BRIEF SUMMARY OF THE DISCLOSURE

Methods for using semaphorin 4D binding molecules to alleviate symptoms in a subject having neurodegenerative disorders are disclosed herein. According to aspects of the disclosure illustrated herein, there is provided a method for improving symptoms in a subject with a neurodegenerative disorder including administering to the subject an effective amount of an isolated binding molecule which specifically binds to semaphorin 4D (SEMA4D) and inhibits, suppresses, prevents, reverses or slows the effect of SEMA4D.

According to aspects illustrated herein, there is provided a method of treating a subject with a neurodegenerative disorder including administering to the subject an effective amount of an isolated binding molecule which specifically binds to semaphorin 4D (SEMA4D), wherein the binding to SEMA4D acts to improve symptoms associated with the disorder.

Methods of alleviating symptoms in a subject having a neurodegenerative disorder are provided, comprising administering to that subject an effective amount of an isolated binding molecule which specifically binds to semaphorin-4D (SEMA4D). In certain embodiments of the methods, the binding molecule inhibits SEMA4D interaction with its receptor or a portion of its receptor. In certain embodiments of the methods, the receptor is selected from the group consisting of Plexin-B1 and Plexin-B2. In certain embodiments of the methods, the binding molecule inhibits SEMA4D-mediated Plexin-B1 signal transduction. In certain embodiments of the methods, the isolated binding molecule specifically binds to the same SEMA4D epitope as a reference monoclonal antibody selected from the group consisting of VX15/2503 or 67. In certain embodiments of the methods, the isolated binding molecule competitively inhibits a reference monoclonal antibody selected from the group consisting of VX15/2503 or 67 from specifically binding to SEMA4D. In certain embodiments of the methods, the isolated binding molecule comprises an antibody or antigen-binding fragment thereof. In certain embodiments of the methods, the antibody or antigen-binding fragment thereof is monoclonal antibody VX15/2503 or 67. In certain embodiments of the methods, the antibody or antigen-binding fragment thereof comprises a variable heavy chain (VH) comprising VHCDRs 1-3 comprising SEQ ID NOs 6, 7, and 8, respectively, and a variable light chain (VL) comprising VLCDRs 1-3 comprising SEQ ID NOs 14, 15, and 16, respectively. In certain embodiments of the methods, the VH and VL comprise, respectively, SEQ ID NO: 9 and SEQ ID NO: 17 or SEQ ID NO: 10 and SEQ ID NO: 18. In certain embodiments of any of the aforementioned methods, the neurodegenerative disorder is selected from a group consisting of Alzheimer's disease, Parkinson's disease, Huntington's disease, Down syndrome, ataxia, amyotrophic lateral sclerosis (ALS), frontotemporal dementia (FTD), HIV-related cognitive impairment, CNS Lupus, mild cognitive impairment, or a combination thereof. In certain embodiments of any of the aforementioned methods, the neurodegenerative disorder is Alzheimer's disease or Huntington's disease. In certain embodiments of any one of the aforementioned methods, the symptoms are selected from a group consisting of neuropsychiatric symptoms, cognitive symptoms, motor dysfunction, and any combination thereof. In certain embodiments of any of the aforementioned methods, the neuropsychiatric symptoms are selected from a group consisting of reducing anxiety-like behavior, improving spatial memory, increasing locomotion, and any combination thereof.

Methods of alleviating symptoms in a subject having a neurodegenerative disorder are provided, comprising administering to that subject an effective amount of an isolated binding molecule which specifically binds to SEMA4D, wherein the binding molecule competitively inhibits a reference monoclonal antibody selected from the group consisting of VX15/2503 or 67 from specifically binding to SEMA4D. In certain embodiments of the methods, the binding molecule inhibits SEMA4D interaction with its receptor or a portion of its receptor. In certain embodiments of the methods, the receptor is selected from the group consisting of Plexin-B1 and Plexin-B2. In certain embodiments of the methods, the binding molecule inhibits SEMA4D-mediated Plexin-B1 signal transduction. In certain embodiments of the methods, the isolated binding molecule comprises an antibody or antigen-binding fragment thereof. In certain embodiments of the methods, the antibody or antigen-binding fragment thereof is monoclonal antibody VX15/2503 or 67. In certain embodiments of the methods, the antibody or antigen-binding fragment thereof comprises a variable heavy chain (VH) comprising VHCDRs 1-3 comprising SEQ ID NOs 6, 7, and 8, respectively, and a variable light chain (VL) comprising VLCDRs 1-3 comprising SEQ ID NOs 14, 15, and 16, respectively. In certain embodiments of the methods, the VH and VL comprise, respectively, SEQ ID NO: 9 and SEQ ID NO: 17 or SEQ ID NO: 10 and SEQ ID NO: 18. In certain embodiments of any of the aforementioned methods, the neurodegenerative disorder is selected from a group consisting of Alzheimer's disease, Parkinson's disease, Huntington's disease, Down syndrome, ataxia, amyotrophic lateral sclerosis (ALS), frontotemporal dementia (FTD), HIV-related cognitive impairment, CNS Lupus, mild cognitive impairment, or a combination thereof. In certain embodiments of any of the aforementioned methods, the neurodegenerative disorder is Alzheimer's disease or Huntington's disease. In certain embodiments of any one of the aforementioned methods, the symptoms are selected from a group consisting of neuropsychiatric symptoms, cognitive symptoms, motor dysfunction, and any combination thereof. In certain embodiments of any of the aforementioned methods, the neuropsychiatric symptoms are selected from a group consisting of reducing anxiety-like behavior, improving spatial memory, increasing locomotion, and any combination thereof Additional methods of treating a subject having a neurodegenerative or neuroinflammatory disorder, or of effecting a desirable outcome in a subject having a neurodegenerative or neuroinflammatory disorder, are provided herein. Methods of treating a subject having a neurodegenerative disorder are provided, comprising administering to the subject an effective amount of an isolated binding molecule which specifically binds to semaphorin-4D (SEMA4D), wherein the binding to SEMA4D acts to alleviate symptoms associated with the disorder. Methods of promoting myelination in a subject having a neurodegenerative disorder are provided, comprising administering to that subject an effective amount of an isolated binding molecule which specifically binds to SEMA4D, wherein the binding molecule modulates astrocyte-mediated activity of oligodendrocyte-myelin function. Methods of preventing neural cell death in a subject having a neurodegenerative disorder are provided, comprising administering to that subject an effective amount of an isolated binding molecule which specifically binds to SEMA4D, wherein the binding molecule modulates astrocyte-mediated synaptic activity. Methods of preventing injury to the blood-brain barrier in a subject having a neuroinflammatory or neurodegenerative disorder are provided, comprising administering to that subject an effective amount of an isolated binding molecule which specifically binds to SEMA4D, wherein the binding molecule modulates astrocyte-mediated maintenance of the integrity of the blood-brain barrier. Methods of preventing astrocyte activation in a subject having, determined to have, or suspected of having a neuroinflammatory or neurodegenerative disorder are provided, comprising administering to that subject an effective amount of an isolated binding molecule which specifically binds to SEMA4D, wherein the binding molecule modulates astrocyte-mediated maintenance of the integrity of the blood-brain barrier. Methods of maintaining or restoring astrocyte-mediated trophic support of oligodendrocyte precursor cells (OPCs) in a subject having, determined to have, or suspected of having a neuroinflammatory or neurodegenerative disorder are provided, comprising administering to that subject an effective amount of an isolated binding molecule which specifically binds to SEMA4D, wherein the binding molecule prevents retraction of astrocyte processes and chemotactic movement of OPCs toward regions of damage. Methods of protecting inhibitory neurons from degeneration in early Alzheimer's disease are provided, comprising administering to a subject having, determined to have, or suspected of having early Alzheimer's disease an effective amount of an isolated binding molecule which specifically binds to SEMA4D, wherein the binding molecule restores the number of somatostatin positive neurons, NYP-positive neurons, or both in the subject. In certain embodiments of the aforementioned methods, the binding molecule inhibits SEMA4D interaction with its receptor or a portion of its receptor. In certain embodiments of the aforementioned methods, the receptor is selected from the group consisting of Plexin-B1 and Plexin-B2. In certain embodiments of the aforementioned methods, the binding molecule inhibits SEMA4D-mediated Plexin-B1 signal transduction. In certain embodiments of the aforementioned methods, the isolated binding molecule specifically binds to the same SEMA4D epitope as a reference monoclonal antibody selected from the group consisting of VX15/2503 or 67. In certain embodiments of the aforementioned methods, the isolated binding molecule competitively inhibits a reference monoclonal antibody selected from the group consisting of VX15/2503 or 67 from specifically binding to SEMA4D. In certain embodiments of the aforementioned methods, the isolated binding molecule comprises an antibody or antigen-binding fragment thereof. In certain embodiments of the aforementioned methods, the antibody or antigen-binding fragment thereof is monoclonal antibody VX15/2503 or 67. In certain embodiments of the aforementioned methods, the antibody or antigen-binding fragment thereof comprises a variable heavy chain (VH) comprising VHCDRs 1-3 comprising SEQ ID NOs 6, 7, and 8, respectively, and a variable light chain (VL) comprising VLCDRs 1-3 comprising SEQ ID NOs 14, 15, and 16, respectively. In certain embodiments of the aforementioned methods, the VH and VL comprise, respectively, SEQ ID NO: 9 and SEQ ID NO: 17 or SEQ ID NO: 10 and SEQ ID NO: 18. In certain embodiments of the aforementioned methods, the neurodegenerative disorder is selected from a group consisting of Alzheimer's disease, Parkinson's disease, Huntington's disease, Down syndrome, ataxia, amyotrophic lateral sclerosis (ALS), frontotemporal dementia (FTD), HIV-related cognitive impairment, CNS Lupus, mild cognitive impairment, or a combination thereof. In certain embodiments of the aforementioned methods, the neurodegenerative disorder is Alzheimer's disease or Huntington's disease. In certain embodiments of the aforementioned methods, symptoms of the subject that are alleviated by the methods are selected from a group consisting of neuropsychiatric symptoms, cognitive symptoms, motor dysfunction, and any combination thereof. In certain embodiments of the aforementioned methods, the neuropsychiatric symptoms of the subject that are alleviated by the methods are selected from a group consisting of reducing anxiety-like behavior, improving spatial memory, increasing locomotion, and any combination thereof. In certain embodiments of the aforementioned methods, the subject is determined to have the neurodegenerative disorder by processing a sample or image from the subject.

BRIEF DESCRIPTION OF THE DRAWINGS/FIGURES

FIG. 1: Schematic of experimental protocol described in the Examples.

Figures 2A, 2B:
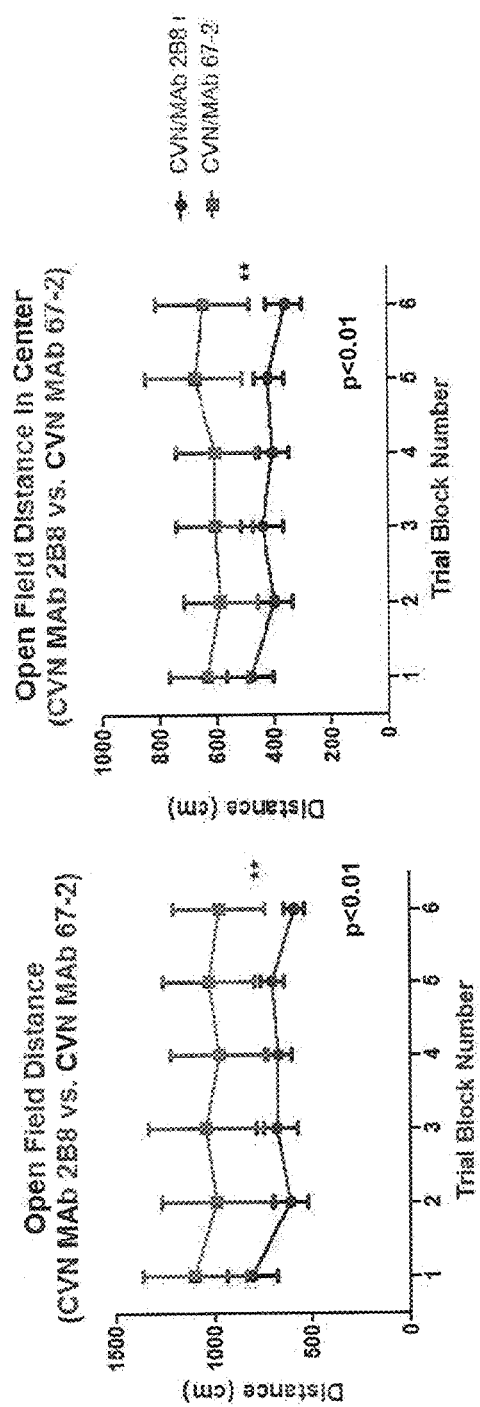

FIG. 2A: In vivo CVN model measuring anxiety-like behavior in CVN mice treated with anti-SEMA4D antibody ("MAb 67") or control isotype ("MAb 2B8"), total locomotion.

FIG. 2B: In vivo CVN model measuring anxiety-like behavior in CVN mice treated with anti-SEMA4D antibody ("MAb 67") or control isotype ("MAb 2B8"), locomotion in the center of the open field.

Figure 3B:
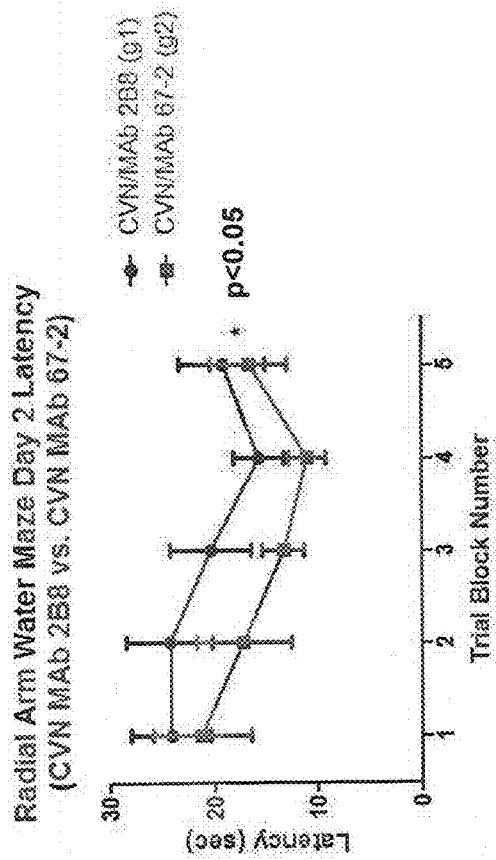
Figure 3A:
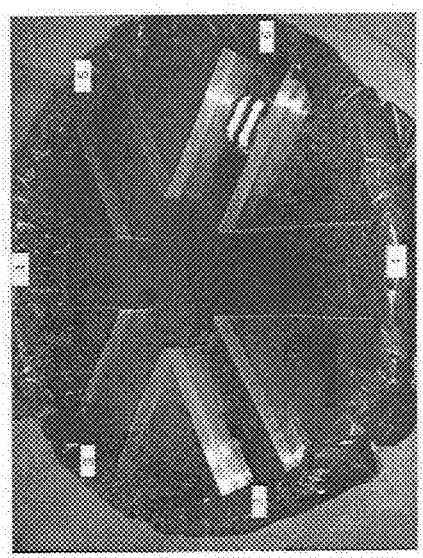

FIG. 3A: a photograph of a redial-arm water maze.

FIG. 3B: In vivo CVN model measuring spatial memory in a radial-arm water maze, CVN mice treated with anti-SEMA4D antibody ("MAb 67") or control isotype.

FIG. 4A: In vivo CVN model measuring the density of GABAergic synapses and concentration of vesicular GABA transporter (VGAT) in CVN mice treated with anti-SEMA4D antibody ("MAb 67") or control isotype, graph showing VGAT positive vesicles.

FIG. 4B: In vivo CVN model measuring the density of GABAergic synapses and concentration of vesicular GABA transporter (VGAT) in CVN mice treated with anti-SEMA4D antibody ("MAb 67") or control isotype, graph showing VGAT staining intensity level per vesicle.

FIG. 5A: In vivo YAC128 model measuring anxiety-like behavior in mice treated with anti-SEMA4D antibody ("MAb 67") and control isotype, graph showing entries into field.

FIG. 5B: In vivo YAC128 model measuring anxiety-like behavior in mice treated with anti-SEMA4D antibody ("MAb 67") and control isotype, graph showing time spent in the center of the field.

FIG. 6A: In vivo YAC128 model measuring spatial memory in mice treated with anti-SEMA4D antibody ("MAb 67") and control isotype, Trial 1.

FIG. 6B: In vivo YAC128 model measuring spatial memory in mice treated with anti-SEMA4D antibody ("MAb 67") and control isotype, Trial 2.

Figures 7A, 7B:
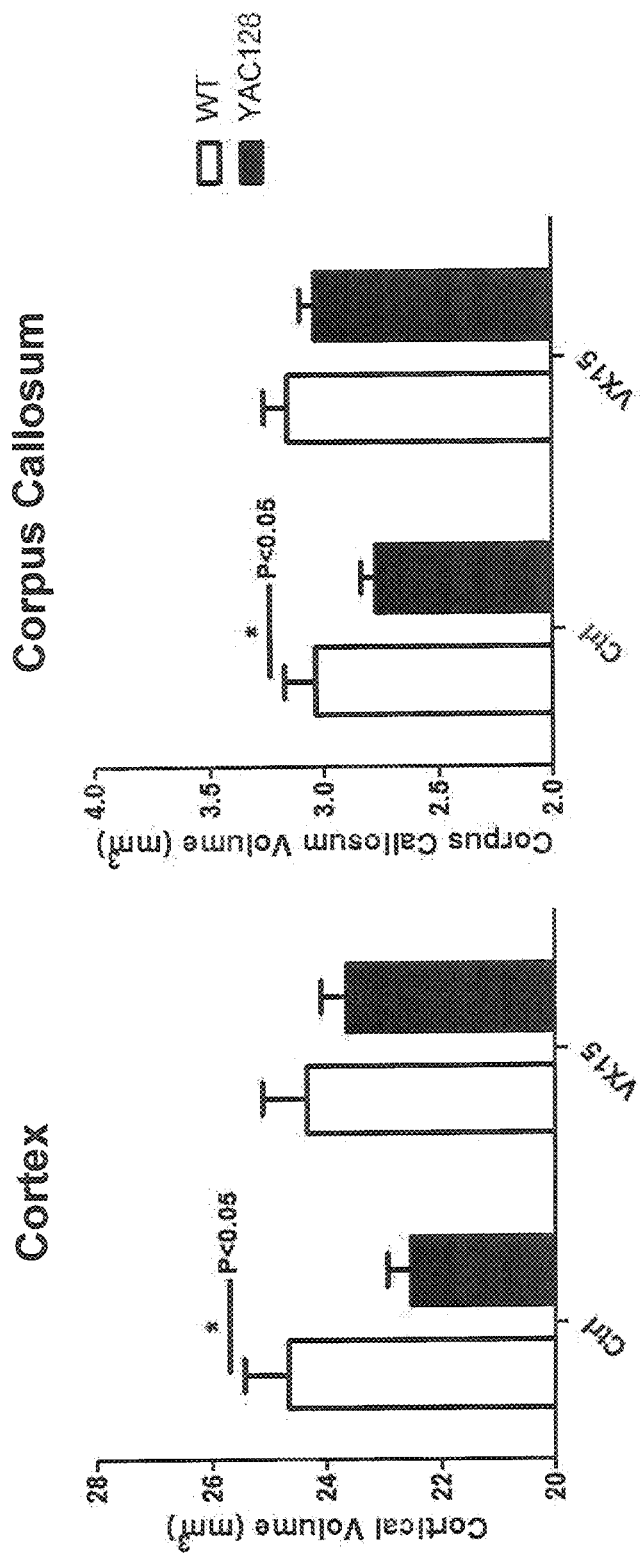

FIG. 7A: In vivo YAC128 model measuring cortical volume in mice treated with anti-SEMA4D antibody ("MAb 67") or control isotype.

FIG. 7B: In vivo YAC128 model measuring corpus callosum volume in mice treated with anti-SEMA4D antibody ("MAb 67") or control isotype.

Figure 8:
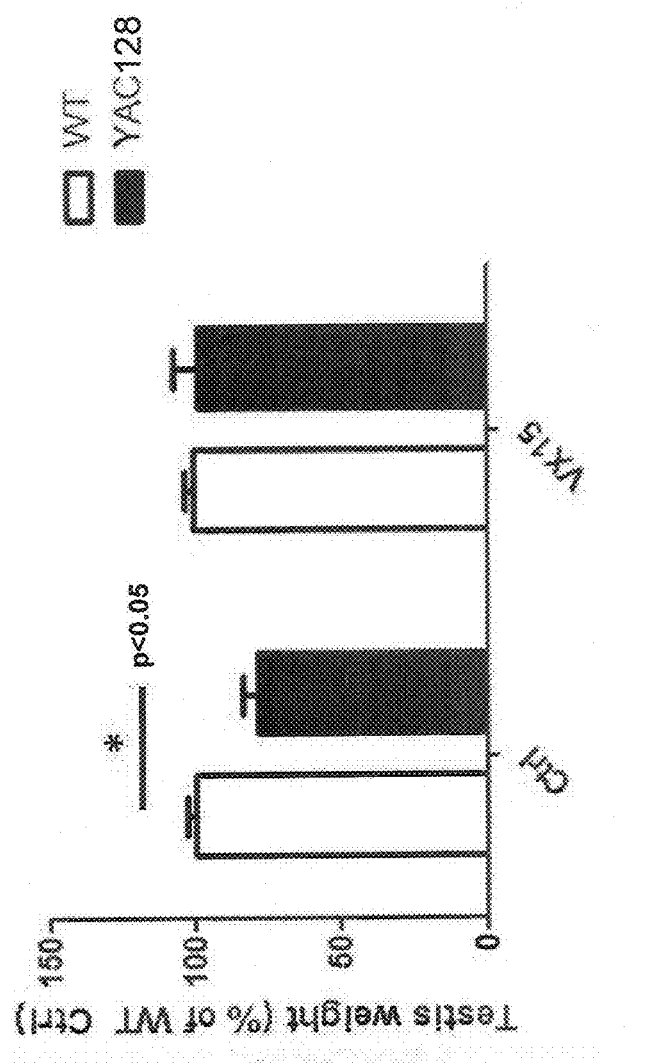

FIG. 8: In vivo YAC128 model measuring testicular degeneration in mice treated with anti-SEMA4D antibody ("MAb 67") or control isotype.

Figure 9:

FIG. 9A-P: Immunohistochemical analysis of cell types expressing SEMA4D, plexin-B1, and CD72 in normal rat spinal cord.

FIG. 9B: Nkx2.2 is an oligodendrocyte precursor cell marker.

FIG. 9G: glial fibrillary acid protein (GFAP) is an astrocytic cell marker.

FIG. 9N: Iba1 (panel N) is a microglial cell marker. FIGS. 9A, 9E, 9I, and 9M show merged images, and FIGS. 9D, 9H, 9L, and 9P, show the same sections stained with DAPI to visualize cellular nuclei.

Figure 10:
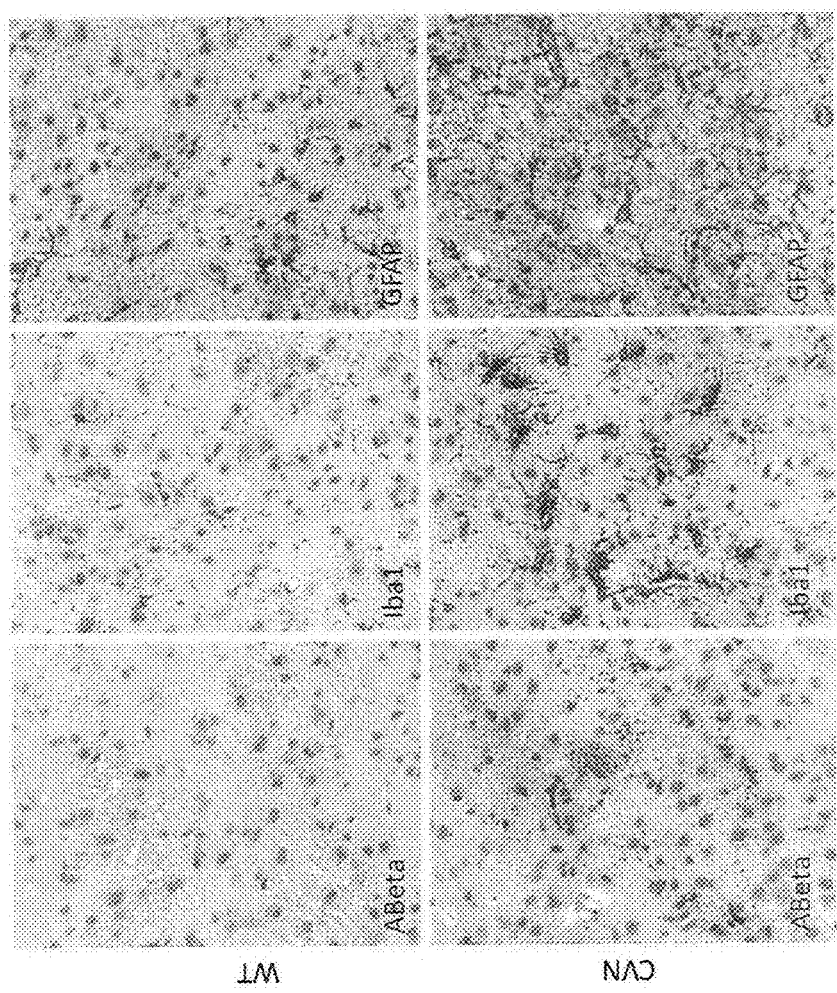

FIG. 10: DAB immunohistochemical analysis of amyloid pathology and glial activation in normal (top three panels) and CVN (bottom three panels) mice. Subiculum sections were stained for amyloid-beta 1-42 (left panels), the microglial cell marker Iba1 (middle panels) and the astrocytic cell marker GFAP.

Figure 11A:
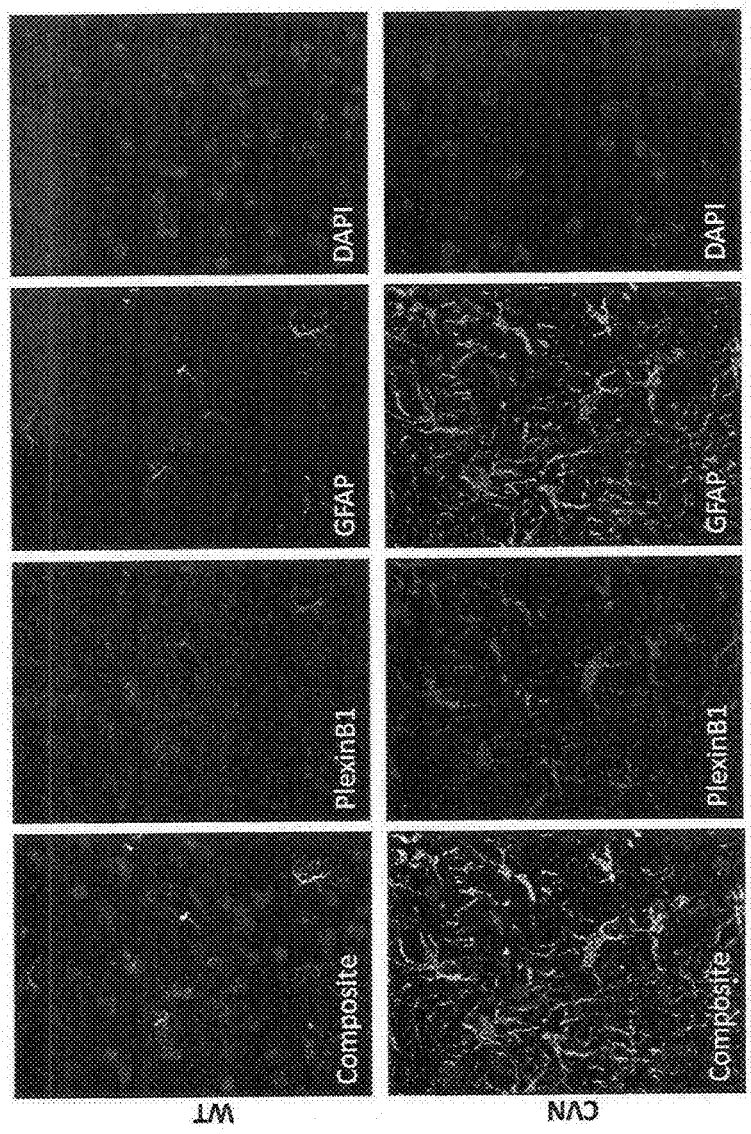

FIG. 11A: Characterization and expression patterns of plexin-B1 and plexin-B2 receptors in the CVN Alzheimer's disease mouse model, showing immunohistochemical analysis of plexin-B1 expression in normal (top panels) and CVN (bottom panels) mice. Brain sections were stained for plexin-B1, and GFAP, as well as DAPI to visualize cellular nuclei.

Figure 11B:
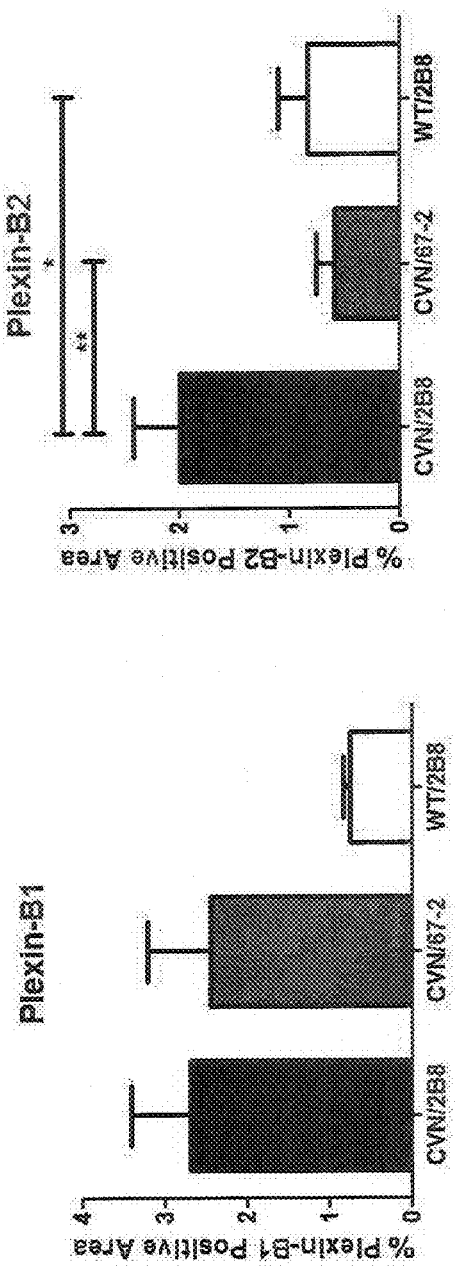

FIG. 11B: Characterization and expression patterns of plexin-B1 and plexin-B2 receptors in the CVN Alzheimer's disease mouse model, showing expression levels of plexin-B1 (left graph) and plexin-B2 (right graph) following inhibition of SEMA4D signaling.

Figure 12:
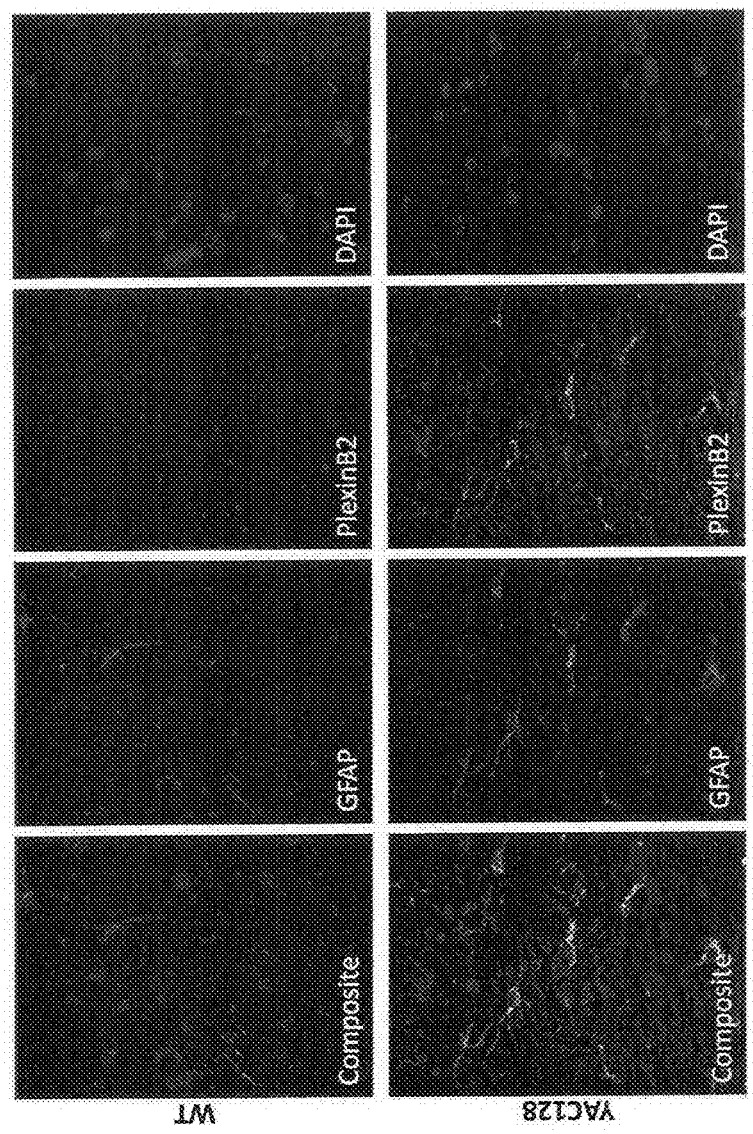

FIG. 12: Immunohistochemical analysis of plexin-B2 expression in normal (top panels) and YAC128 (bottom panels) mice. Brain sections were stained for plexin-B2, and GFAP, as well as DAPI to visualize cellular nuclei.

Figure 13:
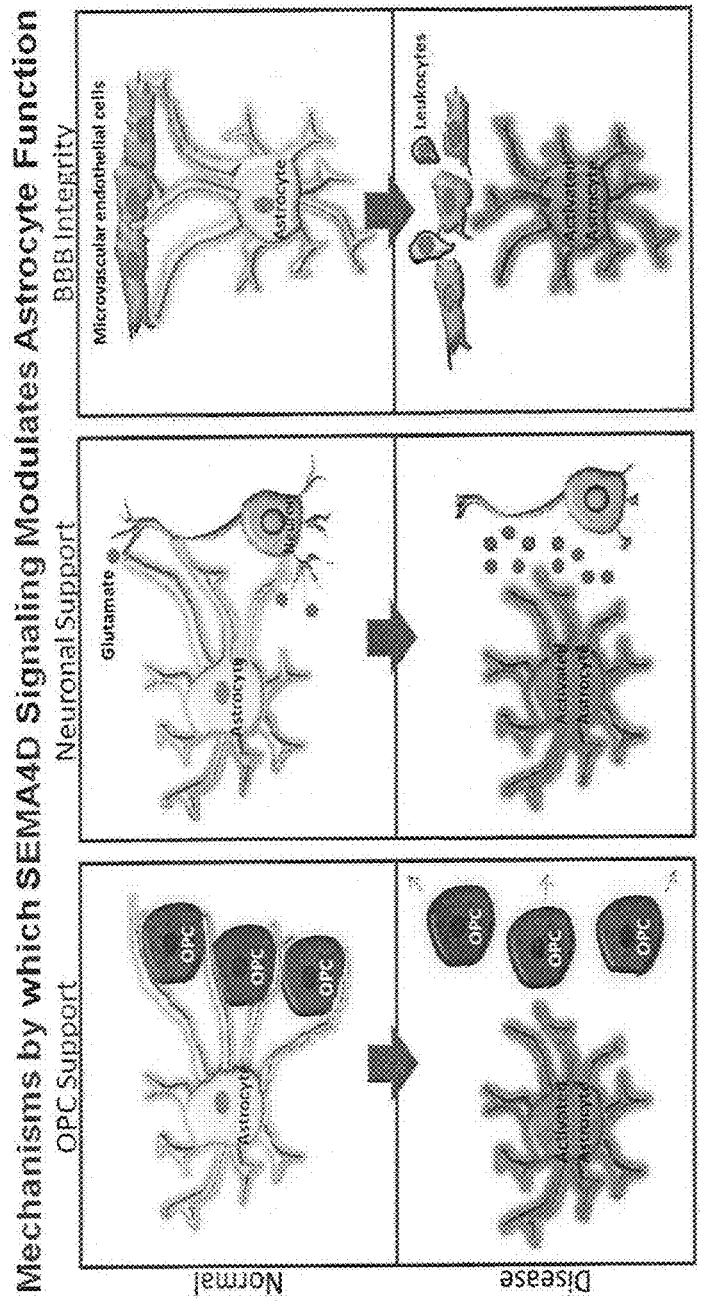

FIG. 13: Schematic representation of the roles SEMA4D signaling can play in the regulation of astrocyte function in health and disease. Left Panel: Plexin+ (shaded region of astrocyte exterior surface) astrocytic processes interdigitate between SEMA4D+ NIKX2.2+ oligodendrocyte precursor cells (OPCs) and provide trophic support (SEMA4D+ shown as shaded region of OPC exterior surface). In CNS disease, activated astrocytes upregulate Plexin expression and retract processes via SEMA4D signaling. Locally, this results in diminished trophic support and increased chemotaxis-driven OPC movement toward regions of damage, while lack of astrocytic support at lesion site impedes remyelination. Center Panel: In CNS disease, astrocytic activation leads to upregulation of Plexin (shaded region of astrocyte exterior surface) expression, increased SEMA4D signaling and process retraction, which results in a loss of neuronal axon guidance, decreased trophic support, and/or dysregulated glutamate uptake/release. Ultimately, depending upon severity of disease stimulus, synapse loss and subsequent excitotoxic neuron death can occur. Right Panel: CNS disease-induced astrocyte activation increases SEMA4D signaling through Plexin (shaded region of astrocyte exterior surface), which leads to a retraction of astrocytic foot processes as evidenced by redistribution of aquaporin-4. This results in dysregulation and permeability of the BBB, thereby facilitating endothelial inflammation and subsequent leukocyte entry into the CNS.

Figure 14:
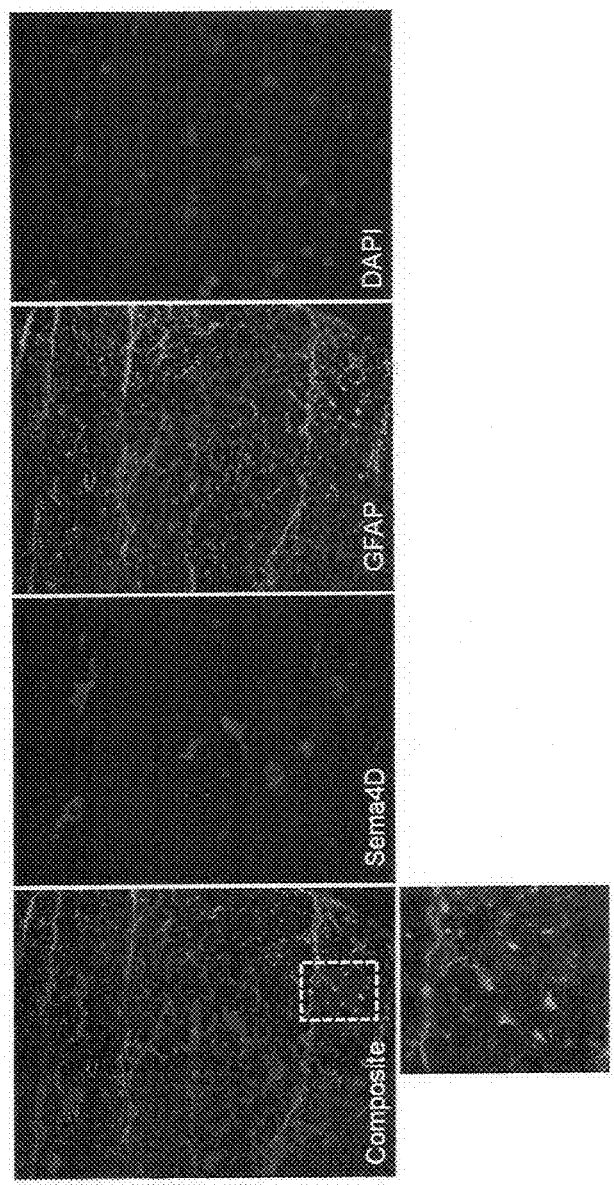

FIG. 14: Immunohistochemical analysis showing SEMA4D-expressing OPCs oriented in close association with GFAP+ astrocytic processes in normal rats. Brain sections were stained for SEMA4D (OPCs), and GFAP (astrocytes), as well as DAPI to visualize cellular nuclei.

FIG. 15A: In vivo CVN model measuring somatostatin-positive signaling within the subiculum or dentate gyrus in CVN mice treated with anti-SEMA4D antibody ("MAb 67") or control isotype. Error bars indicate standard error. "*"=$p<0.05$ and "***"=$p<0.005$ by 1-way ANOVA with Bonferroni's Multiple Comparison Test.

FIG. 15B: In vivo CVN model measuring neuropeptide-Y (NPY)-positive signaling within the subiculum or dentate gyrus, respectively, in CVN mice treated with anti- SEMA4D antibody ("MAb 67") or control isotype. Error bars indicate standard error. "*"=p<0.05 and "***"=p<0.005 by 1-way ANOVA with Bonferroni's Multiple Comparison Test.

FIG. 15C: In vivo CVN model measuring NPY receptor 1 (NPY1R) positive signaling within the subiculum or dentate gyrus in CVN mice treated with anti-SEMA4D antibody ("MAb 67") or control isotype. Error bars indicate standard error. "*"=p<0.05 and "***"=p<0.005 by 1-way ANOVA with Bonferroni's Multiple Comparison Test.

FIG. 15D: In vivo CVN model measuring NPY receptor 2 (NPY2R) (panel D) positive signaling within the subiculum or dentate gyrus in CVN mice treated with anti-SEMA4D antibody ("MAb 67") or control isotype. Error bars indicate standard error. "*"=p<0.05 and "***"=p<0.005 by 1-way ANOVA with Bonferroni's Multiple Comparison Test.

Figure 16:
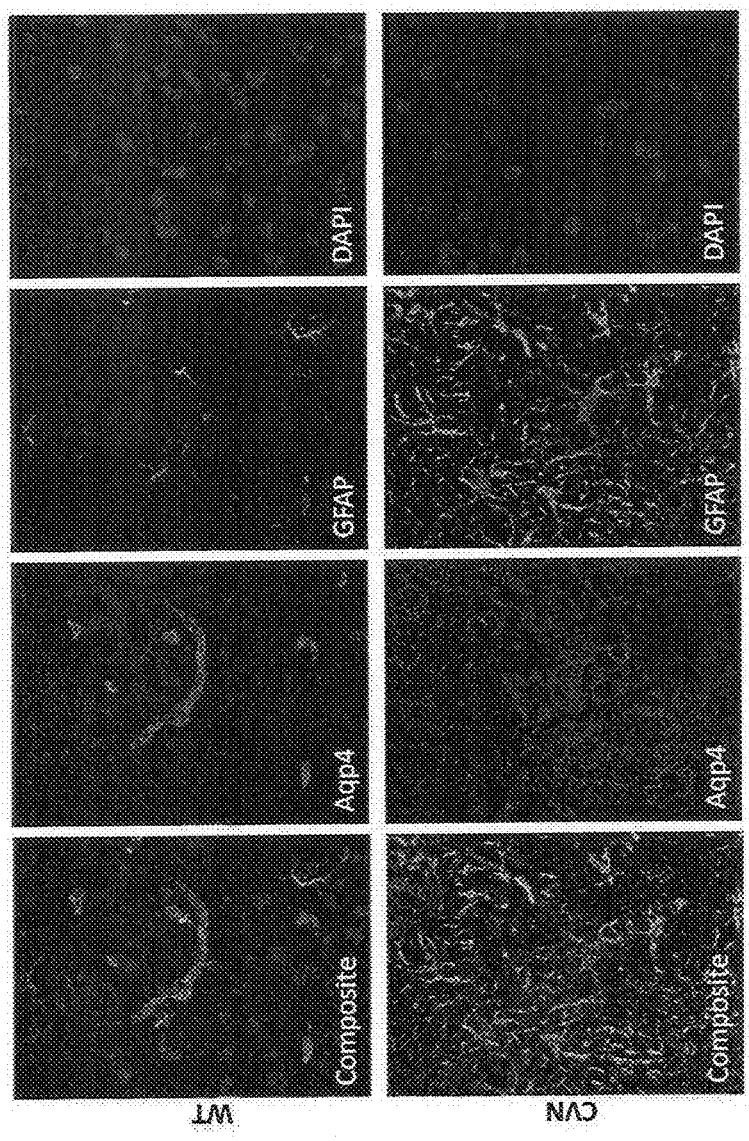

FIG. 16: Immunohistochemical analysis of aquaporin-4 expression patterns in normal and CVN mice.

Figure 17:
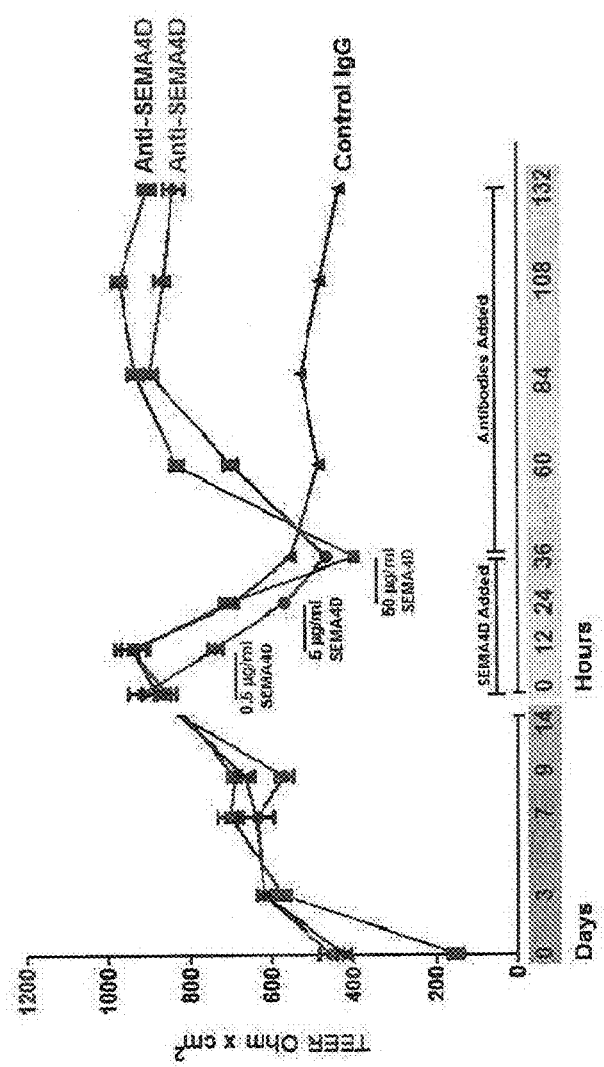

FIG. 17: In vitro DIV-BBB model measuring integrity of the blood-brain barrier upon addition of anti-SEMA4D monoclonal antibody VX15/2503.

Figure 18A:
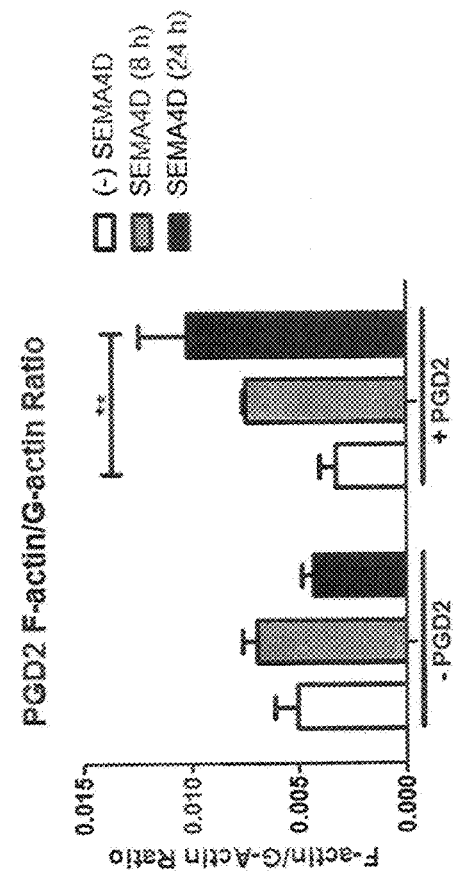

FIG. 18A: Immunocytochemical analysis showing astrocyte activation in rat astrocytes, showing immunocytochemical analysis of astrocyte activation as reflected in the relative increase in GFAP positive area in cultured rat astrocytes treated with SEMA4D in isolation or following pretreatment with thioacetamide (TAA). "*"=P<0.05 by one-way ANOVA with Bonferroni's Multiple Comparison Test.

Figure 18B:
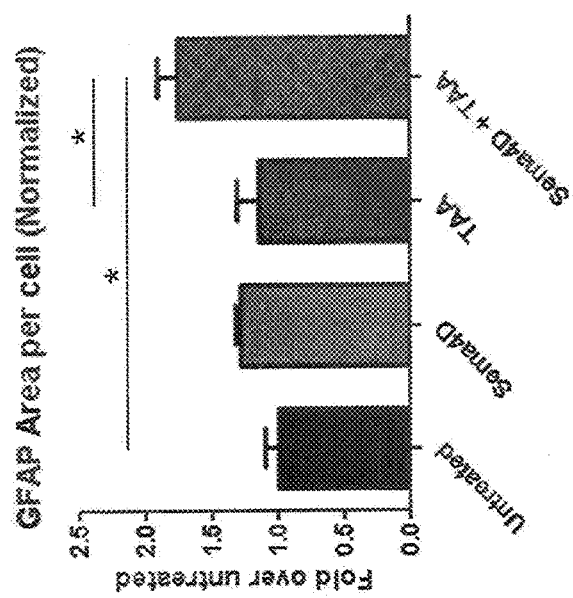

FIG. 18B: Immunocytochemical analysis showing astrocyte activation in rat astrocytes, showing immunocytochemical analysis of astrocyte activation as reflected in the ratio of F-actin to G-actin in cultured rat astrocytes treated with SEMA4D in isolation or in combination with prostaglandin D2. Error bars represent standard deviation. "*"=P<0.05 by one-way ANOVA with Bonferroni's Multiple Comparison Test.

DETAILED DESCRIPTION OF THE DISCLOSURE

I. Definitions

It is to be noted that the term "a" or "an" entity refers to one or more of that entity; for example, "an anti-SEMA4D antibody" is understood to represent one or more anti-SEMA4D antibodies. As such, the terms "a" (or "an"), "one or more," and "at least one" can be used interchangeably herein.

Furthermore, "and/or" where used herein is to be taken as specific disclosure of each of the two specified features or components with or without the other. Thus, the term and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

Unless defined otherwise, technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, provide one of skill with a general dictionary of many of the terms used in this disclosure.

Units, prefixes, and symbols are denoted in their Systeme International de Unites (SI) accepted form. Numeric ranges are inclusive of the numbers defining the range. Unless otherwise indicated, amino acid sequences are written left to right in amino to carboxy orientation. The headings provided herein are not limitations of the various aspects or aspects of the disclosure, which can be had by reference to the specification as a whole. Accordingly, the terms defined immediately below are more fully defined by reference to the specification in its entirety.

As used herein, the term "non-naturally occurring" substance, composition, entity, and/or any combination of substances, compositions, or entities, or any grammatical variants thereof, is a conditional term that explicitly excludes, but only excludes, those forms of the substance, composition, entity, and/or any combination of substances, compositions, or entities that are well-understood by persons of ordinary skill in the art as being "naturally-occurring," or that are, or might be at any time, determined or interpreted by a judge or an administrative or judicial body to be, "naturally-occurring."

As used herein, the term "neurodegenerative disorder" or "neurodegenerative disease" refers to a central nervous system (CNS) disorder that is characterized by the death of neurons in one or more regions of the nervous system and the subsequent functional impairment of the affected parties. Examples of neurodegenerative disorders include, without limitation, Alzheimer's disease, Parkinson's disease, Huntington's disease, Down syndrome, ataxia, amyotrophic lateral sclerosis (ALS), frontotemporal dementia (FTD), HIV-related cognitive impairment (HAND, HIV-Associated Neurocognitive Disorder), CNS Lupus and mild cognitive impairment. Neurodegenerative diseases have an enormous impact on the lives of affected individuals and their families as well as society as a whole.

As used herein, the term "Alzheimer's disease" refers to a progressive disease initially manifesting itself with partial amnesia, and later restlessness, disorientation, aphasia, agnosia or apraxia (cognitive decline), dementia and sometimes euphoria or depressions. The disease typically starts at 40 to 90 years of age and predominantly affects females. As to its prevalence, estimations are about 13% of the population above 65 years age.

As used herein, the term "Huntington's Disease" refers to a neurodegenerative disease, which is due to expansion of a poly-glutamine tract at the N-terminus of the protein huntingtin (expressed by the HTT gene) where the expansion can be more than 35-40 repetitions of the amino acid glutamine in the mutated protein (mHTT). The disease presents with progressive neuronal death in different brain areas, including toxicity in medium-sized spiny neurons of the striatum that determines the appearance of the classic motor incoordination and movements such as "Chorea". The mechanism of action of mHTT has been described as both gain and loss of function compared with the wild-type protein and involves the acquisition or loss of competence to interact with various proteins in different cellular compartments.

The term "therapeutically effective amount" refers to an amount of an antibody, polypeptide, polynucleotide, small organic molecule, or other drug effective to "treat" a disease or disorder in a subject or mammal. In the case of a neurodegenerative disorder, the therapeutically effective amount of the drug can alleviate symptoms of the disorder; decrease, reduce, retard or stop the incidence of symptoms; decrease, reduce, retard the severity of symptoms; inhibit, e.g., suppress, retard, prevent, stop, or reverse the manifestation of symptoms; relieve to some extent one or more of the symptoms associated with the disorder; reduce morbidity and mortality; improve quality of life; or a combination of such effects.

The term "symptoms" as referred to herein refer to, e.g., 1) neuropsychiatric symptoms, 2) cognitive symptoms, and 3) motor dysfunction. Examples of neuropsychiatric symptoms include, for instance, anxiety-like behavior. Examples of cognitive symptoms include, for instance, learning and memory deficits. Examples of motor dysfunction include, for instance, locomotion.

Terms such as "treating" or "treatment" or "to treat" or "alleviating" or "to alleviate" or "improving" or "to improve" refer to both 1) therapeutic measures that cure, slow down, lessen symptoms of, reverse, and/or halt progression of a diagnosed pathologic condition or disorder and 2) prophylactic or preventative measures that prevent and/or slow the development of a targeted pathologic condition or disorder. Thus those in need of treatment include those already with the disorder; those prone to have the disorder; and those in whom the disorder is to be prevented. Beneficial or desired clinical results include, but are not limited to, alleviation of symptoms, diminishment of extent of disease, stabilization (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

By "subject" or "individual" or "animal" or "patient" or "mammal," is meant any subject, particularly a mammalian subject, for whom diagnosis, prognosis, or therapy is desired. Mammalian subjects include humans, domestic animals, farm animals, and zoo, sports, or pet animals such as dogs, cats, guinea pigs, rabbits, rats, mice, horses, cattle, cows, bears, and so on.

As used herein, phrases such as "a subject that would benefit from administration of an anti-SEMA4D antibody" and "an animal in need of treatment" includes subjects, such as mammalian subjects, that would benefit from administration of an anti-SEMA4D antibody or other SEMA4D binding molecule used, e.g., for detection of a SEMA4D polypeptide (e.g., for a diagnostic procedure) and/or from treatment, i.e., palliation or prevention of a disease, with an anti-SEMA4D antibody or other SEMA4D binding molecule.

A "binding molecule" or "antigen binding molecule" of the present disclosure refers in its broadest sense to a molecule that specifically binds an antigenic determinant. In one embodiment, the binding molecule specifically binds to SEMA4D, e.g., to a transmembrane SEMA4D polypeptide of about 150 kDa or a soluble SEMA4D polypeptide of about 120 kDa (commonly referred to as sSEMA4D). In another embodiment, a binding molecule of the disclosure is an antibody or an antigen binding fragment thereof. In another embodiment, a binding molecule of the disclosure comprises at least one heavy or light chain CDR of an antibody molecule. In another embodiment, a binding molecule of the disclosure comprises at least two CDRs from one or more antibody molecules. In another embodiment, a binding molecule of the disclosure comprises at least three CDRs from one or more antibody molecules. In another embodiment, a binding molecule of the disclosure comprises at least four CDRs from one or more antibody molecules. In another embodiment, a binding molecule of the disclosure comprises at least five CDRs from one or more antibody molecules. In another embodiment, a binding molecule of the disclosure comprises at least six CDRs from one or more antibody molecules.

The present disclosure is directed to a method of alleviating symptoms in a subject having a neurodegenerative disorder, comprising administering to the subject an anti-SEMA4D binding molecule, e.g., an antibody, or antigen-binding fragment, variant, or derivative thereof. Unless specifically referring to full-sized antibodies such as naturally occurring antibodies, the term "anti-SEMA4D antibody" encompasses full-sized antibodies as well as antigen-binding fragments, variants, analogs, or derivatives of such antibodies, e.g., naturally occurring antibody or immunoglobulin molecules or engineered antibody molecules or fragments that bind antigen in a manner similar to antibody molecules.

As used herein, "human" or "fully human" antibodies include antibodies having the amino acid sequence of a human immunoglobulin and include antibodies isolated from human immunoglobulin libraries or from animals transgenic for one or more human immunoglobulins and that do not express endogenous immunoglobulins, as described infra and, for example, in U.S. Pat. No. 5,939,598 by Kucherlapati et al. "Human" or "fully human" antibodies also include antibodies comprising at least the variable domain of a heavy chain, or at least the variable domains of a heavy chain and a light chain, where the variable domain(s) have the amino acid sequence of human immunoglobulin variable domain(s).

"Human" or "fully human" antibodies also include "human" or "fully human" antibodies, as described above, that comprise, consist essentially of, or consist of, variants (including derivatives) of antibody molecules (e.g., the VH regions and/or VL regions) described herein, which antibodies or fragments thereof immunospecifically bind to a SEMA4D polypeptide or fragment or variant thereof. Standard techniques known to those of skill in the art can be used to introduce mutations in the nucleotide sequence encoding a human anti-SEMA4D antibody, including, but not limited to, site-directed mutagenesis and PCR-mediated mutagenesis which result in amino acid substitutions. In some embodiments, the variants (including derivatives) encode less than 50 amino acid substitutions, less than 40 amino acid substitutions, less than 30 amino acid substitutions, less than 25 amino acid substitutions, less than 20 amino acid substitutions, less than 15 amino acid substitutions, less than 10 amino acid substitutions, less than 5 amino acid substitutions, less than 4 amino acid substitutions, less than 3 amino acid substitutions, or less than 2 amino acid substitutions relative to the reference VH region, VHCDR1, VHCDR2, VHCDR3, VL region, VLCDR1, VLCDR2, or VLCDR3.

In certain embodiments, the amino acid substitutions are conservative amino acid substitutions, discussed further below. Alternatively, mutations can be introduced randomly along all or part of the coding sequence, such as by saturation mutagenesis, and the resultant mutants can be screened for biological activity to identify mutants that retain activity (e.g., the ability to bind a SEMA4D polypeptide, e.g., human, murine, or both human and murine SEMA4D). Such variants (or derivatives thereof) of "human" or "fully human" antibodies can also be referred to as human or fully human antibodies that are "optimized" or "optimized for antigen binding" and include antibodies that have improved affinity to antigen.

The terms "antibody" and "immunoglobulin" are used interchangeably herein. An antibody or immunoglobulin comprises at least the variable domain of a heavy chain, and normally comprises at least the variable domains of a heavy chain and a light chain. Basic immunoglobulin structures in vertebrate systems are relatively well understood. See, e.g., Harlow et al. (1988) Antibodies: A Laboratory Manual (2nd ed.; Cold Spring Harbor Laboratory Press).

As used herein, the term "immunoglobulin" comprises various broad classes of polypeptides that can be distinguished biochemically. Those skilled in the art will appreciate that heavy chains are classified as gamma, mu, alpha, delta, or epsilon, (γ, μ, α, δ, ε) with some subclasses among them (e.g., γ1-γ4 γ4. γ4). It is the nature of this chain that determines the "class" of the antibody as IgG, IgM, IgA IgG, or IgE, respectively. The immunoglobulin subclasses (isotypes) e.g., IgG1, IgG2, IgG3, IgG4, IgA1, IgA2, etc. are well characterized and are known to confer functional specialization. Modified versions of each of these classes and isotypes are readily discernable to the skilled artisan in view of the instant disclosure and, accordingly, are within the scope of the instant disclosure. All immunoglobulin classes are clearly within the scope of the present disclosure, the following discussion will generally be directed to the IgG class of immunoglobulin molecules. With regard to IgG, a standard immunoglobulin molecule comprises two identical light chain polypeptides of molecular weight approximately 23,000 Daltons, and two identical heavy chain polypeptides of molecular weight 53,000-70,000. The four chains are typically joined by disulfide bonds in a "Y" configuration wherein the light chains bracket the heavy chains starting at the mouth of the "Y" and continuing through the variable region.

Light chains are classified as either kappa or lambda (κ, λ.) Each heavy chain class can be bound with either a kappa or lambda light chain. In general, the light and heavy chains are covalently bonded to each other, and the "tail" portions of the two heavy chains are bonded to each other by covalent disulfide linkages or non-covalent linkages when the immunoglobulins are generated either by hybridomas, B cells or genetically engineered host cells. In the heavy chain, the amino acid sequences run from an N-terminus at the forked ends of the Y configuration to the C-terminus at the bottom of each chain.

Both the light and heavy chains are divided into regions of structural and functional homology. The terms "constant" and "variable" are used functionally. In this regard, it will be appreciated that the variable domains of both the light (VL or VK) and heavy (VH) chain portions determine antigen recognition and specificity. Conversely, the constant domains of the light chain (CL) and the heavy chain (typically CH1, CH2 or CH3) confer important biological properties such as secretion, transplacental mobility, Fc receptor binding, complement binding, and the like. By convention the numbering of the constant region domains increases as they become more distal from the antigen binding site or amino-terminus of the antibody. The N-terminal portion is a variable region and at the C-terminal portion is a constant region; the CH3 and CL domains typically comprise the carboxy-terminus of the heavy and light chain, respectively.

As indicated above, the variable region allows the antibody to selectively recognize and specifically bind epitopes on antigens. That is, the VL domain and VH domain, or subset of the complementarity determining regions (CDRs) within these variable domains, of an antibody combine to form the variable region that defines a three dimensional antigen binding site. This quaternary antibody structure forms the antigen binding site present at the end of each arm of the Y. More specifically, the antigen binding site is defined by three CDRs on each of the VH and VL chains. In some instances, e.g., certain immunoglobulin molecules derived from camelid species or engineered based on camelid immunoglobulins, a complete immunoglobulin molecule can consist of heavy chains only, with no light chains. See, e.g., Hamers-Casterman et al., Nature 363:446-448 (1993).

In naturally occurring antibodies, the six "complementarity determining regions" or "CDRs" present in each antigen binding domain are short, non-contiguous sequences of amino acids that are specifically positioned to form the antigen binding domain as the antibody assumes its three dimensional configuration in an aqueous environment. The remainder of the amino acids in the antigen binding domains, referred to as "framework" regions, show less inter-molecular variability. The framework regions largely adopt a β-sheet conformation and the CDRs form loops that connect, and in some cases form part of, the β-sheet structure. Thus, framework regions act to form a scaffold that provides for positioning the CDRs in correct orientation by inter-chain, non-covalent interactions. The antigen binding domain formed by the positioned CDRs defines a surface complementary to the epitope on the immunoreactive antigen. This complementary surface promotes the non-covalent binding of the antibody to its cognate epitope. The amino acids comprising the CDRs and the framework regions, respectively, can be readily identified for any given heavy or light chain variable domain by one of ordinary skill in the art, since they have been precisely defined (see below).

In the case where there are two or more definitions of a term that is used and/or accepted within the art, the definition of the term as used herein is intended to include all such meanings unless explicitly stated to the contrary. A specific example is the use of the term "complementarity determining region" ("CDR") to describe the non-contiguous antigen combining sites found within the variable region of both heavy and light chain polypeptides. This particular region has been described by Kabat et al. (1983) U.S. Dept. of Health and Human Services, "Sequences of Proteins of Immunological Interest" and by Chothia and Lesk, *J. Mol. Biol.* 196:901-917 (1987), which are incorporated herein by reference, where the definitions include overlapping or subsets of amino acid residues when compared against each other. Nevertheless, application of either definition to refer to a CDR of an antibody or variants thereof is intended to be within the scope of the term as defined and used herein. The appropriate amino acid residues that encompass the CDRs as defined by each of the above cited references are set forth below in Table 1 as a comparison. The exact residue numbers that encompass a particular CDR will vary depending on the sequence and size of the CDR. Those skilled in the art can routinely determine which residues comprise a particular CDR given the variable region amino acid sequence of the antibody.

TABLE 1

| | CDR Definitions[1] | |
|---|---|---|
| | Kabat | Chothia |
| VH CDR1 | 31-35 | 26-32 |

TABLE 1-continued

CDR Definitions[1]

| | Kabat | Chothia |
|---|---|---|
| VH CDR2 | 50-65 | 52-58 |
| VH CDR3 | 95-102 | 95-102 |
| VL CDR1 | 24-34 | 26-32 |
| VL CDR2 | 50-56 | 50-52 |
| VL CDR3 | 89-97 | 91-96 |

[1]Numbering of all CDR definitions in Table 1 is according to the numbering conventions set forth by Kabat et al. (see below).

Kabat et al. also defined a numbering system for variable domain sequences that is applicable to any antibody. One of ordinary skill in the art can unambiguously assign this system of "Kabat numbering" to any variable domain sequence, without reliance on any experimental data beyond the sequence itself. As used herein, "Kabat numbering" refers to the numbering system set forth by Kabat et al. (1983) U.S. Dept. of Health and Human Services, "Sequence of Proteins of Immunological Interest." Unless otherwise specified, references to the numbering of specific amino acid residue positions in an anti-SEMA4D antibody or antigen-binding fragment, variant, or derivative thereof of the present disclosure are according to the Kabat numbering system.

Antibodies or antigen-binding fragments, variants, or derivatives thereof of the disclosure include, but are not limited to, polyclonal, monoclonal, multispecific and bispecific in which at least one arm is specific for SEMA4D, human, humanized, primatized, or chimeric antibodies, single-chain antibodies, epitope-binding fragments, e.g., Fab, Fab' and F(ab')$_2$, Fd, Fvs, single-chain Fvs (scFv), disulfide-linked Fvs (sdFv), fragments comprising either a VL or VH domain, fragments produced by a Fab expression library, and anti-idiotypic (anti-Id) antibodies (including, e.g., anti-Id antibodies to anti-SEMA4D antibodies disclosed herein). ScFv molecules are known in the art and are described, e.g., in U.S. Pat. No. 5,892,019. Immunoglobulin or antibody molecules of the disclosure can be of any type (e.g., IgG, IgE, IgM, IgD, IgA, and IgY), class (e.g., IgG1, IgG2, IgG3, IgG4, IgA1, and IgA2, etc.), or subclass of immunoglobulin molecule.

As used herein, the term "heavy chain portion" includes amino acid sequences derived from an immunoglobulin heavy chain. In certain embodiments, a polypeptide comprising a heavy chain portion comprises at least one of: a VH domain, a CH1 domain, a hinge (e.g., upper, middle, and/or lower hinge region) domain, a CH2 domain, a CH3 domain, or a variant or fragment thereof. For example, a binding polypeptide for use in the disclosure can comprise a polypeptide chain comprising a CH1 domain; a polypeptide chain comprising a CH1 domain, at least a portion of a hinge domain, and a CH2 domain; a polypeptide chain comprising a CH1 domain and a CH3 domain; a polypeptide chain comprising a CH1 domain, at least a portion of a hinge domain, and a CH3 domain, or a polypeptide chain comprising a CH1 domain, at least a portion of a hinge domain, a CH2 domain, and a CH3 domain. In another embodiment, a polypeptide of the disclosure comprises a polypeptide chain comprising a CH3 domain. Further, a binding polypeptide for use in the disclosure can lack at least a portion of a CH2 domain (e.g., all or part of a CH2 domain). As set forth above, it will be understood by one of ordinary skill in the art that these domains (e.g., the heavy chain portions) can be modified such that they vary in amino acid sequence from the naturally occurring immunoglobulin molecule.

In certain anti-SEMA4D antibodies, or antigen-binding fragments, variants, or derivatives thereof disclosed herein, the heavy chain portions of one polypeptide chain of a multimer are identical to those on a second polypeptide chain of the multimer. Alternatively, heavy chain portion-containing monomers of the disclosure are not identical. For example, each monomer can comprise a different target binding site, forming, for example, a bispecific antibody.

The heavy chain portions of a binding molecule for use in the methods disclosed herein can be derived from different immunoglobulin molecules. For example, a heavy chain portion of a polypeptide can comprise a $C_{H1}$ domain derived from an IgG1 molecule and a hinge region derived from an IgG3 molecule. In another example, a heavy chain portion can comprise a hinge region derived, in part, from an IgG1 molecule and, in part, from an IgG3 molecule. In another example, a heavy chain portion can comprise a chimeric hinge derived, in part, from an IgG1 molecule and, in part, from an IgG4 molecule.

As used herein, the term "light chain portion" includes amino acid sequences derived from an immunoglobulin light chain, e.g., a kappa or lambda light chain. In some aspects, the light chain portion comprises at least one of a VL or CL domain.

Anti-SEMA4D antibodies, or antigen-binding fragments, variants, or derivatives thereof disclosed herein can be described or specified in terms of the epitope(s) or portion(s) of an antigen, e.g., a target polypeptide disclosed herein (e.g., SEMA4D) that they recognize or specifically bind. The portion of a target polypeptide that specifically interacts with the antigen binding domain of an antibody is an "epitope," or an "antigenic determinant." A target polypeptide can comprise a single epitope, but typically comprises at least two epitopes, and can include any number of epitopes, depending on the size, conformation, and type of antigen. Furthermore, it should be noted that an "epitope" on a target polypeptide can be or can include non-polypeptide elements, e.g., an epitope can include a carbohydrate side chain.

The minimum size of a peptide or polypeptide epitope for an antibody is thought to be about four to five amino acids. Peptide or polypeptide epitopes can contain, e.g., at least seven, at least nine or between at least about 15 to about 30 amino acids. Since a CDR can recognize an antigenic peptide or polypeptide in its tertiary form, the amino acids comprising an epitope need not be contiguous, and in some cases, can be on separate peptide chains. A peptide or polypeptide epitope recognized by anti-SEMA4D antibodies of the present disclosure can contain a sequence of at least 4, at least 5, at least 6, at least 7, at least 8, at least 9, at least 10, at least 15, at least 20, at least 25, or between about 15 to about 30 contiguous or non-contiguous amino acids of SEMA4D.

By "specifically binds," it is generally meant that an antibody binds to an epitope via its antigen binding domain, and that the binding entails some complementarity between the antigen binding domain and the epitope. According to this definition, an antibody is said to "specifically bind" to an epitope when it binds to that epitope, via its antigen binding domain more readily than it would bind to a random, unrelated epitope. The term "specificity" is used herein to qualify the relative affinity by which a certain antibody binds to a certain epitope. For example, antibody "A" can be deemed to have a higher specificity for a given epitope than antibody "B," or antibody "A" can be said to bind to epitope "C" with a higher specificity than it has for related epitope "D."

By "preferentially binds," it is meant that the antibody specifically binds to an epitope more readily than it would bind to a related, similar, homologous, or analogous epitope. Thus, an antibody that "preferentially binds" to a given epitope would more likely bind to that epitope than to a related epitope, even though such an antibody can cross-react with the related epitope.

By way of non-limiting example, an antibody can be considered to bind a first epitope preferentially if it binds the first epitope with a dissociation constant ($K_D$) that is less than the antibody's $K_D$ for the second epitope. In another non-limiting example, an antibody can be considered to bind a first antigen preferentially if it binds the first epitope with an affinity that is at least one order of magnitude less than the antibody's $K_D$ for the second epitope. In another non-limiting example, an antibody can be considered to bind a first epitope preferentially if it binds the first epitope with an affinity that is at least two orders of magnitude less than the antibody's $K_D$ for the second epitope.

In another non-limiting example, an antibody can be considered to bind a first epitope preferentially if it binds the first epitope with an off rate (k(off)) that is less than the antibody's k(off) for the second epitope. In another non-limiting example, an antibody can be considered to bind a first epitope preferentially if it binds the first epitope with an affinity that is at least one order of magnitude less than the antibody's k(off) for the second epitope. In another non-limiting example, an antibody can be considered to bind a first epitope preferentially if it binds the first epitope with an affinity that is at least two orders of magnitude less than the antibody's k(off) for the second epitope. An antibody or antigen-binding fragment, variant, or derivative disclosed herein can be said to bind a target polypeptide disclosed herein (e.g., SEMA4D, e.g., human, murine, or both human and murine SEMA4D) or a fragment or variant thereof with an off rate (k(off)) of less than or equal to $5\times10^{-2}$ sec$^{-1}$, $10^{-2}$ sec$^{-1}$, $5\times10^{-3}$ sec$^{-1}$ or $10^{-3}$ sec$^{-1}$. In certain aspects, an antibody of the disclosure can be said to bind a target polypeptide disclosed herein (e.g., SEMA4D, e.g., human, murine, or both human and murine SEMA4D) or a fragment or variant thereof with an off rate (k(off)) less than or equal to $5\times10^{-4}$ sec$^{-1}$, $10^{-4}$ sec$^{-1}$, $5\times10^{-5}$ sec$^{-1}$, or $10^{-5}$ sec$^{-1}$, $5\times10^{-6}$ sec$^{-1}$, $10^{-6}$ sec$^{-1}$, $5\times10^{-7}$ sec$^{-1}$ or $10^{-7}$ sec$^{-1}$.

An antibody or antigen-binding fragment, variant, or derivative disclosed herein can be said to bind a target polypeptide disclosed herein (e.g., SEMA4D, e.g., human, murine, or both human and murine SEMA4D) or a fragment or variant thereof with an on rate (k(on)) of greater than or equal to $10^3$ M$^{-1}$ sec$^{-1}$, $5\times10^3$ M$^{-1}$ sec$^{-1}$, $10^4$ M$^{-1}$ sec$^{-1}$ or $5\times10^4$ M$^{-1}$ sec$^{-1}$. In some embodiments, an antibody of the disclosure cab be said to bind a target polypeptide disclosed herein (e.g., SEMA4D, e.g., human, murine, or both human and murine SEMA4D) or a fragment or variant thereof with an on rate (k(on)) greater than or equal to $10^5$ M$^{-1}$ sec$^{-1}$, $5\times10^5$ M$^{-1}$ sec$^{-1}$, $10^6$ M$^{-1}$ sec$^{-1}$, or $5\times10^6$ M$^{-1}$ sec$^{-1}$ or $10^7$ M$^{-1}$ sec$^{-1}$.

An antibody is said to competitively inhibit binding of a reference antibody to a given epitope if it preferentially binds to that epitope to the extent that it blocks, to some degree, binding of the reference antibody to the epitope. Competitive inhibition can be determined by any method known in the art, for example, competition ELISA assays. An antibody can be said to competitively inhibit binding of the reference antibody to a given epitope by at least 90%, at least 80%, at least 70%, at least 60%, or at least 50%.

As used herein, the term "affinity" refers to a measure of the strength of the binding of an individual epitope with the CDR of an immunoglobulin molecule. See, e.g., Harlow et al. (1988) Antibodies: A Laboratory Manual (Cold Spring Harbor Laboratory Press, 2nd ed.) pages 27-28. As used herein, the term "avidity" refers to the overall stability of the complex between a population of immunoglobulins and an antigen, that is, the functional combining strength of an immunoglobulin mixture with the antigen. See, e.g., Harlow at pages 29-34. Avidity is related to both the affinity of individual immunoglobulin molecules in the population with specific epitopes, and also the valencies of the immunoglobulins and the antigen. For example, the interaction between a bivalent monoclonal antibody and an antigen with a highly repeating epitope structure, such as a polymer, would be one of high avidity.

Anti-SEMA4D antibodies or antigen-binding fragments, variants, or derivatives thereof of the disclosure can also be described or specified in terms of their cross-reactivity. As used herein, the term "cross-reactivity" refers to the ability of an antibody, specific for one antigen, to react with a second antigen; a measure of relatedness between two different antigenic substances. Thus, an antibody is cross reactive if it binds to an epitope other than the one that induced its formation. The cross reactive epitope generally contains many of the same complementary structural features as the inducing epitope, and in some cases, can actually fit better than the original.

For example, certain antibodies have some degree of cross-reactivity, in that they bind related, but non-identical epitopes, e.g., epitopes with at least 95%, at least 90%, at least 85%, at least 80%, at least 75%, at least 70%, at least 65%, at least 60%, at least 55%, and at least 50% identity (as calculated using methods known in the art and described herein) to a reference epitope. An antibody can be said to have little or no cross-reactivity if it does not bind epitopes with less than 95%, less than 90%, less than 85%, less than 80%, less than 75%, less than 70%, less than 65%, less than 60%, less than 55%, and less than 50% identity (as calculated using methods known in the art and described herein) to a reference epitope. An antibody can be deemed "highly specific" for a certain epitope, if it does not bind any other analog, ortholog, or homolog of that epitope.

Anti-SEMA4D binding molecules, e.g., antibodies or antigen-binding fragments, variants or derivatives thereof, of the disclosure can also be described or specified in terms of their binding affinity to a polypeptide of the disclosure, e.g., SEMA4D, e.g., human, murine, or both human and murine SEMA4D. In certain aspects, the binding affinities include those with a dissociation constant or Kd less than $5\times10^{-2}$ M, $10^{-2}$ M, $5\times10^{-3}$ M, $10^{-3}$ M, $5\times10^{-4}$ M, $10^{-4}$ M, $5\times10^{-5}$ M, $10^{-5}$ M, $5\times10^{-6}$ M, $10^{-6}$ M, $5\times10^{-7}$ M, $10^{-7}$ M, $5\times10^{-8}$ M, $10^{-8}$ M, $5\times10^{-9}$ M, $10^{-9}$ M, $5\times10^{-10}$ M, $10^{-10}$ M, $5\times10^{-11}$ M, $10^{-11}$ M, $5\times10^{-12}$ M, $10^{-12}$ M, $5\times10^{-13}$ M, $10^{-13}$ M, $5\times10^{-14}$ M, $10^{-14}$ M, $5\times10^{-15}$ M, or $10^{-15}$ M. In certain embodiments, the anti-SEMA4D binding molecule, e.g., an antibody or antigen binding fragment thereof, of the disclosure binds human SEMA4D with a Kd of about $5\times10^{-9}$ to about $6\times10^{-9}$. In another embodiment, the anti-SEMA4D binding molecule, e.g., an antibody or antigen binding fragment thereof, of the disclosure binds murine SEMA4D with a Kd of about $1\times10^{-9}$ to about $2\times10^{-9}$.

As used herein, the term "chimeric antibody" will be held to mean any antibody wherein the immunoreactive region or site is obtained or derived from a first species and the constant region (which can be intact, partial or modified in accordance with the instant disclosure) is obtained from a second species. In certain embodiments the target binding region or site will be from a non-human source (e.g., mouse or primate) and the constant region is human.

As used herein, the term "engineered antibody" refers to an antibody in which the variable domain in either the heavy or light chain or both is altered by at least partial replacement of one or more CDRs from an antibody of known specificity and, if necessary, by partial framework region replacement and sequence changing. Although the CDRs can be derived from an antibody of the same class or even subclass as the antibody from which the framework regions are derived, it is envisaged that the CDRs will be derived from an antibody of different class, or from an antibody from a different species. An engineered antibody in which one or more "donor" CDRs from a non-human antibody of known specificity is grafted into a human heavy or light chain framework region is referred to herein as a "humanized antibody." It is not always necessary to replace all of the CDRs with the complete CDRs from the donor variable domain to transfer the antigen binding capacity of one variable domain to another. Rather, one can transfer just those residues needed to maintain the activity of the target binding site need be transferred.

It is further recognized that the framework regions within the variable domain in a heavy or light chain, or both, of a humanized antibody can comprise solely residues of human origin, in which case these framework regions of the humanized antibody are referred to as "fully human framework regions" (for example, MAbs 1515/2503 or 67, disclosed in U.S. Patent Appl. Publication No. US 2010/0285036 A1 as MAb 2503, incorporated herein by reference in its entirety). Alternatively, one or more residues of the framework region(s) of the donor variable domain can be engineered within the corresponding position of the human framework region(s) of a variable domain in a heavy or light chain, or both, of a humanized antibody if necessary to maintain proper binding or to enhance binding to the SEMA4D antigen. A human framework region that has been engineered in this manner would thus comprise a mixture of human and donor framework residues, and is referred to herein as a "partially human framework region."

For example, humanization of an anti-SEMA4D antibody can be essentially performed following the method of Winter and co-workers (Jones et al., Nature 321:522-525 (1986); Riechmann et al., Nature 332:323-327 (1988); Verhoeyen et al., Science 239:1534-1536 (1988)), by substituting rodent or mutant rodent CDRs or CDR sequences for the corresponding sequences of a human anti-SEMA4D antibody. See also U.S. Pat. Nos. 5,225,539; 5,585,089; 5,693,761; 5,693,762; 5,859,205; herein incorporated by reference. The resulting humanized anti-SEMA4D antibody would comprise at least one rodent or mutant rodent CDR within the fully human framework regions of the variable domain of the heavy and/or light chain of the humanized antibody. In some instances, residues within the framework regions of one or more variable domains of the humanized anti-SEMA4D antibody are replaced by corresponding non-human (for example, rodent) residues (see, for example, U.S. Pat. Nos. 5,585,089; 5,693,761; 5,693,762; and 6,180,370), in which case the resulting humanized anti-SEMA4D antibody would comprise partially human framework regions within the variable domain of the heavy and/or light chain.

Furthermore, humanized antibodies can comprise residues that are not found in the recipient antibody or in the donor antibody. These modifications are made to further refine antibody performance (e.g., to obtain desired affinity). In general, the humanized antibody will comprise substantially all of at least one, and typically two, variable domains, in which all or substantially all of the CDRs correspond to those of a non-human immunoglobulin and all or substantially all of the framework regions are those of a human immunoglobulin sequence. The humanized antibody optionally also will comprise at least a portion of an immunoglobulin constant region (Fc), typically that of a human immunoglobulin. For further details see Jones et al., Nature 331:522-525 (1986); Riechmann et al., Nature 332:323-329 (1988); and Presta, Curr. Op. Struct. Biol. 2:593-596 (1992); herein incorporated by reference. Accordingly, such "humanized" antibodies can include antibodies wherein substantially less than an intact human variable domain has been substituted by the corresponding sequence from a non-human species. In practice, humanized antibodies are typically human antibodies in which some CDR residues and possibly some framework residues are substituted by residues from analogous sites in rodent antibodies. See, for example, U.S. Pat. Nos. 5,225,539; 5,585,089; 5,693,761; 5,693,762; 5,859,205. See also U.S. Pat. No. 6,180,370, and International Publication No. WO 01/27160, where humanized antibodies and techniques for producing humanized antibodies having improved affinity for a predetermined antigen are disclosed.

As used herein, the term "healthcare provider" refers to individuals or institutions that directly interact and administer to living subjects, e.g., human patients. Non-limiting examples of healthcare providers include doctors, nurses, technicians, therapist, pharmacists, counselors, alternative medicine practitioners, medical facilities, doctor's offices, hospitals, emergency rooms, clinics, urgent care centers, alternative medicine clinics/facilities, and any other entity providing general and/or specialized treatment, assessment, maintenance, therapy, medication, and/or advice relating to all, or any portion of, a patient's state of health, including but not limited to general medical, specialized medical, surgical, and/or any other type of treatment, assessment, maintenance, therapy, medication and/or advice.

As used herein, the term "healthcare benefits provider" encompasses individual parties, organizations, or groups providing, presenting, offering, paying for in whole or in part, or being otherwise associated with giving a patient access to one or more healthcare benefits, benefit plans, health insurance, and/or healthcare expense account programs.

As used herein, the term "clinical laboratory" refers to a facility for the examination or processing of materials or images derived from a living subject, e.g., a human being. Non-limiting examples of processing include biological, biochemical, serological, chemical, immunohematological, hematological, biophysical, cytological, pathological, genetic, image based, or other examination of materials derived from the human body or of any or all of the human body for the purpose of providing information, e.g., for the diagnosis, prevention, or treatment of any disease or impairment of, or the assessment of the health of living subjects, e.g., human beings. These examinations can also include procedures to collect or otherwise obtain an image, a sample, prepare, determine, measure, or otherwise describe the presence or absence of various substances in the body of a living subject, e.g., a human being, or a sample obtained from the body of a living subject, e.g., a human being.

II. Target Polypeptide Description

As used herein, the terms "Semaphorin 4D," "SEMA4D" and "SEMA4D polypeptide" are used interchangeably, as are "SEMA4D" and "Sema4D." In certain embodiments, SEMA4D is expressed on the surface of or secreted by a cell. In another embodiment, SEMA4D is membrane bound. In another embodiment, SEMA4D is soluble, e.g., sSEMA4D. In other embodiments, SEMA4D can include a full-sized SEMA4D or a fragment thereof, or a SEMA4D variant polypeptide, wherein the fragment of SEMA4D or SEMA4D variant polypeptide retains some or all functional properties of the full-sized SEMA4D.

The full-sized human SEMA4D protein is a homodimeric transmembrane protein consisting of two polypeptide chains of 150 kDa. SEMA4D belongs to the semaphorin family of cell surface receptors and is also referred to as CD100. Both human and mouse SEMA4D/Sema4D are proteolytically cleaved from their transmembrane form to generate 120-kDa soluble forms, indicating the existence of two Sema4D isoforms (Kumanogoh et al., *J. Cell Science* 116(7):3464 (2003)). Semaphorins consist of soluble and membrane-bound proteins that were originally defined as axonal-guidance factors during development which play an important role in establishing precise connections between neurons and their appropriate target. Structurally considered a class IV semaphorin, SEMA4D consists of an amino-terminal signal sequence followed by a characteristic 'Sema' domain, which contains 17 conserved cysteine residues, an Ig-like domain, a lysine-rich stretch, a hydrophobic transmembrane region, and a cytoplasmic tail.

A polypeptide chain of SEMA4D can include a signal sequence of about 13 amino acids and further includes a semaphorin domain of about 512 amino acids, an immunoglobulin-like (Ig-like) domain of about 65 amino acids, a lysine-rich stretch of 104 amino acids, a hydrophobic transmembrane region of about 19 amino acids, and a cytoplasmic tail of 110 amino acids. A consensus site for tyrosine phosphorylation in the cytoplasmic tail supports the predicted association of SEMA4D with a tyrosine kinase (Schlossman, et al., Eds. (1995) Leucocyte Typing V (Oxford University Press, Oxford).

SEMA4D is known to have at least three functional receptors, Plexin-B1, Plexin-B2 and CD72. One of the receptors, Plexin-B1, is expressed in non-lymphoid tissues and has been shown to be a high affinity (1 nM) receptor for SEMA4D (Tamagnone et al., *Cell* 99:71-80 (1999)). SEMA4D stimulation of Plexin-B1 signaling has been shown to induce growth cone collapse of neurons, and to induce process extension collapse and apoptosis of oligodendrocytes (Giraudon et al., *J. Immunol.* 172:1246-1255 (2004); Giraudon et al., *NeuroMolecular Med.* 7:207-216 (2005)). After binding to SEMA4D, Plexin-B1 signaling mediates the inactivation of R-Ras, leading to a decrease in the integrin mediated attachment to the extracellular matrix, as well as to activation of RhoA, leading to reorganization of the cytoskeleton and cell migration. See Kruger et al., *Nature Rev. Mol. Cell Biol.* 6:789-800 (2005); Pasterkamp, *TRENDS in Cell Biology* 15:61-64 (2005)). Plexin-B2, on the other hand, has an intermediate affinity for SEMA4D and recent reports indicate that Plexin-B2 regulates migration of cortical neurons and proliferation and migration of neuroblasts in the adult subventricular zone (Azzarelli et al, *Nat Commun* 2014 Feb. 27, 5:3405, DOI: 10.1038/ncomms4405; and Saha et al., *J. Neuroscience,* 2012 Nov. 21, 32(47): 16892-16905).

In lymphoid tissues CD72 is utilized as a low affinity (300 nM) SEMA4D receptor (Kumanogoh et al., *Immunity* 13:621-631 (2000)). B cells and APCs express CD72, and anti-CD72 antibodies have many of the same effects as sSEMA4D, such as enhancement of CD40-induced B cell responses and B cell shedding of CD23. CD72 is thought to act as a negative regulator of B cell responses by recruiting the tyrosine phosphatase SHP-1, which can associate with many inhibitory receptors. Interaction of SEMA4D with CD72 results in the dissociation of SHP-1, and the loss of this negative activation signal. SEMA4D has been reported to promote T cell stimulation and B cell aggregation and survival in vitro. The addition of SEMA4D-expressing cells or sSEMA4D enhances CD40-induced B cell proliferation and immunoglobulin production in vitro, and accelerates in vivo antibody responses (Ishida et al., *Inter. Immunol.* 15:1027-1034 (2003); Kumanogoh and H. Kukutani, *Trends in Immunol.* 22:670-676 (2001)). sSEMA4D enhances the CD40 induced maturation of dendritic cells (DCs), including up-regulation of costimulatory molecules and increased secretion of IL-12. In addition, sSEMA4D can inhibit immune cell migration, which can be reversed by addition of blocking anti-SEMA4D antibodies (Elhabazi et al., *J. Immunol.* 166:4341-4347 (2001); Delaire et al., *J. Immunol.* 166:4348-4354 (2001)).

Sema4D is expressed at high levels in lymphoid organs, including the spleen, thymus, and lymph nodes, and in non-lymphoid organs, such as the brain, heart, and kidney. In lymphoid organs, Sema4D is abundantly expressed on resting T cells but only weakly expressed on resting B cells and antigen-presenting cells (APCs), such as DCs. Cellular activation increases the surface expression of SEMA4D as well as the generation of soluble SEMA4D (sSEMA4D).

The expression pattern of SEMA4D suggests that it plays an important physiological as well as pathological role in the immune system. SEMA4D has been shown to promote B cell activation, aggregation and survival; enhance CD40-induced proliferation and antibody production; enhance antibody response to T cell dependent antigens; increase T cell proliferation; enhance dendritic cell maturation and ability to stimulate T cells; and is directly implicated in demyelination and axonal degeneration (Shi et al., *Immunity* 13:633-642 (2000); Kumanogoh et al., *J Immunol* 169:1175-1181 (2002); and Watanabe et al., *J Immunol* 167:4321-4328 (2001)).

SEMA4D knock out (SEMA4D−/−) mice have provided additional evidence that SEMA4D plays an important role in both humoral and cellular immune responses. There are no known major abnormalities of non-lymphoid tissues in SEMA4D−/− mice. DCs from the SEMA4D−/− mice have poor allostimulatory ability and show defects in expression of costimulatory molecules, which can be rescued by the addition of sSEMA4D. Mice deficient in SEMA4D (SEMA4D−/−) fail to develop experimental autoimmune encephalomyelitis induced by myelin oligodendrocyte glycoprotein peptide, because myelin oligodendrocyte glycoprotein-specific T cells are poorly generated in the absence of SEMA4D (Kumanogoh et al., *J Immunol* 169:1175-1181 (2002)). A significant amount of soluble SEMA4D is also detected in the sera of autoimmunity-prone MRL/lpr mice (model of systemic autoimmune diseases such as SLE), but not in normal mice. Further, the levels of sSEMA4D correlate with levels of auto-antibodies and increase with age (Wang et al., *Blood* 97:3498-3504 (2001)). Soluble SEMA4D has also been shown to accumulate in the cerebral spinal fluid and sera of patients with demyelinating disease, and sSEMA4D induces apoptosis of human pluripotent neural precursors (Dev cells), and both inhibit process extension and induce apoptosis of rat oligodendrocytes in vitro (Giraudon et al., *J Immunol* 172(2):1246-1255 (2004)). This apoptosis was blocked by an anti-SEMA4D MAb.

III. Anti-SEMA4D Antibodies

Antibodies that bind SEMA4D have been described in the art. See, for example, U.S. Pat. No. 8,496,938, US Publ. Nos. 2008/0219971 A1, US 2010/0285036 A1, and US 2006/0233793 A1, International Patent Applications WO 93/14125, WO 2008/100995, and WO 2010/129917, and Herold et al., *Int. Immunol.* 7(1): 1-8 (1995), each of which is herein incorporated in its entirety by reference.

The disclosure generally relates to a method of alleviating symptoms in a subject having a neuroinflammatory or neurodegenerative disorder, e.g., a human patient, comprising administration of an antibody which specifically binds to SEMA4D, or an antigen-binding fragment, variant, or derivative thereof. In certain embodiments, the antibody blocks the interaction of SEMA4D with one or more of its receptors, e.g., Plexin-B1. Anti-SEMA4D antibodies having these properties can be used in the methods provided herein. Antibodies that can be used include, but are not limited to MAbs VX15/2503, 67, and 76 and antigen-binding fragments, variants, or derivatives thereof which are fully described in US 2010/0285036 A1. Additional antibodies which can be used in the methods provided herein include the BD16 and BB18 antibodies described in US 2006/0233793 A1 as well as antigen-binding fragments, variants, or derivatives thereof; or any of MAb 301, MAb 1893, MAb 657, MAb 1807, MAb 1656, MAb 1808, Mab 59, MAb 2191, MAb 2274, MAb 2275, MAb 2276, MAb 2277, MAb 2278, MAb 2279, MAb 2280, MAb 2281, MAb 2282, MAb 2283, MAb 2284, and MAb 2285, as well as any fragments, variants or derivatives thereof as described in US 2008/0219971 A1. In certain embodiments an anti-SEMA4D antibody for use in the methods provided herein binds human, murine, or both human and murine SEMA4D. Also useful are antibodies which bind to the same epitope as any of the aforementioned antibodies and/or antibodies which competitively inhibit any of the aforementioned antibodies.

In certain embodiments, an anti-SEMA4D antibody or antigen-binding fragment, variant, or derivative thereof useful in the methods provided herein has an amino acid sequence that has at least about 80%, about 85%, about 88%, about 89%, about 90%, about 91%, about 92%, about 93%, about 94%, or about 95% sequence identity to the amino acid sequence for a reference anti-SEMA4D antibody molecule, for example those described above. In a further embodiment, the binding molecule shares at least about 96%, about 97%, about 98%, about 99%, or 100% sequence identity to a reference antibody.

In another embodiment, an anti-SEMA4D antibody or antigen-binding fragment, variant, or derivative thereof useful in the methods provided herein comprises, consists essentially of, or consists of an immunoglobulin heavy chain variable domain (VH domain), where at least one of the CDRs of the VH domain has an amino acid sequence that is at least about 80%, about 85%, about 90%, about 95%, about 96%, about 97%, about 98%, about 99%, or identical to CDR1, CDR2 or CDR3 of SEQ ID NO: 9 or 10.

In another embodiment, an anti-SEMA4D antibody or antigen-binding fragment, variant, or derivative thereof useful in the methods provided herein comprises, consists essentially of, or consists of an immunoglobulin heavy chain variable domain (VH domain), where at least one of the CDRs of the VH domain has an amino acid sequence that is at least about 80%, about 85%, about 90%, about 95%, about 96%, about 97%, about 98%, about 99%, or identical to SEQ ID NO: 6, SEQ ID NO: 7, or SEQ ID NO: 8.

In another embodiment, an anti-SEMA4D antibody or antigen-binding fragment, variant, or derivative thereof useful in the methods provided herein comprises, consists essentially of, or consists of an immunoglobulin heavy chain variable domain (VH domain), where at least one of the CDRs of the VH domain has an amino acid sequence identical, except for 1, 2, 3, 4, or 5 conservative amino acid substitutions, to SEQ ID NO: 6, SEQ ID NO: 7, or SEQ ID NO: 8.

In another embodiment, an anti-SEMA4D antibody or antigen-binding fragment, variant, or derivative thereof useful in the methods provided herein comprises, consists essentially of, or consists of a VH domain that has an amino acid sequence that is at least about 80%, about 85%, about 90%, about 91%, about 92%, about 93%, about 94%, about 95%, about 96%, about 97%, about 98%, about 99%, or 100% identical to SEQ ID NO: 9 or SEQ ID NO: 10, wherein an anti-SEMA4D antibody comprising the encoded VH domain specifically or preferentially binds to SEMA4D.

In another embodiment, an anti-SEMA4D antibody or antigen-binding fragment, variant, or derivative thereof useful in the methods provided herein comprises, consists essentially of, or consists of an immunoglobulin light chain variable domain (VL domain), where at least one of the CDRs of the VL domain has an amino acid sequence that is at least about 80%, about 85%, about 90%, about 95%, about 96%, about 97%, about 98%, about 99%, or identical to CDR1, CDR2 or CDR3 of SEQ ID NO: 17 or 18.

In another embodiment, an anti-SEMA4D antibody or antigen-binding fragment, variant, or derivative thereof useful in the methods provided herein comprises, consists essentially of, or consists of an immunoglobulin light chain variable domain (VL domain), where at least one of the CDRs of the VL domain has an amino acid sequence that is at least about 80%, about 85%, about 90%, about 95%, about 96%, about 97%, about 98%, about 99%, or identical to SEQ ID NO: 14, SEQ ID NO: 15, or SEQ ID NO: 16.

In another embodiment, an anti-SEMA4D antibody or antigen-binding fragment, variant, or derivative thereof useful in the methods provided herein comprises, consists essentially of, or consists of an immunoglobulin light chain variable domain (VL domain), where at least one of the CDRs of the VL domain has an amino acid sequence identical, except for 1, 2, 3, 4, or 5 conservative amino acid substitutions, to SEQ ID NO: 14, SEQ ID NO: 15, or SEQ ID NO: 16.

In a further embodiment, an anti-SEMA4D antibody or antigen-binding fragment, variant, or derivative thereof useful in the methods provided herein comprises, consists essentially of, or consists of a VL domain that has an amino acid sequence that is at least about 80%, about 85%, about 90%, about 91%, about 92%, about 93%, about 94%, about 95%, about 96%, about 97%, about 98%, about 99%, or 100% identical to SEQ ID NO: 17 or SEQ ID NO: 18, wherein an anti-SEMA4D antibody comprising the encoded VL domain specifically or preferentially binds to SEMA4D.

Also included for use in the methods provided herein are polypeptides encoding anti-SEMA4D antibodies, or antigen-binding fragments, variants, or derivatives thereof as described herein, polynucleotides encoding such polypeptides, vectors comprising such polynucleotides, and host cells comprising such vectors or polynucleotides, all for producing anti-SEMA4D antibodies, or antigen-binding fragments, variants, or derivatives thereof for use in the methods described herein.

Suitable biologically active variants of the anti-SEMA4D antibodies of the disclosure can be used in the methods of the present disclosure. Such variants will retain the desired binding properties of the parent anti-SEMA4D antibody. Methods for making antibody variants are generally available in the art.

Methods for mutagenesis and nucleotide sequence alterations are well known in the art. See, for example, Walker and Gaastra, eds. (1983) Techniques in Molecular Biology (MacMillan Publishing Company, New York); Kunkel, *Proc. Natl. Acad. Sci. USA* 82:488-492 (1985); Kunkel et al., *Methods Enzymol.* 154:367-382 (1987); Sambrook et al. (1989) Molecular Cloning: A Laboratory Manual (Cold Spring Harbor, N.Y.); U.S. Pat. No. 4,873,192; and the references cited therein; herein incorporated by reference. Guidance as to appropriate amino acid substitutions that do not affect biological activity of the polypeptide of interest can be found in the model of Dayhoff et al. (1978) in Atlas of Protein Sequence and Structure (Natl. Biomed. Res. Found, Washington, D.C.), pp. 345-352, herein incorporated by reference in its entirety. The model of Dayhoff et al. uses the Point Accepted Mutation (PAM) amino acid similarity matrix (PAM 250 matrix) to determine suitable conservative amino acid substitutions. In certain embodiments, conservative substitutions, such as exchanging one amino acid with another having similar properties can be used. Examples of conservative amino acid substitutions as taught by the PAM 250 matrix of the Dayhoff et al. model include, but are not limited to, Gly↔Ala, Val↔Ile↔Leu, Asp↔Glu, Lys↔Arg, Asn↔Gln, and Phe↔Trp↔Tyr.

In constructing variants of the anti-SEMA4D binding molecule, e.g., an antibody or antigen-binding fragment thereof, polypeptides of interest, modifications are made such that variants continue to possess the desired properties, e.g., being capable of specifically binding to a SEMA4D, e.g., human, murine, or both human and murine SEMA4D, e.g., expressed on the surface of or secreted by a cell and having SEMA4D blocking activity, as described herein. Obviously, any mutations made in the DNA encoding the variant polypeptide must not place the sequence out of reading frame and in certain embodiments will not create complementary regions that could produce secondary mRNA structure. See EP Patent Application Publication No. 75,444.

Methods for measuring anti-SEMA4D binding molecule, e.g., an antibody or antigen-binding fragment, variant, or derivative thereof, binding specificity include, but are not limited to, standard competitive binding assays, assays for monitoring immunoglobulin secretion by T cells or B cells, T cell proliferation assays, apoptosis assays, ELISA assays, and the like. See, for example, such assays disclosed in WO 93/14125; Shi et al., *Immunity* 13:633-642 (2000); Kumanogoh et al., *J Immunol* 169:1175-1181 (2002); Watanabe et al., *J Immunol* 167:4321-4328 (2001); Wang et al., *Blood* 97:3498-3504 (2001); and Giraudon et al., *J Immunol* 172(2):1246-1255 (2004), all of which are herein incorporated by reference.

When discussed herein whether any particular polypeptide, including the constant regions, CDRs, VH domains, or VL domains disclosed herein, is at least about 65%, about 70%, about 75%, about 80%, about 85%, about 90%, about 91%, about 92%, about 93%, about 94%, about 95%, about 96%, about 97%, about 98%, about 99%, or even about 100% identical to another polypeptide, the % identity can be determined using methods and computer programs/software known in the art such as, but not limited to, the BESTFIT program (Wisconsin Sequence Analysis Package, Version 8 for Unix, Genetics Computer Group, University Research Park, 575 Science Drive, Madison, Wis. 53711). BESTFIT uses the local homology algorithm of Smith and Waterman (1981) Adv. Appl. Math. 2:482-489, to find the best segment of homology between two sequences. When using BESTFIT or any other sequence alignment program to determine whether a particular sequence is, for example, 95% identical to a reference sequence according to the present disclosure, the parameters are set, of course, such that the percentage of identity is calculated over the full length of the reference polypeptide sequence and that gaps in homology of up to 5% of the total number of amino acids in the reference sequence are allowed.

For purposes of the present disclosure, percent sequence identity can be determined using the Smith-Waterman homology search algorithm using an affine gap search with a gap open penalty of 12 and a gap extension penalty of 2, BLOSUM matrix of 62. The Smith-Waterman homology search algorithm is taught in Smith and Waterman (1981) Adv. Appl. Math. 2:482-489. A variant can, for example, differ from a reference anti-SEMA4D antibody (e.g., MAb VX15/2503, 67, or 76) by as few as 1 to 15 amino acid residues, as few as 1 to 10 amino acid residues, such as 6-10, as few as 5, as few as 4, 3, 2, or even 1 amino acid residue.

Percentage of "sequence identity" can also be determined by comparing two optimally aligned sequences over a comparison window. In order to optimally align sequences for comparison, the portion of a polynucleotide or polypeptide sequence in the comparison window can comprise additions or deletions termed gaps while the reference sequence is kept constant. An optimal alignment is that alignment which, even with gaps, produces the greatest possible number of "identical" positions between the reference and comparator sequences. Percentage "sequence identity" between two sequences can be determined using the version of the program "BLAST 2 Sequences" which was available from the National Center for Biotechnology Information as of Sep. 1, 2004, which program incorporates the programs BLASTN (for nucleotide sequence comparison) and BLASTP (for polypeptide sequence comparison), which programs are based on the algorithm of Karlin and Altschul (*Proc. Natl. Acad. Sci. USA* 90(12):5873-5877, 1993). When utilizing "BLAST 2 Sequences," parameters that were default parameters as of Sep. 1, 2004, can be used for word size (3), open gap penalty (11), extension gap penalty (1), gap drop-off (50), expect value (10) and any other required parameter including but not limited to matrix option.

The constant region of an anti-SEMA4D antibody can be mutated to alter effector function in a number of ways. For example, see U.S. Pat. No. 6,737,056B1 and U.S. Patent Application Publication No. 2004/0132101A1, which disclose Fc mutations that optimize antibody binding to Fc receptors.

In certain anti-SEMA4D antibodies or fragments, variants or derivatives thereof useful in the methods provided herein, the Fc portion can be mutated to decrease effector function using techniques known in the art. For example, the deletion or inactivation (through point mutations or other means) of a constant region domain can reduce Fc receptor binding of the circulating modified antibody thereby increasing tumor localization. In other cases, constant region modifications consistent with the instant disclosure moderate complement binding and thus reduce the serum half-life. Yet other modifications of the constant region can be used to modify disulfide linkages or oligosaccharide moieties that allow for enhanced localization due to increased antigen specificity or antibody flexibility. The resulting physiological profile, bioavailability and other biochemical effects of the modifications, such as tumor localization, biodistribution and serum half-life, can easily be measured and quantified using well known immunological techniques without undue experimentation. Anti-SEMA4D antibodies for use in the methods provided herein include derivatives that are modified, e.g., by the covalent attachment of any type of molecule to the antibody such that covalent attachment does not prevent the antibody from specifically binding to its cognate epitope. For example, but not by way of limitation, the antibody derivatives include antibodies that have been modified, e.g., by glycosylation, acetylation, pegylation, phosphorylation, amidation, derivatization by known protecting/blocking groups, proteolytic cleavage, linkage to a cellular ligand or other protein, etc. Any of numerous chemical modifications can be carried out by known techniques, including, but not limited to specific chemical cleavage, acetylation, formylation, etc. Additionally, the derivative can contain one or more non-classical amino acids.

A "conservative amino acid substitution" is one in which the amino acid residue is replaced with an amino acid residue having a side chain with a similar charge. Families of amino acid residues having side chains with similar charges have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Alternatively, mutations can be introduced randomly along all or part of the coding sequence, such as by saturation mutagenesis, and the resultant mutants can be screened for biological activity to identify mutants that retain activity (e.g., the ability to bind an anti-SEMA4D polypeptide, to block SEMA4D interaction with its receptor, or to alleviate symptoms associated with a neurodegenerative disorder in a patient).

For example, it is possible to introduce mutations only in framework regions or only in CDR regions of an antibody molecule. Introduced mutations can be silent or neutral missense mutations, i.e., have no, or little, effect on an antibody's ability to bind antigen. These types of mutations can be useful to optimize codon usage, or improve a hybridoma's antibody production. Alternatively, non-neutral missense mutations can alter an antibody's ability to bind antigen. One of skill in the art would be able to design and test mutant molecules with desired properties such as no alteration in antigen binding activity or alteration in binding activity (e.g., improvements in antigen binding activity or change in antibody specificity). Following mutagenesis, the encoded protein can routinely be expressed and the functional and/or biological activity of the encoded protein, (e.g., ability to immunospecifically bind at least one epitope of a SEMA4D polypeptide) can be determined using techniques described herein or by routinely modifying techniques known in the art.

In certain embodiments, the anti-SEMA4D antibodies for use in the methods provided herein comprise at least one optimized complementarity-determining region (CDR). By "optimized CDR" is intended that the CDR has been modified and optimized to improve binding affinity and/or anti-SEMA4D activity that is imparted to an anti-SEMA4D antibody comprising the optimized CDR. "Anti-SEMA4D activity" or "SEMA4D blocking activity" can include activity which modulates one or more of the following activities associated with SEMA4D: B cell activation, aggregation and survival; CD40-induced proliferation and antibody production; antibody response to T cell dependent antigens; T cell or other immune cell proliferation; dendritic cell maturation; demyelination and axonal degeneration; apoptosis of pluripotent neural precursors and/or oligodendrocytes; induction of endothelial cell migration; inhibition of spontaneous monocyte migration; binding to cell surface Plexin-B1 or other receptor, or any other activity associated with soluble SEMA4D or SEMA4D that is expressed on the surface of SEMA4D+ cells. Anti-SEMA4D activity can also be attributed to a decrease in incidence or severity of diseases associated with SEMA4D expression, including, but not limited to, certain types of cancers including lymphomas, autoimmune diseases, inflammatory diseases including central nervous system (CNS) and peripheral nervous system (PNS) inflammatory diseases, transplant rejections, and invasive angiogenesis. Examples of optimized antibodies based on murine anti-SEMA4D MAbs BD16 and BB18, were described in US Publ. No. 2008/0219971 A1, International Patent Application WO 93/14125 and Herold et al., Int. Immunol. 7(1): 1-8 (1995), each of which are herein incorporated by reference in their entirety. The modifications can involve replacement of amino acid residues within the CDR such that an anti-SEMA4D antibody retains specificity for the SEMA4D antigen and has improved binding affinity and/or improved anti-SEMA4D activity.

IV. Astrocytes

Astrocytes are specialized glial cells that perform many essential complex functions in the healthy CNS, including regulation of blood flow, fluid/ion/pH/neurotransmitter homeostasis, synapse formation/function, energy and metabolism, and blood-brain barrier maintenance (Barres B. A. (2008) The mystery and magic of glia: a perspective on their roles in health and disease. Neuron 60:430-440.) Importantly, astrocytes respond to CNS injury through a process referred to as reactive astrogliosis, which serves as a major pathological hallmark of neuroinflammatory and neurodegenerative diseases. Increasing evidence points towards the potential of reactive astrogliosis to play either primary or contributing roles in CNS disorders via loss of normal astrocyte functions or gain of abnormal activities. Given their central role in many CNS diseases, there is a significant need to identify and rigorously test new molecular targets that restore normal astrocyte function to effectively slow or even reverse disease progression. There are several potential pathways through which astrocytes can impact CNS diseases.

Astrocytes and OPC Support.

Demyelination that occurs in neuroinflammatory diseases, such as Multiple Sclerosis, is associated with marked destruction and loss of cells comprising the oligodendrocyte lineage (Ozawa K, et al. Patterns of oligodendroglia pathology in multiple sclerosis. Brain. 1994; 117:1311-1322.). Endogenous remyelination mechanisms fail during the recovery phase in part because of the inability of OPCs to fully differentiate into mature myelinating oligodendrocytes (Wolswijk G. Oligodendrocyte survival, loss and birth in lesions of chronic-stage multiple sclerosis. Brain. 2000; 123:105-115.). Data obtained from other experimentally induced demyelination models indicate that newly maturing OPCs, in contrast to surviving mature oligodendrocytes, are required for remyelination during the recovery phase (Levine J M, Reynolds R. Activation and proliferation of endogenous oligodendrocyte precursor cells during ethidium bromide-induced demyelination. Exp Neurol. 1999; 160:333-347). Astrocytes have been shown to play a significant role in supporting the function and viability of the oligodendrocyte lineage. For example, Talbott and colleagues showed that in ethidium bromide-induced demyelinated lesions, astrocytes are required for Nkx2.2+/Olig2+ OPCs to fully differentiate into oligodendrocytes and carry out remyelination (Exp Neurol. 2005 March; 192(1):11-24. Endogenous Nkx2.2+/Olig2+ oligodendrocyte precursor cells fail to remyelinate the demyelinated adult rat spinal cord in the absence of astrocytes. Talbott J F, Loy D N, Liu Y, Qiu M S, Bunge M B, Rao M S, Whittemore S R). Arai and Lo demonstrated in vitro that astrocytes provide soluble trophic factor support to OPCs that protect these cells from increased oxidative stress (Arai, K. and Lo, E. H. (2010), Astrocytes protect oligodendrocyte precursor cells via MEK/ERK and PI3K/Akt signaling. J. Neurosci. Res., 88: 758-763. doi: 10.1002/jnr.22256). Others have shown that inhibition of astrocyte activation in the settings of experimental autoimmune encephalomyelitis, experimental optic neuritis, and spinal cord injury leads to improved remyelination profiles and functional outcome measures (Brambilla R, Persaud T, Hu X, Karmally S, Shestopalov V I, Dvoriantchikova G, Ivanov D, Nathanson L, Barnum S R, Bethea J R. 2009. Transgenic inhibition of astroglial NF-kappa B improves functional outcome in experimental autoimmune encephalomyelitis by suppressing chronic central nervous system inflammation. *J Immunol* 182:2628-2640; Brambilla R, Dvoriantchikova G, Barakat D, Ivanov D, Bethea J R, Shestopalov V I. 2012. Transgenic inhibition of astroglial NF-kappaB protects from optic nerve damage and retinal ganglion cell loss in experimental optic neuritis. J Neuroinflammation 9:213; Brambilla R, Bracchi-Ricard V, Hu W H, Frydel B, Bramwell A, Karmally S, Green E J, Bethea J R. 2005. Inhibition of astroglial nuclear factor kappaB reduces inflammation and improves functional recovery after spinal cord injury. J Exp Med 202:145-156).

Given the role that astrocytes play in facilitation of OPC survival and function, the juxtaposition of SEMA4D-expressing OPCs and SEMA4D receptor-expressing astrocytes identified here suggests that disease-related activation of astrocytes with associated upregulation of plexin-B receptors and SEMA4D signaling have profound effects on OPC function.

Astrocytes and Neuronal Support.

Accumulating evidence indicates that astrocytes play direct roles in synaptic transmission through the regulated release of synaptically active molecules including glutamate, purines (ATP and adenosine), GABA, and D-serine (reviewed by Halassa M M, Fellin T, Haydon P G (2007), The tripartite synapse: roles for gliotransmission in health and disease. Trends Mol Med 13:54-63; Nedergaard M, Ransom B, Goldman S A (2003) New roles for astrocytes: redefining the functional architecture of the brain. Trends Neurosci 26:523-530). The release of such gliotransmitters occurs in response to changes in neuronal synaptic activity, involves astrocyte excitability as reflected by increases in astrocyte calcium signaling, and can alter neuronal excitability (Halassa M M, Fellin T, Haydon P G (2007), The tripartite synapse: roles for gliotransmission in health and disease. Trends Mol Med 13:54-63; Nedergaard M, Ransom B, Goldman S A (2003) New roles for astrocytes: redefining the functional architecture of the brain. Trends Neurosci 26:523-530). In addition to having direct effects on synaptic activity via the release of gliotransmitters, astrocytes have the potential to exert powerful and long-term influences on synaptic function through the release of growth factors and related molecules (Barres B A (2008) The mystery and magic of glia: a perspective on their roles in health and disease. Neuron 60:430-440).

Astrocytes and BBB Integrity.

Astrocytes play an essential role in formation of the blood-brain barrier (BBB) and in regulating transport across the BBB, a homeostatic process critical for proper neuronal function. The BBB is a highly complex brain endothelial structure of the differentiated neurovascular system comprised of pericytes, astrocytes, and endothelial cells. BBB compromise has been implicated in a number of neurodegenerative diseases, including meningitis, brain edema, epilepsy, Alzheimer's disease (AD), Parkinson's disease (PD), stroke, amyotrophic lateral sclerosis (ALS), and Multiple Sclerosis (MS; reviewed by Zlokovic B V. Neurovascular pathways to neurodegeneration in Alzheimer's disease and other disorders. Nat Rev Neurosci. 2011; 12:723-738).

Astrocytes are "polarized" cells in that they extend specialized membranous processes comprised of unique cellular machinery and membrane components that interact with specific cell types. For example, astrocytic processes proximal to cerebral microvessels or pia are characterized by a high density of the water channel, aquaporin 4 (Aqp4) (Neely J D, Amiry-Moghaddam M, Ottersen O P, Froehner S C, Agre P, Adams M E (2001) Syntrophin-dependent expression and localization of Aquaporin-4 water channel protein. Proc Natl Acad Sci USA 98, 14108-14113; Amiry-Moghaddam M, Otsuka T, Hurn P D, Traystman R J, Haug F M, Froehner S C, Adams M E, Neely J D, Agre P, Ottersen O P, Bhardwaj A (2003) An alpha-syntrophin-dependent pool of AQP4 in astroglial end-feet confers bidirectional water flow between blood and brain. Proc Natl Acad Sci USA 100, 2106-2111.). In contrast, astrocytic processes facing synaptic regions are enriched in glutamate transporters, while the density of Aqp4 is comparatively low (Nielsen S, Nagelhus E A, Amiry-Moghaddam M, Bourque C, Agre P, Ottersen O P (1997) Specialized membrane domains for water transport in glial cells: High-resolution immunogold cytochemistry of aquaporin-4 in rat brain. J Neurosci 17, 171-180; Chaudhry F A, Lehre K P, van Lookeren Campagne M, Ottersen O P, Danbolt N C, Storm-Mathisen J (1995) Glutamate transporters in glial plasma membranes: Highly differentiated localizations revealed by quantitative ultrastructural immunocytochemistry. Neuron 15, 711-720). Interestingly, astrocytic polarization is disrupted in a brain undergoing neurodegeneration. For example, in the setting of AD, Aqp4 staining intensities significantly decrease in regions with significant amyloid plaque burden. In fact, Yang and colleagues showed that the accumulation of amyloid pathology in tg-ArcSwe AD mice is coupled temporally and spatially to loss of astrocyte polarization (J Alzheimer's Dis. 2011; 27(4):711-22. doi: 10.3233/JAD-2011-110725; Loss of astrocyte polarization in the tg-ArcSwe mouse model of Alzheimer's disease. Yang J L, Lunde L K, Nuntagij P, Oguchi T, Camassa L M, Nilsson L N, Lannfelt L, Xu Y, Amiry-Moghaddam M, Ottersen O P, Torp R.).

Role of SEMA4D Signaling in Promoting Astrocyte Activation.

Given the association of SEMA4D receptor expression and the astrocyte activation marker GFAP, there exists the possibility that SEMA4D signaling can potentiate astrocyte activation, thereby providing a "feed-forward" mechanism during disease states. To examine the effects of SEMA4D on astrocyte activation, primary cultures of rat astrocytes were generated and treated with SEMA4D in isolation or in combination with thioacetamide (TAA) (Example 6 and FIG. 18A below), a well-known hepatotoxic and hepatocarcinogenic agent that has been shown to induce plexin-B1 expression in vivo (Lim, J. S., Jeong, S. Y., Hwang, J. Y., Park, H. J., Cho, J. W., & Yoon, S. (2006), or prostaglandin D2 (Example 6 and FIG. 18B below), a known activation factor produced by microglia in the CNS, Toxicogenomics Analysis on Thioacetamide-induced Hepatotoxicity in Mice. MOLECULAR & CELLULAR TOXICOLOGY, 2(2), 126-133.).

V. Treatment Methods Using Therapeutic Anti-SEMA4D Antibodies

Methods of the disclosure are directed to the use of anti-SEMA4D binding molecules, e.g., antibodies, including antigen-binding fragments, variants, and derivatives thereof, to treat a subject having a neurodegenerative disorder. In certain embodiments the endothelial cells express a SEMA4D receptor, in others the neuronal cells express a SEMA4D receptor, and in others both endothelial and neuronal cells express a SEMA4D receptor. In certain embodiments the receptor is Plexin-B1. Though the following discussion refers to administration of an anti-SEMA4D antibody, the methods described herein are also applicable to the antigen-binding fragments, variants, and derivatives of these anti-SEMA4D antibodies or other biologics or small molecules that retain the desired properties of the anti-SEMA4D antibodies of the disclosure, e.g., capable of specifically binding SEMA4D, e.g., human, mouse, or human and mouse SEMA4D, having SEMA4D neutralizing activity, and/or blocking the interaction of SEMA-4D with its receptor, e.g., Plexin-B1. In another embodiment, the methods refers to administration of an anti-SEMA4D antibody, the methods described herein can also refer to the administration of anti-Plexin-B 1 or anti-Plexin-B2 binding molecules that are capable of specifically binding Plexin-B1 and/or Plexin-B2 and blocking the interaction of SEMA-4D with one or both of its Plexin receptors, e.g., Plexin-B1 and/or Plexin-B2.

In one embodiment, treatment includes the application or administration of an anti-SEMA4D binding molecule, e.g., an antibody or antigen binding fragment thereof or other biologic or small molecule that binds and neutralizes SEMA4D as described herein to a patient, where the patient has, or has the risk of developing a neurodegenerative disorder. In another embodiment, treatment is also intended to include the application or administration of a pharmaceutical composition comprising the anti-SEMA4D binding molecule, e.g., an antibody or antigen binding fragment thereof to a patient, where the patient has, or has the risk of developing a neurodegenerative disorder.

The anti-SEMA4D binding molecules, e.g., antibodies or binding fragments thereof as described herein are useful for the treatment of various neurodegenerative disorders. In some embodiments, treatment of a neurodegenerative disorder is intended to induce an improvement in the symptoms associated with the disorder. In other embodiments, treatment of a neurodegenerative disorder is intended to reduce, retard or stop an increase in symptom manifestations. In other embodiments, treatment of a neurodegenerative disorder is intended to inhibit, e.g., suppress, retard, prevent, stop, or reverse a manifestation of symptoms. In other embodiments, treatment of a neurodegenerative disorder is intended to relieve to some extent one or more of the symptoms associated with the disorder. In these situations, the symptoms can be neuropsychiatric symptoms, cognitive symptoms, and/or motor dysfunction. In other embodiments, treatment of a neurodegenerative disorder is intended to reduce morbidity and mortality. In other embodiments, treatment of a neurodegenerative disorder is intended to improve quality of life.

In one embodiment, the disclosure relates to the use of anti-SEMA4D binding molecules, e.g., antibodies or antigen-binding fragments, variants, or derivatives thereof, as a medicament, in particular for use in the treatment of neurodegenerative disorders to improve the symptoms associated with the disorder.

In accordance with the methods of the present disclosure, at least one anti-SEMA4D binding molecule, e.g., an antibody or antigen binding fragment, variant, or derivative thereof, or other biologic or small molecule as defined elsewhere herein can be used to promote a positive therapeutic response with respect to the neurodegenerative disorder. A "positive therapeutic response" with respect to the neurodegenerative disorder is intended to include an improvement in the symptoms associated with the disorder. Such positive therapeutic responses are not limited to the route of administration and can comprise administration to the donor, the donor tissue (such as for example organ perfusion), the host, any combination thereof, and the like. In particular, the methods provided herein are directed to inhibiting, preventing, reducing, alleviating, or lessening the progression of a neurodegenerative disorder in a patient. Thus, for example, an improvement in the disorder can be characterized as an absence of clinically observable symptoms, a decrease in the incidence of clinically observable symptoms, or a change in the clinically observable symptoms.

Activities that change the symptoms associated with neurodegenerative disorders can be detected and measured using in vivo mouse models. In certain embodiments, a CVN mouse model can be employed. The CVN mouse incorporates mutations of AP precursor protein that are characteristic of familial Alzheimer's disease (AD) in three independent lineages together with a mutation that reproduces some of the conditions of brain inflammation associated with AD (Colton et al., J Alzheimer's Dis. 15:571-587, 2008; Van Nostrand et al., Stroke 41:S135-S138, 2010). The CVN model displays some of the primary pathologies associated with Alzheimer's disease: AP plaques, hyperphosphorylated tau causing neurofibrillary tangles and cell death (neuronal loss), and consistent spatial memory impairment and neurovascular deficits. In comparison to other mouse mutants used for modeling Alzheimer's disease, the CVN Mouse shows more Alzheimer related pathologies at an earlier age. In other embodiments, the YAC128 mouse model of Huntington's Disease (HD) can be employed. YAC128 mice express the full-length mutant human huntingtin gene (mHTT) and accurately recapitulate many of the signs and symptoms of HD. It should be appreciated that people skilled in the art will recognize that other models have been described and usefully employed for studies of disease mechanisms and treatment of symptoms in neurodegenerative disorders in the literature and that the present disclosure should not be limited to any one particular model.

The anti-SEMA4D binding molecules, e.g., antibodies or antigen binding fragments, variants, or derivatives thereof or other biologics or small molecules can be used in combination with at least one or more other treatments for neurodegenerative disorders; where the additional therapy is administered prior to, during, or subsequent to the anti-SEMA4D binding molecule, e.g., antibody or antigen binding fragment, variant, or derivative thereof, therapy. Thus, where the combined therapies comprise administration of an anti-SEMA4D binding molecule, e.g., an antibody or antigen binding fragment, variant, or derivative thereof, in combination with administration of another therapeutic agent, the methods of the disclosure encompass coadministration, using separate formulations or a single pharmaceutical formulation, with simultaneous or consecutive administration in either order.

To apply the methods and systems of the disclosure in certain embodiments, samples or images from a patient can be obtained before or, after, or both before and after the administration of a therapy comprising an effective amount of an isolated binding molecule that specifically binds to Semaphorin-4D (SEMA4D), to a subject determined to have a neurodegenerative disorder, or to a subject suspected of having a neurodegenerative disorder. In some cases, successive samples or images can be obtained from the patient after therapy has commenced, or after therapy has ceased, or both before and after therapy. Samples or images can, for example, be requested by a healthcare provider (e.g., a doctor) or healthcare benefits provider, obtained and/or processed by the same or a different healthcare provider (e.g., a nurse, a hospital) or a clinical laboratory, and after processing, the results can be forwarded to yet another healthcare provider, healthcare benefits provider, or the patient. Similarly, the measuring/determination of one or more scores, comparisons between scores, evaluation of the scores and treatment decisions can be performed by one or more healthcare providers, healthcare benefits providers, and/or clinical laboratories.

In certain aspects of any of the aforementioned procedures, the neurodegenerative disorder is selected from a group consisting of Alzheimer's disease, Parkinson's disease, Huntington's disease, Down syndrome, ataxia, amyotrophic lateral sclerosis (ALS), frontotemporal dementia (FTD), HIV-related cognitive impairment, CNS Lupus, mild cognitive impairment, or a combination thereof. In certain aspects of any of the aforementioned procedures, the neurodegenerative disorder is Alzheimer's disease or Huntington's disease, In some aspects, a healthcare provider can administer or instruct another healthcare provider to administer a therapy comprising an effective amount of an isolated binding molecule that specifically binds to Semaphorin-4D (SEMA4D), where the subject has, is determined to have, or is suspected to have, a neurodegenerative disorder. A healthcare provider can implement or instruct another healthcare provider or patient to perform the following actions: obtain a sample or image, process a sample or image, submit a sample or image, receive a sample or image, transfer a sample or image, analyze or measure a sample or image, quantify a sample or image, provide the results obtained after analyzing/measuring/quantifying a sample or image, receive the results obtained after analyzing/measuring/quantifying a sample or image, compare/score the results obtained after analyzing/measuring/quantifying one or more samples or images, provide the comparison/score from one or more samples, obtain the comparison/score from one or more samples or images, administer a therapy, e.g., an effective amount of an isolated binding molecule that specifically binds to Semaphorin-4D (SEMA4D), commence the administration of a therapy, cease the administration of a therapy, continue the administration of a therapy, temporarily interrupt the administration of a therapy, increase the amount of an administered therapeutic agent, decrease the amount of an administered therapeutic agent, continue the administration of an amount of a therapeutic agent, increase the frequency of administration of a therapeutic agent, decrease the frequency of administration of a therapeutic agent, maintain the same dosing frequency on a therapeutic agent, replace a therapy or therapeutic agent by at least another therapy or therapeutic agent, combine a therapy or therapeutic agent with at least another therapy or additional therapeutic agent.

In some aspects, a healthcare benefits provider can authorize or deny, for example, collection of a sample, processing of a sample, submission of a sample, receipt of a sample, transfer of a sample, analysis or measurement a sample, quantification a sample, provision of results obtained after analyzing/measuring/quantifying a sample, transfer of results obtained after analyzing/measuring/quantifying a sample, comparison/scoring of results obtained after analyzing/measuring/quantifying one or more samples, transfer of the comparison/score from one or more samples, administration of a therapy or therapeutic agent, commencement of the administration of a therapy or therapeutic agent, cessation of the administration of a therapy or therapeutic agent, continuation of the administration of a therapy or therapeutic agent, temporary interruption of the administration of a therapy or therapeutic agent, increase of the amount of administered therapeutic agent, decrease of the amount of administered therapeutic agent, continuation of the administration of an amount of a therapeutic agent, increase in the frequency of administration of a therapeutic agent, decrease in the frequency of administration of a therapeutic agent, maintain the same dosing frequency on a therapeutic agent, replace a therapy or therapeutic agent by at least another therapy or therapeutic agent, or combine a therapy or therapeutic agent with at least another therapy or additional therapeutic agent.

In certain aspects of any of the aforementioned procedures, the neurodegenerative disorder is selected from a group consisting of Alzheimer's disease, Parkinson's disease, Huntington's disease, Down syndrome, ataxia, amyotrophic lateral sclerosis (ALS), frontotemporal dementia (FTD), HIV-related cognitive impairment, CNS Lupus, mild cognitive impairment, or a combination thereof. In certain aspects of any of the aforementioned procedures, the neurodegenerative disorder is Alzheimer's disease or Huntington's disease.

In addition, a healthcare benefits provider can, e.g., authorize or deny the prescription of a therapy, authorize or deny coverage for therapy, authorize or deny reimbursement for the cost of therapy, determine or deny eligibility for therapy, etc.

In some aspects, a clinical laboratory can, for example, collect or obtain a sample, process a sample, submit a sample, receive a sample, transfer a sample, analyze or measure a sample, quantify a sample, provide the results obtained after analyzing/measuring/quantifying a sample, receive the results obtained after analyzing/measuring/quantifying a sample, compare/score the results obtained after analyzing/measuring/quantifying one or more samples, provide the comparison/score from one or more samples, obtain the comparison/score from one or more samples, or other related activities.

In certain aspects of any of the aforementioned procedures, the neurodegenerative disorder is selected from a group consisting of Alzheimer's disease, Parkinson's disease, Huntington's disease, Down syndrome, ataxia, amyotrophic lateral sclerosis (ALS), frontotemporal dementia (FTD), HIV-related cognitive impairment, CNS Lupus, mild cognitive impairment, or a combination thereof. In certain aspects of any of the aforementioned procedures, the neurodegenerative disorder is Alzheimer's disease or Huntington's disease.

In certain aspects, any of the aforementioned procedures can be used to determine if a subject has a neurodegenerative disorder. In certain aspects, the neurodegenerative disorder is selected from a group consisting of Alzheimer's disease, Parkinson's disease, Huntington's disease, Down syndrome, ataxia, amyotrophic lateral sclerosis (ALS), frontotemporal dementia (FTD), HIV-related cognitive impairment, CNS Lupus, mild cognitive impairment, or a combination thereof. In certain aspects of any of the aforementioned procedures, the neurodegenerative disorder is Alzheimer's disease or Huntington's disease, In some aspects, a healthcare provider, clinical laboratory, or other entity can, for example, collect or obtain an image, process an image, submit an image, receive an image, transfer an image, analyze or measure an image, quantify an image, provide the results obtained after analyzing/measuring/quantifying an image, receive the results obtained after analyzing/measuring/quantifying an image, compare/score the results obtained after analyzing/measuring/quantifying one or more images, provide the comparison/score from one or more images, obtain the comparison/score from one or more images, or other related activities. Images that can be used in such aspects include, but are not limited to, images obtained by angiography, ultrasound, computed tomography (CT), magnetic resonance imaging (MRI), positron emission tomography (PET), optical coherence tomography (OCT), near-infrared spectroscopy (NIRS), and NIR fluorescence. In certain embodiments, imaging techniques that have been described in the literature can be used (Tardif et al. Circ Cardiovasc Imaging 4:319-333 (2011)).

VI. Pharmaceutical Compositions and Administration Methods

Methods of preparing and administering anti-SEMA4D binding molecules, e.g., antibodies, or antigen-binding fragments, variants, or derivatives thereof to a subject in need thereof are well known to or are readily determined by those skilled in the art. The route of administration of the anti-SEMA4D binding molecule, e.g, antibody, or antigen-binding fragment, variant, or derivative thereof, can be, for example, oral, parenteral, by inhalation or topical. The term parenteral as used herein includes, e.g., intravenous, intraarterial, intraperitoneal, intramuscular, subcutaneous, rectal, or vaginal administration. While all these forms of administration are clearly contemplated as being within the scope of the disclosure, an example of a form for administration would be a solution for injection, in particular for intravenous or intraarterial injection or drip. A suitable pharmaceutical composition for injection can comprise a buffer (e.g. acetate, phosphate or citrate buffer), a surfactant (e.g. polysorbate), optionally a stabilizer agent (e.g. human albumin), etc. However, in other methods compatible with the teachings herein, anti-SEMA4D binding molecules, e.g., antibodies, or antigen-binding fragments, variants, or derivatives thereof can be delivered directly to the site of the adverse cellular population thereby increasing the exposure of the diseased tissue to the therapeutic agent.

As discussed herein, anti-SEMA4D binding molecules, e.g., antibodies, or antigen-binding fragments, variants, or derivatives thereof can be administered in a pharmaceutically effective amount for the in vivo treatment of neurodegenerative disorders. In this regard, it will be appreciated that the disclosed binding molecules can be formulated so as to facilitate administration and promote stability of the active agent. In certain embodiments, pharmaceutical compositions in accordance with the present disclosure comprise a pharmaceutically acceptable, non-toxic, sterile carrier such as physiological saline, non-toxic buffers, preservatives and the like. For the purposes of the instant application, a pharmaceutically effective amount of an anti-SEMA4D binding molecule, e.g., an antibody, or antigen-binding fragment, variant, or derivative thereof, shall be held to mean an amount sufficient to achieve effective binding to a target and to achieve a benefit, e.g., improve the symptoms associated with a neurodegenerative disorder.

The pharmaceutical compositions used in this disclosure comprise pharmaceutically acceptable carriers, including, e.g., ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol, and wool fat.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include, e.g., water, alcoholic/aqueous solutions, emulsions or suspensions, including saline and buffered media. In the subject disclosure, pharmaceutically acceptable carriers include, but are not limited to, 0.01-0.1 M, e.g., about 0.05 M phosphate buffer or 0.8% saline. Other common parenteral vehicles include sodium phosphate solutions, Ringer's dextrose, dextrose and sodium chloride, lactated Ringer's, or fixed oils. Intravenous vehicles include fluid and nutrient replenishers, electrolyte replenishers, such as those based on Ringer's dextrose, and the like. Preservatives and other additives can also be present such as, for example, antimicrobials, antioxidants, chelating agents, and inert gases and the like.

More particularly, pharmaceutical compositions suitable for injectable use include sterile aqueous solutions (where water soluble) or dispersions and sterile powders for the extemporaneous preparation of sterile injectable solutions or dispersions. In such cases, the composition must be sterile and should be fluid to the extent that easy syringability exists. It should be stable under the conditions of manufacture and storage and can be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Suitable formulations for use in the therapeutic methods disclosed herein are described in Remington's Pharmaceutical Sciences (Mack Publishing Co.) 16th ed. (1980).

Prevention of the action of microorganisms can be achieved by various antibacterial and antifungal agents, for example, parabens, chlorobutanol, phenol, ascorbic acid, thimerosal and the like. In many cases, isotonic agents can be included, for example, sugars, polyalcohols, such as mannitol, sorbitol, or sodium chloride. Prolonged absorption of the injectable compositions can be brought about by including in the composition an agent which delays absorption, for example, aluminum monostearate and gelatin.

In any case, sterile injectable solutions can be prepared by incorporating an active compound (e.g., an anti-SEMA4D antibody, or antigen-binding fragment, variant, or derivative thereof, by itself or in combination with other active agents) in the required amount in an appropriate solvent with one or a combination of ingredients enumerated herein, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, methods of preparation include vacuum drying and freeze-drying, which yield a powder of an active ingredient plus any additional desired ingredient from a previously sterile-filtered solution thereof. The preparations for injections are processed, filled into containers such as ampoules, bags, bottles, syringes or vials, and sealed under aseptic conditions according to methods known in the art. Further, the preparations can be packaged and sold in the form of a kit. Such articles of manufacture can have labels or package inserts indicating that the associated compositions are useful for treating a subject suffering from, or predisposed to a disease or disorder.

Parenteral formulations can be a single bolus dose, an infusion or a loading bolus dose followed with a maintenance dose. These compositions can be administered at specific fixed or variable intervals, e.g., once a day, or on an "as needed" basis.

Certain pharmaceutical compositions used in this disclosure can be orally administered in an acceptable dosage form including, e.g., capsules, tablets, aqueous suspensions or solutions. Certain pharmaceutical compositions also can be administered by nasal aerosol or inhalation. Such compositions can be prepared as solutions in saline, employing benzyl alcohol or other suitable preservatives, absorption promoters to enhance bioavailability, and/or other conventional solubilizing or dispersing agents.

The amount of an anti-SEMA4D binding molecule, e.g., antibody, or fragment, variant, or derivative thereof, to be combined with the carrier materials to produce a single dosage form will vary depending upon the host treated and the particular mode of administration. The composition can be administered as a single dose, multiple doses or over an established period of time in an infusion. Dosage regimens also can be adjusted to provide the optimum desired response (e.g., a therapeutic or prophylactic response).

In keeping with the scope of the present disclosure, anti-SEMA4D antibodies, or antigen-binding fragments, variants, or derivatives thereof can be administered to a human or other animal in accordance with the aforementioned methods of treatment in an amount sufficient to produce a therapeutic effect. The anti-SEMA4D antibodies, or antigen-binding fragments, variants or derivatives thereof can be administered to such human or other animal in a conventional dosage form prepared by combining the antibody of the disclosure with a conventional pharmaceutically acceptable carrier or diluent according to known techniques. It will be recognized by one of skill in the art that the form and character of the pharmaceutically acceptable carrier or diluent is dictated by the amount of active ingredient with which it is to be combined, the route of administration and other well-known variables. Those skilled in the art will further appreciate that a cocktail comprising one or more species of anti-SEMA4D binding molecules, e.g., antibodies, or antigen-binding fragments, variants, or derivatives thereof, of the disclosure can be used.

By "therapeutically effective dose or amount" or "effective amount" is intended an amount of anti-SEMA4D binding molecule, e.g., antibody or antigen binding fragment, variant, or derivative thereof, that when administered brings about a positive therapeutic response with respect to treatment of a patient with a disease to be treated. In the case of a neurodegenerative disorder, a positive therapeutic response can alleviate symptoms of the disorder; decrease, reduce, retard or stop the incidence of symptoms; decrease, reduce, retard the severity of symptoms; inhibit, e.g., suppress, retard, prevent, stop, or reverse the manifestation of symptoms; relieve to some extent one or more of the symptoms associated with the disorder; reduce morbidity and mortality; improve quality of life; or a combination of such effects.

Therapeutically effective doses of the compositions of the present disclosure, for the decrease in the incidence of symptoms, vary depending upon many different factors, including means of administration, target site, physiological state of the patient, whether the patient is human or an animal, other medications administered, and whether treatment is prophylactic or therapeutic. In certain embodiments the patient is a human, but non-human mammals including transgenic mammals can also be treated. Treatment dosages can be titrated using routine methods known to those of skill in the art to optimize safety and efficacy.

The amount of at least one anti-SEMA4D binding molecule, e.g., antibody or binding fragment, variant, or derivative thereof, to be administered is readily determined by one of ordinary skill in the art without undue experimentation given the present disclosure. Factors influencing the mode of administration and the respective amount of at least one anti-SEMA4D binding molecule, e.g., antibody, antigen-binding fragment, variant or derivative thereof include, but are not limited to, the severity of the disease, the history of the disease, and the age, height, weight, health, and physical condition of the individual undergoing therapy. Similarly, the amount of anti-SEMA4D binding molecule, e.g., antibody, or fragment, variant, or derivative thereof, to be administered will be dependent upon the mode of administration and whether the subject will undergo a single dose or multiple doses of this agent.

The disclosure also provides for the use of an anti-SEMA4D binding molecule, e.g., antibody of the disclosure, or antigen-binding fragment, variant, or derivative thereof, in the manufacture of a medicament for treating a subject for treating a neurodegenerative disorder, wherein the medicament is used in a subject that has been pretreated with at least one other therapy. By "pretreated" or "pretreatment" is intended the subject has received one or more other therapies (e.g., been treated with at least one other neurodegenerative therapy) prior to receiving the medicament comprising the anti-SEMA4D binding molecule, e.g., antibody or antigen-binding fragment, variant, or derivative thereof "Pretreated" or "pretreatment" includes subjects that have been treated with at least one other therapy within 2 years, within 18 months, within 1 year, within 6 months, within 2 months, within 6 weeks, within 1 month, within 4 weeks, within 3 weeks, within 2 weeks, within 1 week, within 6 days, within 5 days, within 4 days, within 3 days, within 2 days, or even within 1 day prior to initiation of treatment with the medicament comprising the anti-SEMA4D binding molecule, for example, the monoclonal antibodies VX15/2503, 67, or 76 disclosed herein, or antigen-binding fragment, variant, or derivative thereof. It is not necessary that the subject was a responder to pretreatment with the prior therapy or therapies. Thus, the subject that receives the medicament comprising the anti-SEMA4D binding molecule, e.g., an antibody or antigen-binding fragment, variant, or derivative thereof could have responded, or could have failed to respond, to pretreatment with the prior therapy, or to one or more of the prior therapies where pretreatment comprised multiple therapies.

The practice of the present disclosure will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Sambrook et al., ed. (1989) Molecular Cloning A Laboratory Manual (2nd ed.; Cold Spring Harbor Laboratory Press); Sambrook et al., ed. (1992) Molecular Cloning: A Laboratory Manual, (Cold Springs Harbor Laboratory, NY); D. N. Glover ed., (1985) DNA Cloning, Volumes I and II; Gait, ed. (1984) Oligonucleotide Synthesis; Mullis et al. U.S. Pat. No. 4,683,195; Hames and Higgins, eds. (1984) Nucleic Acid Hybridization; Hames and Higgins, eds. (1984) Transcription And Translation; Freshney (1987) Culture Of Animal Cells (Alan R. Liss, Inc.); Immobilized Cells And Enzymes (IRL Press) (1986); Perbal (1984) A Practical Guide To Molecular Cloning; the treatise, Methods In Enzymology (Academic Press, Inc., N.Y.); Miller and Calos eds. (1987) Gene Transfer Vectors For Mammalian Cells, (Cold Spring Harbor Laboratory); Wu et al., eds., Methods In Enzymology, Vols. 154 and 155; Mayer and Walker, eds. (1987) Immunochemical Methods In Cell And Molecular Biology (Academic Press, London); Weir and Blackwell, eds., (1986) Handbook Of Experimental Immunology, Volumes I-IV; Manipulating the Mouse Embryo, Cold Spring Harbor Laboratory Press, Cold Spring Harbor, N.Y., (1986); and in Ausubel et al. (1989) Current Protocols in Molecular Biology (John Wiley and Sons, Baltimore, Md.).

General principles of antibody engineering are set forth in Borrebaeck, ed. (1995) Antibody Engineering (2nd ed.; Oxford Univ. Press). General principles of protein engineering are set forth in Rickwood et al., eds. (1995) Protein Engineering, A Practical Approach (IRL Press at Oxford Univ. Press, Oxford, Eng.). General principles of antibodies and antibody-hapten binding are set forth in: Nisonoff (1984) Molecular Immunology (2nd ed.; Sinauer Associates, Sunderland, Mass.); and Steward (1984) Antibodies, Their Structure and Function (Chapman and Hall, New York, N.Y.). Additionally, standard methods in immunology known in the art and not specifically described are generally followed as in Current Protocols in Immunology, John Wiley & Sons, New York; Stites et al., eds. (1994) Basic and Clinical Immunology (8th ed; Appleton & Lange, Norwalk, Conn.) and Mishell and Shiigi (eds) (1980) Selected Methods in Cellular Immunology (W.H. Freeman and Co., NY).

Standard reference works setting forth general principles of immunology include Current Protocols in Immunology, John Wiley & Sons, New York; Klein (1982) J., Immunology: The Science of Self-Nonself Discrimination (John Wiley & Sons, NY); Kennett et al., eds. (1980) Monoclonal Antibodies, Hybridoma: A New Dimension in Biological Analyses (Plenum Press, NY); Campbell (1984) "Monoclonal Antibody Technology" in Laboratory Techniques in Biochemistry and Molecular Biology, ed. Burden et al., (Elsevere, Amsterdam); Goldsby et al., eds. (2000) Kuby Immunology (4th ed.; H. Freemand & Co.); Roitt et al. (2001) Immunology (6th ed.; London: Mosby); Abbas et al. (2005) Cellular and Molecular Immunology (5th ed.; Elsevier Health Sciences Division); Kontermann and Dubel (2001) Antibody Engineering (Springer Verlang); Sambrook and Russell (2001) Molecular Cloning: A Laboratory Manual (Cold Spring Harbor Press); Lewin (2003) Genes VIII (Prentice Hall 2003); Harlow and Lane (1988) Antibodies: A Laboratory Manual (Cold Spring Harbor Press); Dieffenbach and Dveksler (2003) PCR Primer (Cold Spring Harbor Press).

All of the references cited above, as well as all references cited herein, are incorporated herein by reference in their entireties.

The following examples are offered by way of illustration and not by way of limitation.

EXAMPLES

Example 1: Testing the Effect of an Anti-SEMA4D Binding Molecule, e.g., an Antibody or Antigen-Binding Fragment, Variant, or Derivative Thereof, e.g., VX15/2503, 67, or 76 on Alzheimer's Disease (AD) in the CVN Mouse Model Experimental Design.

The CVN model was used to study the effect of anti-SEMA4D antibody (e.g., MAb 67) on the pathologies and symptoms associated with AD. The CVN mouse incorporates mutations of human Aβ precursor protein that are characteristic of familial Alzheimer's disease (AD) in three independent lineages together with a deletion of a gene (nitric oxide synthase-2) to promote neuroinflammatory mechanisms associated with AD (Colton et al., *J Alzheimer's Dis.* 15:571-587, 2008; Van Nostrand et al., Stroke 41:S135-S138, 2010).

The basic experimental design is shown in FIG. 1. Alzheimer's disease prone CVN mice (obtained from Charles River) were used to test the effect of an anti-SEMA4D binding molecule on AD. At 10 weeks of age, the mice were bled to obtain baseline serology levels. Between 10-12 weeks of age, the mice underwent behavioral pretesting to ensure they were capable of participating in the study. Following randomization, the CVN mice were treated weekly with anti-SEMA4D (Mab-67) or isotype control (MAb 2B8) antibody (30 mg/kg, i.v.) from week 26 to 38 at which time they were administered several behavioral tests. The behavioral tests were the open field test and the radial arm water maze.

Open Field Test—

Exploratory activity of the animal is studied in open field test at 10 and 38 weeks of age for possible treatment induced hypo- or hyperactivity (control test) or other effect. Mice are brought to the experimental room for at least 30 min acclimation to the experimental room conditions prior to testing. Activity chambers (Med Associates Inc, St Albans, Vt.; 27×27×20.3 cm) are equipped with IR beams. Mice are placed in the center of the chamber and their behavior is recorded for 30 min in 5-minute bins. Quantitative analysis is performed on the following five dependent measures: total locomotion, locomotion in the center of the open field, rearing rate in the center, total rearing frequency and velocity. Animals are tested at low-stress conditions where the light is lowered to approximately 10-30 lux of red light.

Radial Arm Water Maze—

At 11 and 39 weeks of age mice are brought to the experimental room for at least 30 min acclimation to the experimental room conditions prior to testing. Two-day radial-arm water maze has been described in detail previously (Alamed et al. 2006). Briefly, a six-arm maze is submerged in a pool of water, and a platform is placed at the end of one arm. The mouse receives 15 trials per day for 2 d and on each trial is started in a different arm while the arm containing the platform remains the same for each mouse. The platform location of which remains constant over the 2 d for each mouse at a given age, but this location changes for each mouse between the 11 and 40 weeks of age testing time point. Using visual cues around the room, the mouse learns the position of the escape platform. The first 10 trials are considered training and alternate between a visible and a hidden platform. The final trials for day 1 and all trials on day 2 use a hidden platform. The number of errors (incorrect arm entries) was counted over a 1 min period. The errors are averaged over three trials resulting in 10 blocks for the 2 d period.

Following the conclusion of behavioral testing, mice were sacrificed, and brain tissues were processed for formalin-fixed paraffin-embedded (FFPE) immunohistochemistry. In view of reports of a role for SEMA4D in the induction of inhibitory GABAergic synapses (Kuzirian et al., *J Neuroscience*, 33:8961-8973• 8961, 2013) the density of vesicles and intensity of expression of Vesicular GABA Transporter (VGAT) was determined in the Dentate Gyms of treated CVN mice. The Dentate Gyms is one of a few major centers of continued neurogenesis in the adult CNS and is thought to play a role in memory formation and retention. For all tests, statistical analysis was performed using the 2-way ANOVA test.

Anti-SEMA4D Reduces Anxiety-Like Behavior.

Exploratory activity was studied in groups of 12 AD prone CVN mice treated with anti-SEMA4D or isotype control. An open field test was administered at 38 weeks of age for possible treatment-induced effects on locomotor activity and anxiety-like behavior. Mice were placed in the center of a lighted chamber and their behavior was recorded for 30 min in six 5-minute time bins. Quantitative analysis was performed for total locomotion (FIG. 2A) and locomotion in the center of the open field (FIG. 2B), which, as is known in the art, is a measure of anxiety-related behavior.

The results showed that AD prone CVN mice treated weekly with anti-SEMA4D antibody manifest greater open field exploration and less anxiety-like behavior (incursions into the center of the field) than mice treated with control MAb 2B8. These results are shown in FIG. 2A and FIG. 2B.

Anti-SEMA4D Improves Spatial Memory.

At 39 weeks of age, CVN mice treated with anti-SEMA4D or 2B8 isotype control (n=9-13/group) were tested over 2-days in a radial-arm water maze (Alamed et al. 2006, shown in FIG. 3A). Briefly, each mouse received 15 trials per day (3 trials per block) on each of two consecutive days. Each trial was started from a different arm, while the arm containing the platform remained the same for each trial. Trial blocks on Day 1 alternated between a visible and hidden platform for training purposes. All trials on Day 2 were performed with a hidden platform to assess spatial memory. Day 1 was a training/learning period and on day 2 the latency to find the platform was recorded.

The results showed that anti-SEMA4D antibody (MAb 67) administration leads to a measurable decrease in latency suggesting improved spatial memory as compared to the control (MAb 2B8-treated) cohort. The results are shown in FIG. 3B.

Anti-SEMA4D Decreases GABAergic Synapses.

FFPE brain tissue sections from Mab-67 or MAb-2B8 treated CVN and WT mice (n=9-13/group) were stained with anti-VGAT antibody to detect GABAergic synaptic vesicles. Percentages of VGAT-positive vesicle signal and VGAT signal intensities per vesicle were quantified within the dentate gyrus of all animals and normalized to total dentate gyrus area scanned.

The results showed that anti-SEMA4D antibody treatment of CVN AD mice leads to a trend of decreasing density of VGAT positive vesicles (FIG. 4A) and a statistically significant decrease in VGAT staining intensity level per vesicle (FIG. 4B), a finding that suggests a role for SEMA4D in modulating GABAergic signaling in vivo and can provide mechanistic insight into the behavioral effects observed in MAb 67 treated CVN mice. GABAergic signaling is associated with a heterogeneous class of inhibitory neurons. As demonstrated in FIGS. 15A, 15B, 15C, and 15D of Example 6 below, more significant effects of treatment with anti-SEMA4D antibody on density of inhibitory neurons are observed when analysis is focused on the subset of somatostatin-, NPY-, or NPY2R-positive neurons.

Example 2: Testing the Effect of an Anti-SEMA4D Binding Molecule, e.g., an Antibody or Antigen-Binding Fragment, Variant, or Derivative Thereof, e.g., MAbs VX15/2503 or 67 on Huntington's Disease (HD) in the YAC128 Mouse Model Experimental Design.

A second experiment employing an in vivo YAC128 model was performed to study the effect of anti-SEMA4D antibody on the pathologies and symptoms associated with HD. The basic experimental design was similar to that shown in Example 1, and FIG. 1, above, but MAb (antibody) dosing in this case was performed weekly from week 6 to week 47 with between 13 and 22 YAC128 or WT mice per group. The YAC128 mice were bred and maintained at University of British Columbia, Centre for Molecular Medicine and Therapeutics.

Anti-SEMA4D Reduces Anxiety-Like Behavior in the YAC128 Mouse Model.

To assess anxiety during open-field exploration, MAb-treated mice were placed in the lower left corner of a 50×50 cm open grey acrylic box with 20 cm tall sides in a room brightly lit by fluorescent ceiling lights. Open-field activity was recorded for 10 min by a ceiling-mounted video camera. Entries into (FIG. 5A) and time spent in the center of the field (FIG. 5B) were scored as a measure of anxiety-like behavior.

In contrast to control treated animals where YAC128 mice manifest greater anxiety-like behavior in open field exploration than wild type (WT) mice, there is no difference between WT and YAC128 mice treated with anti-SEMA4D antibody (MAb 67) indicating that MAb-67 ameliorates anxiety-like behavior in YAC128 mice. These results are shown in FIG. 5A and FIG. 5B.

Anti-SEMA4D Improves Spatial Memory in the YAC128 Mouse Model.

To assess preference for a known object in a novel location, two different novel objects were placed in the upper left and right hand corners of an open field box. Anti-SEMA4D-treated mice were introduced to the box in the lower left corner and recorded for 5 minutes (min) by a ceiling-mounted video camera, during which time the number of investigations of the two novel objects were scored (Trial 1, FIG. 6A). Mice were then removed from the box for 5 min, and the object at the top right corner of the box was moved to the lower right corner of the box. Mice were reintroduced to the box and recorded for an additional 5 min (Trial 2, FIG. 6B). The percentage of the investigations, or nose pokes, to the target object (the one in the new location) relative to all nose pokes was computed.

In contrast to control or Mab 67-treated wild type (WT) animals that preferentially explore an object in a novel location in Trial 2, control-treated YAC128 mice do not recognize or show preference for the object in a novel location. Treatment with anti-SEMA4D antibody restores normal novel object preference in YAC128 mice (p<0.01). This suggests that spatial memory in YAC128 mice was improved by Mab-67 treatment so that they recognized that an object was in a novel location. The results are shown in FIG. 6A and FIG. 6B.

Anti-SEMA4D Prevents Cortical and Corpus Callosum Degeneration in YAC128 Mice.

Free-floating brain tissue sections from 12 month-old MAb-treated YAC128 and WT mice (n=13-21/group) were stained with anti-NeuN antibody. Cortical (FIG. 7A) and corpus callosum (FIG. 7B) volumes were determined by tracing the perimeter of the defined structure in serial sections using StereoInvestigator software (Microbrightfield) and volumes were determined using the Cavalieri principle.

The results show that treatment with anti-SEMA4D antibody inhibits the normal disease related reduction in cortical and corpus callosum volume in YAC128 mice at 12 months of age. The results are shown in FIG. 7A and FIG. 7B.

Mab 67 Prevents Testicular Degeneration in YAC128 Mice.

Testicular degeneration is observed in male HD patients and is recapitulated in male YAC128 mice. As shown in FIG. 8, treatment with anti-SEMA4D antibody prevents testicular degeneration in 12 month-old YAC128 mice. It is possible that the effects of disease and anti-SEMA4D antibody on both brain and testis reflect a common dependence on intracellular actin-dependent transport mechanisms in the normal function of these tissues.

Example 3: Examining Expression Patterns of SEMA4D, Plexin-B1, Plexin-B2 and CD72 in the Rat CNS To visualize the cell types within the CNS that express SEMA4D and its receptors plexin-B1, plexin-B2, and CD72, co-immunohistochemistry was performed on coronal spinal cord sections from naïve rats (FIG. 9A, FIG. 9B, FIG. 9C, FIG. 9D, FIG. 9E, FIG. 9F, FIG. 9G, FIG. 9H, FIG. 9I, FIG. 9J, FIG. 9K, FIG. 9L, FIG. 9M, FIG. 9N, FIG. 9O, and FIG. 9P). Co-staining for the oligodendrocyte precursor cell marker, Nkx2.2, and SEMA4D (FIG. 9A-9C), plexin-B1 and the astrocytic marker, GFAP (FIG. 9E-9G), plexin-B1 and CD72 (FIG. 9I-9K), and plexin-B1 and the microglial marker, Iba1 (FIG. 9M-9O) was performed on spinal cord sections from naïve rats. In addition, all sections were stained with DAPI to visualize cellular nuclei (FIG. 9D, FIG. 9H, FIG. 9L, and FIG. 9P). Slides were imaged at 60× magnification using an EXi-Aqua-14 bit camera coupled to an Olympus Ix50 microscope.

The results in FIG. 9A-9P show that within the normal CNS, SEMA4D is robustly expressed on Nkx2.2-positive oligodendrocyte precursors, while its receptors, plexin-B1, plexin-B2 (data not shown), and CD72, are expressed on multiple cell types and are especially prominent on Glial Fibrillary Acidic Protein (GFAP)-positive astrocytes.

Example 4: Characterizing the Expression Patterns of Plexin-B1 and Plexin-B2 Receptors in the CVN Alzheimer's Disease Mouse Model Homozygous bigenic CVN AD mice exhibit classical amyloid pathology and glial activation in the subiculum as compared to age-matched wild-type mice. Expression patterns of plexin-B1 were examined in the CVN mouse model of Alzheimer's disease. CVN (also known as APPSwDI/ NOS2−/−) bigenic mice harbor the amyloid precursor protein Swedish-Dutch-Iowa mutant (APPSwDI) transgene and a targeted "null" mutation of the nitric oxide synthase 2 (Nos2, or inducible NOS, iNOS) locus. At 41 weeks of age, CVN and wild-type control mice were sacrificed and processed for DAB immunohistochemistry. The results are shown in FIG. 10, with the wild-type mouse sections in the top panels and the CVN mouse sections in the bottom panels). Sections were separately stained for amyloid-beta 1-42 peptide (top and bottom panels at left), microglial marker Iba1 (top and bottom center panels), or astrocyte marker GFAP (top and bottom panels at right). Slides were imaged at 20× magnification using a Retiga QICAM-12 bit camera coupled to an Olympus Ix50 microscope.

The results in FIG. 10 show that homozygous bigenic CVN mice (APPSwDI/NOS2−/−) develop classic amyloid pathology, microglial activation, and astrogliosis (bottom panels).

Activated Astrocytes in CVN AD Mice Exhibit Enhanced Plexin-B1 Expression as Compared to Age-Matched Wild-Type Mice.

At 41 weeks of age, CVN and wild-type control mice were sacrificed and processed for fluorescent co-immunohistochemistry (FIG. 11A). Sections were separately stained for the SEMA4D receptor plexin-B1 and astrocyte marker GFAP, and DAPI to visualize cellular nuclei. Composite images are shown in the left-most panels. Slides were imaged at 60× magnification using an EXi-Aqua-14 bit camera coupled to an Olympus Ix50 microscope.

As shown in FIG. 11A, co-immunohistochemical analyses of plexin-B1 (second panels from left) and GFAP-positive astrocytes (third panels from left) within the brains of CVN and age-matched wild-type mice demonstrates that astrocytic activation, as evidenced by increased GFAP marker staining, positively correlates with enhanced co-registered plexin-B1 expression, suggesting SEMA4D/ plexin signaling participates in the process of astrocyte activation.

Inhibiting SEMA4D Signaling in CVN AD Mice Restores Plexin-B2 Expression as Compared to Age-Matched Wild-Type Mice.

To determine if blocking SEMA4D signaling in CVN AD mice would impact the expression of plexin-B1 and/or its alternate cognate receptor, plexin-B2, in brain regions affected early in AD pathogenesis, 26 week-old CVN and wild-type control mice were injected weekly with 30 mg/kg anti-SEMA4D monoclonal antibody (67-2) or control IgG (2B8) intravenously for 13 weeks. At 41 weeks of age, mice were sacrificed and brain tissue sections from MAb-treated mice were stained with anti-plexin-B1 or anti-plexin-B2 to detect whether anti-SEMA4D treatment altered cognate receptor expression in the setting of ongoing AD-related pathogenesis. Percentage of plexin-B1 and plexin-B2-positive signals were quantified within the subiculum of all animals and normalized to total subiculum area scanned.

As shown in FIG. 11B, anti-SEMA4D antibody treatment of CVN AD mice lead to a restoration in plexin-B2 (right graph) staining intensity levels to those quantified in WT control mice, but no significant change in plexin-B1 levels (left graph) relative to age-matched CVN AD control mice. These results suggest antibody-mediated SEMA4D inhibition selectively leads to destabilization of plexin-B2 and/or impedes a SEMA4D-driven feed-forward mechanism that selectively promotes plexin-B2 expression.

Example 5: Characterizing the Expression Patterns of Plexin-B2 Receptor in a YAC128 Huntington's Disease Mouse Model YAC128 mice express the full-length mutant human huntingtin gene (mHTT) and accurately recapitulate many of the signs and symptoms of HD (see also Example 2). Activated astrocytes in YAC128 Huntington disease mice exhibit enhanced plexin-B2 expression as compared to age-matched wild-type mice. At 12 months of age, YAC128 mice and wild-type control mice were sacrificed and processed for fluorescent co-immunohistochemistry (FIG. 12). Sections were co-stained for plexin-B2 (Plexin-B2, third panels from left), astrocyte marker GFAP (second panels from left) and DAPI to visualize cellular nuclei. Composite images are shown in the left-most panels. Slides were imaged at 60× magnification using an EXi-Aqua-14 bit camera coupled to an Olympus Ix50 microscope.

As shown in FIG. 12, co-immunohistochemical analyses of plexin-B2 and GFAP-positive astrocytes within the brains of YAC128 and wild-type mice demonstrates that astrocytic activation, as evidenced by increased GFAP marker staining, again positively correlates with co-registered SEMA4D receptor expression. Plexin-B2, whose best characterized ligand is SEMA4C, also has an intermediate affinity for SEMA4D (Azzarelli R, et al. An antagonistic interaction between PlexinB2 and Rnd3 controls RhoA activity and cortical neuron migration. *Nature Commun.* 2014; DOI: 10.1038/ncomms4405)

Example 6: Examining the Mechanisms by which SEMA4D Signaling can Modulate Astrocyte Function The correlation between enhanced SEMA4D receptor expression and astrocytic activation in the setting of both AD and HD neurodegenerative disease suggests that SEMA4D signaling plays a role in astrocyte function and/or dysfunction. While not wishing to be bound by theory, this example provides evidence that SEMA4D signaling can participate in the regulation of astrocytic function during responses to CNS injury, whether from acute or chronic stimuli. A schematic model supported by the data is depicted in FIG. 13, which shows three mechanisms by which SEMA4D signaling can potentially modulate astrocyte function. These three mechanisms are discussed below.

Role of Astrocytes and OPC Support.

Plexin+ astrocytic processes interdigitate between SEMA4D+ NKX2.2+ oligodendrocyte precursor cells (OPCs) and provide trophic support. In CNS disease, activated astrocytes upregulate Plexin expression and retract processes via SEMA4D signaling. Locally, this loss of astrocyte:OPC proximity can result in diminished trophic support and increased chemotaxis-driven OPC movement toward regions of damage, while lack of astrocytic support at lesion site can impede OPC differentiation and remyelination.

To test this hypothesis, wild-type control rats were sacrificed and spinal cords were processed for fluorescent co-immunohistochemistry (FIG. 14). Sections were co-stained for SEMA4D (second panel from left), astrocyte marker GFAP (third panel from left) and DAPI to visualize cellular nuclei (right panel). Composite images are shown in the left-most panels and the dotted box depicts a 1.67× magnified inset below. Slides were imaged at 60× magnification using an EXi-Aqua-14 bit camera coupled to an Olympus Ix50 microscope.

As shown in FIG. 14, SEMA4D-expressing OPC are oriented in close proximity with GFAP+ astrocyte processes. Given the role that astrocytes play in facilitation of OPC survival and function, the juxtaposition of SEMA4D-expressing OPCs and SEMA4D receptor-expressing astrocytes suggests that disease-related activation of astrocytes with associated upregulation of plexin-B receptors and SEMA4D signaling can affect OPC function.

Role of Astrocytes in Neuronal Support.

In CNS disease, astrocytic activation leads to upregulation of Plexin expression, increased SEMA4D signaling and process retraction, which results in a loss of neuronal axon guidance, decreased trophic support, and/or dysregulated glutamate uptake/release. Ultimately, depending upon severity of disease stimulus, synapse loss and subsequent excitotoxic neuronal death can occur.

Figure 15:
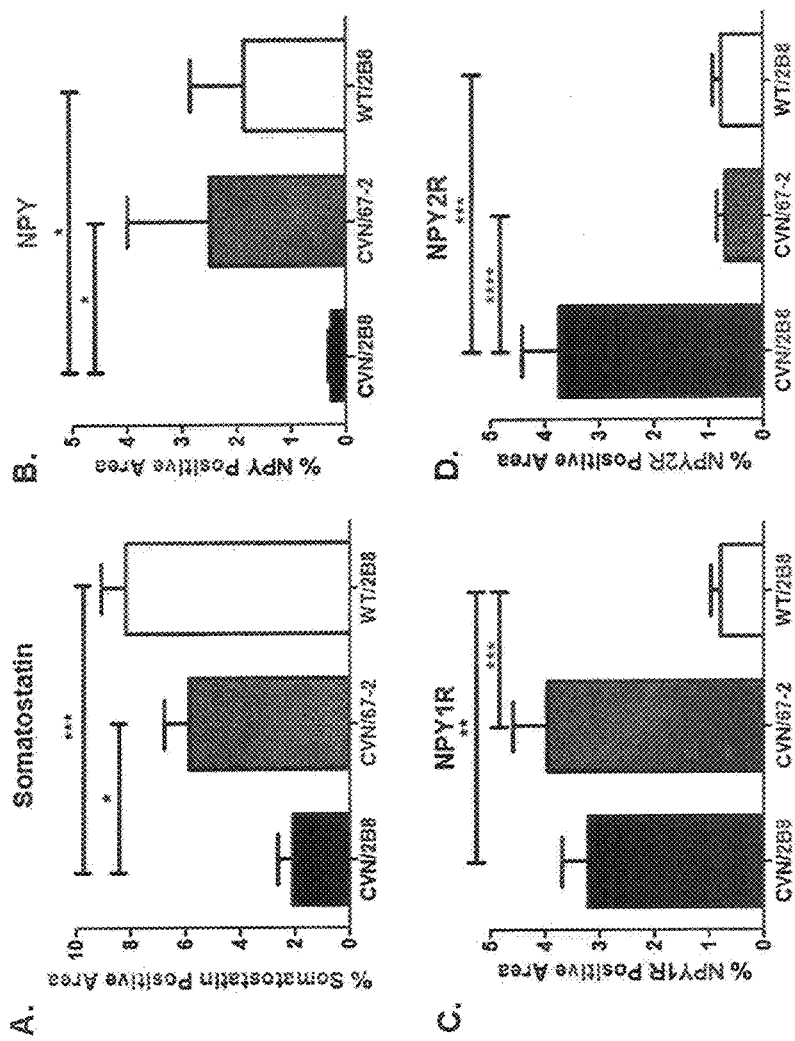

To determine if blocking SEMA4D signaling in CVN AD mice would impact synaptic marker expression in brain regions affected early in AD pathogenesis, 26 week-old CVN and wild-type control mice were injected weekly with 30 mg/kg anti-SEMA4D monoclonal antibody (67-2) or control IgG (2B8) intravenously for 13 weeks. At 41 weeks of age, mice were sacrificed and brain tissue sections from MAb-treated mice were stained with anti-somatostatin antibody, anti-Neuropeptide-Y (NPY), anti-NPY receptor 1 (NPY1R), or anti-NPY receptor 2 (NPY2R) to detect specific subsets of inhibitory neurons that degenerate in early AD. Percentages of somatostatin-positive signal were quantified within the subiculum, and NPY-, NPY1R-, or NPY2R-positive signal were quantified within the dentate gyrus for all animals and normalized, respectively, to total subiculum or dentate gyrus area scanned. The results are shown in FIG. 15 A, FIG. 15B, FIG. 15C, and FIG. 15D.

FIGS. 15A-15D show that anti-SEMA4D antibody treatment of CVN AD mice leads to a restoration in somatostatin (FIG. 15A), NPY (FIG. 15B), and NPY2R (FIG. 15D) staining intensity levels to levels characteristic of wild-type mice. Interestingly, agonists of NPY1R are reported to reduce stress and anxiety, while antagonists specific for NPY2R reduce stress and anxiety (Markus Heilig. The NPY system in stress, anxiety and depression. Neuropeptides 38 (2004) 213-224). As shown in FIG. 2A and FIG. 2B above, CVN mice treated with anti-SEMA4D exhibited reduced severity in anxiety in open field tests, findings that correlated with normalized (lower) NPY2R levels, while NPY1R levels were unchanged by anti-SEMA4D MAb treatment and remained higher than wild-type mice (FIG. 15C). Hence, these changes in NPY receptor levels are concordant with reduced anxiety behaviors observed in anti-SEMA4D treated CVN mice, a finding that further supports a role for SEMA4D in modulation of neurotransmission in vivo. It is noteworthy that downregulation of the inhibitory NPY neurotransmitter seen in the CVN AD model has also been reported in cerebral cortex of patients with Alzheimer's disease (Beal, et al., *Ann. Neurol.* 20, 282-288 (1986)).

Role of Astrocytes in Maintaining Blood-Brain Barrier Integrity.

As discussed elsewhere herein, astrocytic processes proximal to cerebral microvessels or pia are characterized by a high density of the water channel, aquaporin 4 (Aqp4).

Astrocytic processes facing synaptic regions are enriched in glutamate transporters, where the density of Aqp4 is comparatively low. CNS disease-induced astrocyte activation increases SEMA4D signaling through Plexin, which leads to a retraction of astrocytic foot processes as evidenced by redistribution of aquaporin-4. This results in dysregulation and permeability of the BBB, thereby facilitating endothelial inflammation and subsequent leukocyte entry into the CNS. In the setting of AD, Aqp4 staining intensities significantly decrease in regions with significant amyloid plaque burden.

To measure aquaporin-4 expression patterns in CVN AD mice as compared to age-matched wild-type mice, CVN and wild-type control mice were sacrificed at 41 weeks of age and processed for fluorescent co-immunohistochemistry. The results are shown in FIG. 16, with wild-type mice in the top panels and CVN mice in the lower panels. Sections were co-stained for aquaporin-4 (second panels from left), astrocyte marker GFAP (third panels from left) and DAPI (right panels) to visualize cellular nuclei. Composite images are shown in the left-most panels. Slides were imaged at 60× magnification using an EXi-Aqua-14 bit camera coupled to an Olympus Ix50 microscope.

As shown in FIG. 16, Aqp4 staining in age-matched CVN mice revealed a significant shift towards a diffuse pattern. This is in contrast to co-immunohistochemical analyses of Aqp4 and GFAP-positive astrocytes within the brains of wild-type mice, which demonstrate Aqp4 staining pattern in the subiculum that is restricted to areas proximal to microvasculature. This alteration in Aqp4 distribution, or loss in polarity, correlates with high astrocyte activation, as evidenced by increased intensity in GFAP staining. Given the strong co-registration in plexin-B1 staining in activated astrocytes (FIG. 11A and FIG. 11B) and the role of SEMA4D/plexin-B1 signaling in cellular process retraction, these data suggest that SEMA4D signaling can play a role in the alteration of astrocyte polarity at the BBB interface during disease.

To analyze the impact of SEMA4D on BBB, a dynamic in vitro blood-brain barrier (DIV-BBB) model was employed. Briefly, the model consists of hollow polypropylene fibers that contain transcapillary 2 to 4-μm diameter pores. The fibers were connected to a pulsatile pump that facilitates continuous flow of media, and experimental compounds through the fibers and normal stimulation of endothelial flow receptors. Human brain endothelial cells were inoculated into the luminal compartment and allowed to adhere to and coat the inside walls of the fibers, while human astrocytes were seeded into the abluminal compartment bathing the outside surface of the fibers. The endothelial cells and astrocytes interact across the membrane to induce formation of a barrier with tight junctions between endothelial cells. The integrity of this barrier can be monitored continuously by measurement of trans-endothelial electrical resistance (TEER). Human brain endothelial cells were inoculated into the luminal compartment and allowed to adhere to the polypropylene fibers, and human astrocytes were seeded separately on the abluminal surface of the fibers. At peak TEER (approximately 14 days in vitro), 0.5, 5, and 50 μg/ml recombinant SEMA4D was added successively at 12-h intervals. At 36 h after initial SEMA4D exposure, 250 μg/ml control IgG (MAb 2955; 1 DIV-BBB unit) or anti-SEMA4D (VX15/2503; 2 DIV-BBB units) was added and TEER measured for another 132 h. The results are shown in FIG. 17. Error bars represent standard deviation. The data shown are representative of three independent experiments, with each demonstrating similar effects of SEMA4D and antibody on DIV-BBB integrity.

As shown in FIG. 17, the breakdown of BBB was reversed within 24 h by the addition of anti-SEMA4D antibody (VX15/2503). Introduction of a control recombinant protein did not result in a decrease in TEER (data not shown). Moreover, introduction of control IgG antibody (MAb 2955) did not affect SEMA4D-induced BBB compromise.

These data suggest that CNS disease-induced astrocyte activation increases SEMA4D signaling through plexin-B1 and/or plexin-B2 upregulation, which leads to a retraction of astrocytic foot processes as evidenced by redistribution of aquaporin-4. This results in dysregulation and permeability of the BBB, thereby facilitating endothelial inflammation and subsequent leukocyte entry into the CNS.

Role of SEMA4D Signaling in Promoting Astrocyte Activation.

Given the association of SEMA4D receptor expression and the astrocyte activation marker GFAP, there exists the possibility that SEMA4D signaling can potentiate astrocyte activation, thereby providing a "feed-forward" mechanism during disease states. To examine the effects of SEMA4D on astrocyte activation, primary cultures of rat astrocytes were generated and treated with SEMA4D in isolation or in combination with thioacetamide (TAA) pretreatment, a well known hepatotoxic and hepatocarcinogenic agent that has been shown to induce plexin-B1 expression in vivo (Lim, J. S., et al., (2006). Mol. Cell. Tox., 2(2), 126-133). Rat primary astrocytes were pretreated for 4 h with TAA followed by soluble SEMA4D for 24 h. Cells were then fixed and stained for GFAP and scanned at 20× magnification. Error bars represent standard deviation. "*"=p<0.05 by 1-way ANOVA with Bonferroni's Multiple Comparison Test.

As shown in FIG. 18A, a significant enhancement in GFAP, an activation marker for astrocytes, was observed upon addition of SEMA4D to cells pretreated with TAA, suggesting that SEMA4D signaling enhances astrocyte activation.

In a second set of in vitro studies, primary rat astrocytes were cultured and treated with or without prostaglandin D2, a known activation factor produced by microglia in the CNS, followed by an 8 or 24-h exposure to recombinant SEMA4D protein. Cells were fixed, processed for phalloidin (F-actin) and DNAse (G-actin) histochemistry, and F-actin/G-actin area ratios were calculated for each treatment condition. Error bars represent standard deviation. "**"=p<0.01 by 2-way ANOVA with Bonferroni's Multiple Comparison Test.

As shown in FIG. 18B, PGD2-activated astrocytes exposed to recombinant SEMA4D undergo a globular to filamentous transition in their actin cytoskeleton that is indicative of SEMA4D/Plexin-mediated signaling and a heightened astrocyte activation state.

Many modifications and other embodiments of the disclosures set forth herein will come to mind to one skilled in the art to which these disclosures pertain having the benefit of the teachings presented in the foregoing descriptions and the associated drawings. Therefore, it is to be understood that the disclosures are not to be limited to the specific embodiments disclosed and that modifications and other embodiments are intended to be included within the scope of the appended claims and list of embodiments disclosed herein. Although specific terms are employed herein, they are used in a generic and descriptive sense only and not for purposes of limitation.

What is claimed is:

1. A method of treating a subject having a having, determined to have, or suspected of having a neuroinflammatory or neurodegenerative disorder, comprising administering to the subject an effective amount of an isolated antibody or antigen-binding fragment thereof that specifically binds to SEMA4D, wherein the antibody or antigen-binding fragment thereof comprises a variable heavy chain (VH) comprising VHCDRs 1-3 comprising SEQ ID NOs 6, 7, and 8, respectively, and a variable light chain (VL) comprising VLCDRs 1-3 comprising SEQ ID NOs 14, 15, and 16, respectively, and wherein the binding to SEMA4D acts to alleviate symptoms associated with the disorder.

2. The method of claim 1, wherein the binding molecule modulates astrocyte-mediated activity of oligodendrocyte-myelin function.

3. The method of claim 1, wherein the binding molecule modulates astrocyte-mediated synaptic activity, thereby preventing neural cell death.

4. The method of claim 1, wherein the binding molecule modulates astrocyte-mediated maintenance of the integrity of the blood-brain barrier.

5. The method of claim 1, wherein the VH and VL comprise, respectively, SEQ ID NO: 9 and SEQ ID NO: 17 or SEQ ID NO: 10 and SEQ ID NO: 18.

6. The method of claim 1, wherein the neurodegenerative disorder is selected from a group consisting of Alzheimer's disease, Parkinson's disease, Huntington's disease, Down syndrome, ataxia, amyotrophic lateral sclerosis (ALS), frontotemporal dementia (FTD), HIV-related cognitive impairment, CNS Lupus, mild cognitive impairment, or a combination thereof.

7. The method of claim 1, wherein the antibody or fragment thereof is administered to the subject in combination with at least one or more other treatments for neuroinflammatory or neurodegenerative disorders, and wherein the other treatment is administered prior to, during, or subsequent to administering the antibody or fragment thereof to the subject.

8. The method of claim 1, wherein the subject is human.

9. A method of protecting inhibitory neurons from degeneration in early Alzheimer's disease, comprising administering to a subject having, determined to have, or suspected of having early Alzheimer's disease an effective amount of an isolated antibody or antigen-binding fragment thereof that specifically binds to SEMA4D, wherein the antibody or antigen-binding fragment thereof comprises a variable heavy chain (VH) comprising VHCDRs 1-3 comprising SEQ ID NOs 6, 7, and 8, respectively, and a variable light chain (VL) comprising VLCDRs 1-3 comprising SEQ ID NOs 14, 15, and 16, respectively, and wherein the antibody or antigen-binding fragment thereof restores the number of somatostatin positive neurons, NYP-positive neurons, or both in the subject.

10. The method of claim 9, wherein the VH and VL comprise, respectively, SEQ ID NO: 9 and SEQ ID NO: 17 or SEQ ID NO: 10 and SEQ ID NO: 18.

11. The method of claim 9, wherein the antibody or fragment thereof modulates astrocyte-mediated synaptic activity.

12. The method of claim 9, wherein the antibody or fragment thereof modulates astrocyte-mediated maintenance of the integrity of the blood-brain barrier.

13. The method of claim 9, wherein administration of the antibody or fragment thereof to the subject reduces the rate of neuronal cell death in the subject.

14. The method of claim 9, wherein the antibody or fragment thereof is administered to the subject in combination with at least one or more other treatments for neuroinflammatory or neurodegenerative disorders, and wherein the other treatment is administered prior to, during, or subsequent to administering the antibody or fragment thereof to the subject.

15. The method of claim 9, wherein the subject is human.

* * * * *

SEQUENCE LISTING

<160> NUMBER OF SEQ ID NOS: 40

<210> SEQ ID NO 1
<211> LENGTH: 862
<212> TYPE: PRT
<213> ORGANISM: Homo sapiens

<400> SEQUENCE: 1

```
Met Arg Met Cys Thr Pro Ile Arg Gly Leu Leu Met Ala Leu Ala Val
1               5                   10                  15

Met Phe Gly Thr Ala Met Ala Phe Ala Pro Ile Pro Arg Ile Thr Trp
            20                  25                  30

Glu His Arg Glu Val His Leu Val Gln Phe His Glu Pro Asp Ile Tyr
        35                  40                  45

Asn Tyr Ser Ala Leu Leu Leu Ser Glu Asp Lys Asp Thr Leu Tyr Ile
    50                  55                  60

Gly Ala Arg Glu Ala Val Phe Ala Val Asn Ala Leu Asn Ile Ser Glu
65                  70                  75                  80

Lys Gln His Glu Val Tyr Trp Lys Val Ser Glu Asp Lys Lys Ala Lys
                85                  90                  95

Cys Ala Glu Lys Gly Lys Ser Lys Gln Thr Glu Cys Leu Asn Tyr Ile
            100                 105                 110

Arg Val Leu Gln Pro Leu Ser Ala Thr Ser Leu Tyr Val Cys Gly Thr
        115                 120                 125

Asn Ala Phe Gln Pro Ala Cys Asp His Leu Asn Leu Thr Ser Phe Lys
    130                 135                 140

Phe Leu Gly Lys Asn Glu Asp Gly Lys Gly Arg Cys Pro Phe Asp Pro
145                 150                 155                 160

Ala His Ser Tyr Thr Ser Val Met Val Asp Gly Glu Leu Tyr Ser Gly
                165                 170                 175

Thr Ser Tyr Asn Phe Leu Gly Ser Glu Pro Ile Ile Ser Arg Asn Ser
            180                 185                 190

Ser His Ser Pro Leu Arg Thr Glu Tyr Ala Ile Pro Trp Leu Asn Glu
        195                 200                 205

Pro Ser Phe Val Phe Ala Asp Val Ile Arg Lys Ser Pro Asp Ser Pro
    210                 215                 220

Asp Gly Glu Asp Asp Arg Val Tyr Phe Phe Phe Thr Glu Val Ser Val
225                 230                 235                 240

Glu Tyr Glu Phe Val Phe Arg Val Leu Ile Pro Arg Ile Ala Arg Val
                245                 250                 255

Cys Lys Gly Asp Gln Gly Gly Leu Arg Thr Leu Gln Lys Lys Trp Thr
            260                 265                 270

Ser Phe Leu Lys Ala Arg Leu Ile Cys Ser Arg Pro Asp Ser Gly Leu
        275                 280                 285

Val Phe Asn Val Leu Arg Asp Val Phe Val Leu Arg Ser Pro Gly Leu
    290                 295                 300

Lys Val Pro Val Phe Tyr Ala Leu Phe Thr Pro Gln Leu Asn Asn Val
305                 310                 315                 320

Gly Leu Ser Ala Val Cys Ala Tyr Asn Leu Ser Thr Ala Glu Glu Val
                325                 330                 335

Phe Ser His Gly Lys Tyr Met Gln Ser Thr Thr Val Glu Gln Ser His
            340                 345                 350

Thr Lys Trp Val Arg Tyr Asn Gly Pro Val Pro Lys Pro Arg Pro Gly
        355                 360                 365
```

```
Ala Cys Ile Asp Ser Glu Ala Arg Ala Ala Asn Tyr Thr Ser Ser Leu
    370                 375                 380

Asn Leu Pro Asp Lys Thr Leu Gln Phe Val Lys Asp His Pro Leu Met
385                 390                 395                 400

Asp Asp Ser Val Thr Pro Ile Asp Asn Arg Pro Arg Leu Ile Lys Lys
                405                 410                 415

Asp Val Asn Tyr Thr Gln Ile Val Val Asp Arg Thr Gln Ala Leu Asp
            420                 425                 430

Gly Thr Val Tyr Asp Val Met Phe Val Ser Thr Asp Arg Gly Ala Leu
        435                 440                 445

His Lys Ala Ile Ser Leu Glu His Ala Val His Ile Ile Glu Glu Thr
450                 455                 460

Gln Leu Phe Gln Asp Phe Glu Pro Val Gln Thr Leu Leu Ser Ser
465                 470                 475                 480

Lys Lys Gly Asn Arg Phe Val Tyr Ala Gly Ser Asn Ser Gly Val Val
                485                 490                 495

Gln Ala Pro Leu Ala Phe Cys Gly Lys His Gly Thr Cys Glu Asp Cys
            500                 505                 510

Val Leu Ala Arg Asp Pro Tyr Cys Ala Trp Ser Pro Thr Ala Thr
        515                 520                 525

Cys Val Ala Leu His Gln Thr Glu Ser Pro Ser Arg Gly Leu Ile Gln
530                 535                 540

Glu Met Ser Gly Asp Ala Ser Val Cys Pro Asp Lys Ser Lys Gly Ser
545                 550                 555                 560

Tyr Arg Gln His Phe Phe Lys His Gly Gly Thr Ala Glu Leu Lys Cys
                565                 570                 575

Ser Gln Lys Ser Asn Leu Ala Arg Val Phe Trp Lys Phe Gln Asn Gly
            580                 585                 590

Val Leu Lys Ala Glu Ser Pro Lys Tyr Gly Leu Met Gly Arg Lys Asn
        595                 600                 605

Leu Leu Ile Phe Asn Leu Ser Glu Gly Asp Ser Gly Val Tyr Gln Cys
        610                 615                 620

Leu Ser Glu Glu Arg Val Lys Asn Lys Thr Val Phe Gln Val Val Ala
625                 630                 635                 640

Lys His Val Leu Glu Val Lys Val Val Pro Lys Pro Val Val Ala Pro
                645                 650                 655

Thr Leu Ser Val Val Gln Thr Glu Gly Ser Arg Ile Ala Thr Lys Val
                660                 665                 670

Leu Val Ala Ser Thr Gln Gly Ser Ser Pro Pro Thr Pro Ala Val Gln
        675                 680                 685

Ala Thr Ser Ser Gly Ala Ile Thr Leu Pro Pro Lys Pro Ala Pro Thr
        690                 695                 700

Gly Thr Ser Cys Glu Pro Lys Ile Val Ile Asn Thr Val Pro Gln Leu
705                 710                 715                 720

His Ser Glu Lys Thr Met Tyr Leu Lys Ser Ser Asp Asn Arg Leu Leu
                725                 730                 735

Met Ser Leu Phe Leu Phe Phe Phe Val Leu Phe Leu Cys Leu Phe Phe
                740                 745                 750

Tyr Asn Cys Tyr Lys Gly Tyr Leu Pro Arg Gln Cys Leu Lys Phe Arg
            755                 760                 765

Ser Ala Leu Leu Ile Gly Lys Lys Pro Lys Ser Asp Phe Cys Asp
770                 775                 780

Arg Glu Gln Ser Leu Lys Glu Thr Leu Val Glu Pro Gly Ser Phe Ser
```

```
                    785                 790                 795                 800
        Gln Gln Asn Gly Glu His Pro Lys Pro Ala Leu Asp Thr Gly Tyr Glu
                        805                 810                 815

Thr Glu Gln Asp Thr Ile Thr Ser Lys Val Pro Thr Asp Arg Glu Asp
                        820                 825                 830

Ser Gln Arg Ile Asp Asp Leu Ser Ala Arg Asp Lys Pro Phe Asp Val
                        835                 840                 845

Lys Cys Glu Leu Lys Phe Ala Asp Ser Asp Ala Asp Gly Asp
                        850                 855                 860

<210> SEQ ID NO 2
<211> LENGTH: 861
<212> TYPE: PRT
<213> ORGANISM: Murine sp.

<400> SEQUENCE: 2

Met Arg Met Cys Ala Pro Val Arg Gly Leu Phe Leu Ala Leu Val Val
1               5                   10                  15

Val Leu Arg Thr Ala Val Ala Phe Ala Pro Val Pro Arg Leu Thr Trp
                20                  25                  30

Glu His Gly Glu Val Gly Leu Val Gln Phe His Lys Pro Gly Ile Phe
            35                  40                  45

Asn Tyr Ser Ala Leu Leu Met Ser Glu Asp Lys Asp Thr Leu Tyr Val
    50                  55                  60

Gly Ala Arg Glu Ala Val Phe Ala Val Asn Ala Leu Asn Ile Ser Glu
65                  70                  75                  80

Lys Gln His Glu Val Tyr Trp Lys Val Ser Asp Lys Lys Ser Lys
                85                  90                  95

Cys Ala Glu Lys Gly Lys Ser Lys Gln Thr Glu Cys Leu Asn Tyr Ile
            100                 105                 110

Arg Val Leu Gln Pro Leu Ser Ser Thr Ser Leu Tyr Val Cys Gly Thr
        115                 120                 125

Asn Ala Phe Gln Pro Thr Cys Asp His Leu Asn Leu Thr Ser Phe Lys
    130                 135                 140

Phe Leu Gly Lys Ser Glu Asp Gly Lys Gly Arg Cys Pro Phe Asp Pro
145                 150                 155                 160

Ala His Ser Tyr Thr Ser Val Met Val Gly Gly Glu Leu Tyr Ser Gly
                165                 170                 175

Thr Ser Tyr Asn Phe Leu Gly Ser Glu Pro Ile Ile Ser Arg Asn Ser
            180                 185                 190

Ser His Ser Pro Leu Arg Thr Glu Tyr Ala Ile Pro Trp Leu Asn Glu
        195                 200                 205

Pro Ser Phe Val Phe Ala Asp Val Ile Gln Lys Ser Pro Asp Gly Pro
    210                 215                 220

Glu Gly Glu Asp Asp Lys Val Tyr Phe Phe Thr Glu Val Ser Val
225                 230                 235                 240

Glu Tyr Glu Phe Val Phe Lys Leu Met Ile Pro Arg Val Ala Arg Val
                245                 250                 255

Cys Lys Gly Asp Gln Gly Gly Leu Arg Thr Leu Gln Lys Lys Trp Thr
            260                 265                 270

Ser Phe Leu Lys Ala Arg Leu Ile Cys Ser Lys Pro Asp Ser Gly Leu
        275                 280                 285

Val Phe Asn Ile Leu Gln Asp Val Phe Val Leu Arg Ala Pro Gly Leu
    290                 295                 300
```

-continued

Lys Glu Pro Val Phe Tyr Ala Val Phe Thr Pro Gln Leu Asn Asn Val
305                 310                 315                 320

Gly Leu Ser Ala Val Cys Ala Tyr Thr Leu Ala Thr Val Glu Ala Val
            325                 330                 335

Phe Ser Arg Gly Lys Tyr Met Gln Ser Ala Thr Val Glu Gln Ser His
            340                 345                 350

Thr Lys Trp Val Arg Tyr Asn Gly Pro Val Pro Thr Pro Arg Pro Gly
            355                 360                 365

Ala Cys Ile Asp Ser Glu Ala Arg Ala Asn Tyr Thr Ser Ser Leu
370                 375                 380

Asn Leu Pro Asp Lys Thr Leu Gln Phe Val Lys Asp His Pro Leu Met
385                 390                 395                 400

Asp Asp Ser Val Thr Pro Ile Asp Asn Arg Pro Lys Leu Ile Lys Lys
                405                 410                 415

Asp Val Asn Tyr Thr Gln Ile Val Val Asp Arg Thr Gln Ala Leu Asp
                420                 425                 430

Gly Thr Phe Tyr Asp Val Met Phe Ile Ser Thr Asp Arg Gly Ala Leu
            435                 440                 445

His Lys Ala Val Ile Leu Thr Lys Glu Val His Val Ile Glu Glu Thr
            450                 455                 460

Gln Leu Phe Arg Asp Ser Glu Pro Val Leu Thr Leu Leu Ser Ser
465                 470                 475                 480

Lys Lys Gly Arg Lys Phe Val Tyr Ala Gly Ser Asn Ser Gly Val Val
                485                 490                 495

Gln Ala Pro Leu Ala Phe Cys Glu Lys His Gly Ser Cys Glu Asp Cys
            500                 505                 510

Val Leu Ala Arg Asp Pro Tyr Cys Ala Trp Ser Pro Ala Ile Lys Ala
            515                 520                 525

Cys Val Thr Leu His Gln Glu Glu Ala Ser Ser Arg Gly Trp Ile Gln
            530                 535                 540

Asp Met Ser Gly Asp Thr Ser Ser Cys Leu Asp Lys Ser Lys Glu Ser
545                 550                 555                 560

Phe Asn Gln His Phe Lys His Gly Gly Thr Ala Glu Leu Lys Cys
            565                 570                 575

Phe Gln Lys Ser Asn Leu Ala Arg Val Val Trp Lys Phe Gln Asn Gly
            580                 585                 590

Glu Leu Lys Ala Ala Ser Pro Lys Tyr Gly Phe Val Gly Arg Lys His
            595                 600                 605

Leu Leu Ile Phe Asn Leu Ser Asp Gly Asp Ser Gly Val Tyr Gln Cys
            610                 615                 620

Leu Ser Glu Glu Arg Val Arg Asn Lys Thr Val Ser Gln Leu Leu Ala
625                 630                 635                 640

Lys His Val Leu Glu Val Lys Met Val Pro Arg Thr Pro Ser Pro
            645                 650                 655

Thr Ser Glu Asp Ala Gln Thr Glu Gly Ser Lys Ile Thr Ser Lys Met
            660                 665                 670

Pro Val Ala Ser Thr Gln Gly Ser Ser Pro Pro Thr Pro Ala Leu Trp
            675                 680                 685

Ala Thr Ser Pro Arg Ala Ala Thr Leu Pro Pro Lys Ser Ser Ser Gly
            690                 695                 700

Thr Ser Cys Glu Pro Lys Met Val Ile Asn Thr Val Pro Gln Leu His
705                 710                 715                 720

Ser Glu Lys Thr Val Tyr Leu Lys Ser Ser Asp Asn Arg Leu Leu Met

```
                725                 730                 735
Ser Leu Leu Leu Phe Ile Phe Val Phe Leu Cys Leu Phe Ser Tyr
        740                 745                 750

Asn Cys Tyr Lys Gly Tyr Leu Pro Gly Gln Cys Leu Lys Phe Arg Ser
        755                 760                 765

Ala Leu Leu Leu Gly Lys Lys Thr Pro Lys Ser Asp Phe Ser Asp Leu
        770                 775                 780

Glu Gln Ser Val Lys Glu Thr Leu Val Glu Pro Gly Ser Phe Ser Gln
785                 790                 795                 800

Gln Asn Gly Asp His Pro Lys Pro Ala Leu Asp Thr Gly Tyr Glu Thr
                805                 810                 815

Glu Gln Asp Thr Ile Thr Ser Lys Val Pro Thr Asp Arg Glu Asp Ser
                820                 825                 830

Gln Arg Ile Asp Glu Leu Ser Ala Arg Asp Lys Pro Phe Asp Val Lys
                835                 840                 845

Cys Glu Leu Lys Phe Ala Asp Ser Asp Ala Asp Gly Asp
        850                 855                 860

<210> SEQ ID NO 3
<211> LENGTH: 30
<212> TYPE: DNA
<213> ORGANISM: Artificial
<220> FEATURE:
<223> OTHER INFORMATION: Polynucleotide anti-CD100 VH CDR1

<400> SEQUENCE: 3
ggctacagct tcagcgacta ctacatgcac                                    30

<210> SEQ ID NO 4
<211> LENGTH: 51
<212> TYPE: DNA
<213> ORGANISM: Artificial
<220> FEATURE:
<223> OTHER INFORMATION: Polynucleotide anti-CD100 VH CDR2

<400> SEQUENCE: 4
cagattaatc ctaccactgg cggcgctagc tacaaccaga agttcaaggg c            51

<210> SEQ ID NO 5
<211> LENGTH: 27
<212> TYPE: DNA
<213> ORGANISM: Artificial
<220> FEATURE:
<223> OTHER INFORMATION: Polynucleotide anti-CD100 VH CDR3

<400> SEQUENCE: 5
tattactacg gcagacactt cgatgtc                                       27

<210> SEQ ID NO 6
<211> LENGTH: 10
<212> TYPE: PRT
<213> ORGANISM: Artificial
<220> FEATURE:
<223> OTHER INFORMATION: Polypeptide anti-CD100 VH CDR1

<400> SEQUENCE: 6

Gly Tyr Ser Phe Ser Asp Tyr Tyr Met His
1               5                   10

<210> SEQ ID NO 7
<211> LENGTH: 17
<212> TYPE: PRT
```

```
<213> ORGANISM: Artificial
<220> FEATURE:
<223> OTHER INFORMATION: Polypeptide anti-CD100 VH CDR2

<400> SEQUENCE: 7

Gln Ile Asn Pro Thr Thr Gly Gly Ala Ser Tyr Asn Gln Lys Phe Lys
1               5                   10                  15

Gly

<210> SEQ ID NO 8
<211> LENGTH: 9
<212> TYPE: PRT
<213> ORGANISM: Artificial
<220> FEATURE:
<223> OTHER INFORMATION: Polypeptide anti-CD100 VH CDR3

<400> SEQUENCE: 8

Tyr Tyr Tyr Gly Arg His Phe Asp Val
1               5

<210> SEQ ID NO 9
<211> LENGTH: 118
<212> TYPE: PRT
<213> ORGANISM: Artificial
<220> FEATURE:
<223> OTHER INFORMATION: Polypeptide anti-CD100 VH 2503

<400> SEQUENCE: 9

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ser Phe Ser Asp Tyr
            20                  25                  30

Tyr Met His Trp Val Arg Gln Ala Pro Gly Gln Gly Leu Glu Trp Met
        35                  40                  45

Gly Gln Ile Asn Pro Thr Thr Gly Gly Ala Ser Tyr Asn Gln Lys Phe
    50                  55                  60

Lys Gly Lys Ala Thr Ile Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Tyr Tyr Tyr Gly Arg His Phe Asp Val Trp Gly Gln Gly Thr
            100                 105                 110

Thr Val Thr Val Ser Ser
        115

<210> SEQ ID NO 10
<211> LENGTH: 118
<212> TYPE: PRT
<213> ORGANISM: Artificial
<220> FEATURE:
<223> OTHER INFORMATION: Polypeptide anti-CD100 VH 67

<400> SEQUENCE: 10

Gln Val Gln Leu Gln Gln Ser Gly Pro Glu Leu Val Lys Pro Gly Ala
1               5                   10                  15

Ser Val Lys Ile Ser Cys Lys Ala Ser Gly Tyr Ser Phe Ser Asp Tyr
            20                  25                  30

Tyr Met His Trp Val Lys Gln Ser Pro Glu Asn Ser Leu Glu Trp Ile
        35                  40                  45

Gly Gln Ile Asn Pro Thr Thr Gly Gly Ala Ser Tyr Asn Gln Lys Phe
    50                  55                  60
```

Lys Gly Lys Ala Thr Leu Thr Val Asp Lys Ser Ser Thr Ala Tyr
65                  70                  75                  80

Met Gln Leu Lys Ser Leu Thr Ser Glu Glu Ser Ala Val Tyr Tyr Cys
                85                  90                  95

Thr Arg Tyr Tyr Tyr Gly Arg His Phe Asp Val Trp Gly Gln Gly Thr
            100                 105                 110

Thr Val Thr Val Ser Ser
        115

<210> SEQ ID NO 11
<211> LENGTH: 45
<212> TYPE: DNA
<213> ORGANISM: Artificial
<220> FEATURE:
<223> OTHER INFORMATION: Polynucleotide anti-CD100 VL CDR1

<400> SEQUENCE: 11
aaggccagcc aaagcgtgga ttatgatggc gatagctata tgaac         45

<210> SEQ ID NO 12
<211> LENGTH: 21
<212> TYPE: DNA
<213> ORGANISM: Artificial
<220> FEATURE:
<223> OTHER INFORMATION: Polynucleotide anti-CD100 VL CDR2

<400> SEQUENCE: 12
gctgcatcca atctggaaag c         21

<210> SEQ ID NO 13
<211> LENGTH: 27
<212> TYPE: DNA
<213> ORGANISM: Artificial
<220> FEATURE:
<223> OTHER INFORMATION: Polynucleotide anti-CD100 VL CDR3

<400> SEQUENCE: 13
cagcaaagca atgaggatcc ctacacc         27

<210> SEQ ID NO 14
<211> LENGTH: 15
<212> TYPE: PRT
<213> ORGANISM: Artificial
<220> FEATURE:
<223> OTHER INFORMATION: Polypeptide anti-CD100 VL CDR1

<400> SEQUENCE: 14

Lys Ala Ser Gln Ser Val Asp Tyr Asp Gly Asp Ser Tyr Met Asn
1               5                   10                  15

<210> SEQ ID NO 15
<211> LENGTH: 7
<212> TYPE: PRT
<213> ORGANISM: Artificial
<220> FEATURE:
<223> OTHER INFORMATION: Polypeptide anti-CD100 VL CDR2

<400> SEQUENCE: 15

Ala Ala Ser Asn Leu Glu Ser
1               5

<210> SEQ ID NO 16
<211> LENGTH: 9
<212> TYPE: PRT

```
<213> ORGANISM: Artificial
<220> FEATURE:
<223> OTHER INFORMATION: Polypeptide anti-CD100 VL CDR3

<400> SEQUENCE: 16

Gln Gln Ser Asn Glu Asp Pro Tyr Thr
1               5

<210> SEQ ID NO 17
<211> LENGTH: 111
<212> TYPE: PRT
<213> ORGANISM: Artificial
<220> FEATURE:
<223> OTHER INFORMATION: Polypeptide anti-CD100 VL 2503

<400> SEQUENCE: 17

Asp Ile Val Met Thr Gln Ser Pro Asp Ser Leu Ala Val Ser Leu Gly
1               5                   10                  15

Glu Arg Ala Thr Ile Asn Cys Lys Ala Ser Gln Ser Val Asp Tyr Asp
                20                  25                  30

Gly Asp Ser Tyr Met Asn Trp Tyr Gln Gln Lys Pro Gly Gln Pro Pro
            35                  40                  45

Lys Leu Leu Ile Tyr Ala Ala Ser Asn Leu Glu Ser Gly Val Pro Asp
50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Ser Asn
                85                  90                  95

Glu Asp Pro Tyr Thr Phe Gly Gln Gly Thr Lys Leu Glu Ile Lys
            100                 105                 110

<210> SEQ ID NO 18
<211> LENGTH: 111
<212> TYPE: PRT
<213> ORGANISM: Artificial
<220> FEATURE:
<223> OTHER INFORMATION: Polypeptide anti-CD100 VL 67

<400> SEQUENCE: 18

Asp Ile Val Met Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
                20                  25                  30

Gly Asp Ser Tyr Met Asn Trp Tyr Gln Gln Lys Pro Gly Gln Pro Pro
            35                  40                  45

Lys Leu Leu Ile Tyr Ala Ala Ser Asn Leu Glu Ser Gly Ile Pro Ala
50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln Gln Ser Asn
                85                  90                  95

Glu Asp Pro Tyr Thr Phe Gly Gly Gly Thr Lys Leu Glu Ile Lys
            100                 105                 110

<210> SEQ ID NO 19
<211> LENGTH: 354
<212> TYPE: DNA
<213> ORGANISM: Artificial
<220> FEATURE:
<223> OTHER INFORMATION: Polynucleotide anti-CD100 VH 2503
```

<400> SEQUENCE: 19

```
caggtgcagc tggtgcagag cggcgctgag gtgaagaagc ctggcagcag cgtgaaggtc      60
tcctgcaagg ctagcggcta cagcttcagc gactactaca tgcactgggt gagacaggcc     120
cctggccaag gcctggagtg gatgggccag attaatccta ccactggcgg cgctagctac     180
aaccagaagt tcaagggcaa ggccaccatt accgtggaca aaagcaccag cacagcctac     240
atggagctga gcagcctgag aagcgaggac accgccgtgt attactgtgc cagatattac     300
tacggcagac acttcgatgt ctggggccaa ggcaccacgg tcaccgtctc ttca           354
```

<210> SEQ ID NO 20
<211> LENGTH: 354
<212> TYPE: DNA
<213> ORGANISM: Artificial
<220> FEATURE:
<223> OTHER INFORMATION: Polynucleotide anti-CD100 VH 67

<400> SEQUENCE: 20

```
caggtccagc tgcagcagtc tggacctgag ctggtgaagc ctggggcttc agtgaagata      60
tcctgcaagg cttctggtta ctcattcagt gactactaca tgcactgggt gaagcaaagt     120
cctgaaaata gtcttgagtg gattggacag attaatccta ccactggggg tgctagctac     180
aaccagaagt tcaagggcaa ggccacatta actgtagata atcctccag cacagcctac      240
atgcagctca gagcctgac atctgaagag tctgcagtct attactgtac aagatattac      300
tacggtagac acttcgatgt ctggggccaa gggaccacgg tcaccgtttc ctca           354
```

<210> SEQ ID NO 21
<211> LENGTH: 333
<212> TYPE: DNA
<213> ORGANISM: Artificial
<220> FEATURE:
<223> OTHER INFORMATION: Polynucleotide anti-CD100 VL 2503

<400> SEQUENCE: 21

```
gacatcgtga tgacccagag cccagacagc ctggctgtga gcctgggcga gagggccacc      60
atcaactgca aggccagcca aagcgtggat tatgatggcg atagctatat gaactggtac     120
cagcagaaac caggccagcc tcctaagctg ctgatttacg ctgcatccaa tctggaaagc     180
ggcgtgcctg acagattcag cggcagcggc agcggcacag atttcactct gaccatcagc     240
agcctgcagg ctgaagatgt ggcagtgtat tactgtcagc aaagcaatga ggatccctac     300
accttcggcc aagggaccaa gctcgagatc aaa                                  333
```

<210> SEQ ID NO 22
<211> LENGTH: 333
<212> TYPE: DNA
<213> ORGANISM: Artificial
<220> FEATURE:
<223> OTHER INFORMATION: Polynucleotide anti-CD100 VL 67

<400> SEQUENCE: 22

```
gacattgtga tgacccagtc tccagcttct ttggctgtgt ctctagggca gagggccacc      60
atctcctgca aggccagcca aagtgttgat tatgatggtg atagttatat gaactggtac     120
caacagaaac caggacagcc acccaaactc ctcatctatg ctgcatccaa tctagaatct     180
gggatcccag ccaggtttag tggcagtggg tctgggacag acttcaccct caacatccat     240
cctgtggagg aggaggatgc tgcaacctat tactgtcagc aaagtaatga ggatccgtac     300
acgttcggag gggggaccaa gctcgagatc aaa                                  333
```

<210> SEQ ID NO 23
<211> LENGTH: 118
<212> TYPE: PRT
<213> ORGANISM: Artificial
<220> FEATURE:
<223> OTHER INFORMATION: Polypeptide anti-CD100 VH 76

<400> SEQUENCE: 23

Gln Val Gln Leu Gln Gln Ser Gly Ala Glu Leu Ala Lys Pro Gly Ala
1               5                   10                  15

Ser Val Lys Met Ser Cys Lys Ala Ser Gly Tyr Thr Phe Thr Arg Tyr
            20                  25                  30

Trp Met His Trp Val Lys Gln Arg Pro Gly Gln Gly Leu Glu Trp Ile
        35                  40                  45

Gly Tyr Ile Asn Pro Ser Thr Gly Tyr Ser Asp Tyr Asn Gln Lys Phe
    50                  55                  60

Lys Asp Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Asp Pro Tyr Gly Trp Thr Met Asp Ser Trp Gly Gln Gly Thr
            100                 105                 110

Leu Val Thr Val Ser Ser
        115

<210> SEQ ID NO 24
<211> LENGTH: 10
<212> TYPE: PRT
<213> ORGANISM: Artificial
<220> FEATURE:
<223> OTHER INFORMATION: Polypeptide anti-CD100 VH 76 CDR1

<400> SEQUENCE: 24

Gly Tyr Thr Phe Thr Arg Tyr Trp Met His
1               5                   10

<210> SEQ ID NO 25
<211> LENGTH: 17
<212> TYPE: PRT
<213> ORGANISM: Artificial
<220> FEATURE:
<223> OTHER INFORMATION: Polypeptide anti-CD100 VH 76 CDR2

<400> SEQUENCE: 25

Tyr Ile Asn Pro Ser Thr Gly Tyr Ser Asp Tyr Asn Gln Lys Phe Lys
1               5                   10                  15

Asp

<210> SEQ ID NO 26
<211> LENGTH: 9
<212> TYPE: PRT
<213> ORGANISM: Artificial
<220> FEATURE:
<223> OTHER INFORMATION: Polypeptide anti-CD100 VH 76 CDR3

<400> SEQUENCE: 26

Asp Pro Tyr Gly Trp Thr Met Asp Ser
1               5

<210> SEQ ID NO 27
<211> LENGTH: 107

<212> TYPE: PRT
<213> ORGANISM: Artificial
<220> FEATURE:
<223> OTHER INFORMATION: Polypeptide anti-CD100 VL 76

<400> SEQUENCE: 27

Asp Ile Gln Met Thr Gln Ser Pro Ser Ser Leu Ser Ala Ser Leu Gly
1               5                   10                  15
Asp Thr Ile Thr Ile Thr Cys His Ala Ser Gln Asn Ile Asn Val Trp
            20                  25                  30
Leu Ser Trp Tyr Gln Gln Lys Pro Gly Asn Ile Pro Lys Leu Leu Ile
        35                  40                  45
Tyr Lys Ala Ser Asn Leu His Thr Gly Val Pro Ser Arg Phe Ser Gly
50                  55                  60
Ser Gly Ser Gly Thr Gly Phe Thr Leu Thr Ile Ser Ser Leu Gln Pro
65                  70                  75                  80
Glu Asp Ile Ala Thr Tyr Tyr Cys Gln Gln Gly Gln Ser Tyr Pro Tyr
                85                  90                  95
Thr Phe Gly Gly Gly Thr Lys Leu Glu Ile Lys
            100                 105

<210> SEQ ID NO 28
<211> LENGTH: 11
<212> TYPE: PRT
<213> ORGANISM: Artificial
<220> FEATURE:
<223> OTHER INFORMATION: Polypeptide anti-CD100 VL 76 CDR1

<400> SEQUENCE: 28

His Ala Ser Gln Asn Ile Asn Val Trp Leu Ser
1               5                   10

<210> SEQ ID NO 29
<211> LENGTH: 7
<212> TYPE: PRT
<213> ORGANISM: Artificial
<220> FEATURE:
<223> OTHER INFORMATION: Polypeptide anti-CD100 VL 76 CDR2

<400> SEQUENCE: 29

Lys Ala Ser Asn Leu His Thr
1               5

<210> SEQ ID NO 30
<211> LENGTH: 9
<212> TYPE: PRT
<213> ORGANISM: Artificial
<220> FEATURE:
<223> OTHER INFORMATION: Polypeptide anti-CD100 VL 76 CDR3

<400> SEQUENCE: 30

Gln Gln Gly Gln Ser Tyr Pro Tyr Thr
1               5

<210> SEQ ID NO 31
<211> LENGTH: 354
<212> TYPE: DNA
<213> ORGANISM: Artificial
<220> FEATURE:
<223> OTHER INFORMATION: Polynucleotide anti-CD100 VH 76

<400> SEQUENCE: 31
caggtccagc tgcagcagtc tgggggctgaa ctggcaaaac ctggggcctc agtgaagatg    60

```
tcctgcaagg cttctggcta cacctttact aggtactgga tgcactgggt aaaacagagg    120
cctggacagg gtctggaatg gattggatac attaatccta gcactggtta ttctgattac    180
aatcagaagt tcaaggacaa ggccacattg actgcagaca atcctccag cacagcctac    240 atgcaactga gcagcctgac atctgaggac tctgcagtct attactgtgc aagagacccc    300
tacggctgga ctatggactc ctggggccaa gggactctgg tcaccgtctc ctca          354
```

<210> SEQ ID NO 32
<211> LENGTH: 30
<212> TYPE: DNA
<213> ORGANISM: Artificial
<220> FEATURE:
<223> OTHER INFORMATION: Polynucleotide anti-CD100 VH 76 CDR1

<400> SEQUENCE: 32

```
ggctacacct ttactaggta ctggatgcac                                      30
```

<210> SEQ ID NO 33
<211> LENGTH: 51
<212> TYPE: DNA
<213> ORGANISM: Artificial
<220> FEATURE:
<223> OTHER INFORMATION: Polynucleotide anti-CD100 VH 76 CDR2

<400> SEQUENCE: 33

```
tacattaatc ctagcactgg ttattctgat tacaatcaga agttcaagga c              51
```

<210> SEQ ID NO 34
<211> LENGTH: 27
<212> TYPE: DNA
<213> ORGANISM: Artificial
<220> FEATURE:
<223> OTHER INFORMATION: Polynucleotide anti-CD100 VH 76 CDR3

<400> SEQUENCE: 34

```
gacccctacg gctggactat ggactcc                                         27
```

<210> SEQ ID NO 35
<211> LENGTH: 321
<212> TYPE: DNA
<213> ORGANISM: Artificial
<220> FEATURE:
<223> OTHER INFORMATION: Polynucleotide anti-CD100 VL 76

<400> SEQUENCE: 35

```
gacatccaga tgacccagtc tccatccagt ctgtctgcat cccttggaga cacaattacc    60
atcacttgcc atgccagtca gaacattaat gtttggttaa gctggtacca gcagaaacca   120
ggaaatattc ctaaactatt gatctataag cttccaact tgcacacagg cgtcccatca    180
aggtttagtg gcagtggatc tggaacaggt ttcacattaa ccatcagcag cctgcagcct   240
gaagacattg ccacttacta ctgtcaacag ggtcaaagtt atccgtacac gttcggaggg   300
gggaccaagc tcgagatcaa a                                              321
```

<210> SEQ ID NO 36
<211> LENGTH: 33
<212> TYPE: DNA
<213> ORGANISM: Artificial
<220> FEATURE:
<223> OTHER INFORMATION: Polynucleotide anti-CD100 VL 76 CDR1

<400> SEQUENCE: 36

```
catgccagtc agaacattaa tgtttggtta agc                                  33
```

<210> SEQ ID NO 37
<211> LENGTH: 21
<212> TYPE: DNA
<213> ORGANISM: Artificial
<220> FEATURE:
<223> OTHER INFORMATION: Polynucleotide anti-CD100 VL 76 CDR2

<400> SEQUENCE: 37
aaggcttcca acttgcacac a                                              21

<210> SEQ ID NO 38
<211> LENGTH: 27
<212> TYPE: DNA
<213> ORGANISM: Artificial
<220> FEATURE:
<223> OTHER INFORMATION: Polynucleotide anti-CD100 VL 76 CDR3

<400> SEQUENCE: 38
caacagggtc aaagttatcc gtacacg                                        27

<210> SEQ ID NO 39
<211> LENGTH: 113
<212> TYPE: PRT
<213> ORGANISM: Artificial sequence
<220> FEATURE:
<223> OTHER INFORMATION: 2282 VL domain

<400> SEQUENCE: 39

Asp Ile Val Met Thr Gln Ser Pro Leu Ser Leu Pro Val Ser Pro Gly
1               5                   10                  15

Glu Pro Ala Thr Ile Asn Cys Lys Ser Ser Gln Ser Leu Phe Asn Ser
            20                  25                  30

Gly Asn Gln Lys Asn Tyr Leu Ala Trp Tyr Leu Gln Lys Pro Gly Gln
        35                  40                  45

Pro Pro Lys Leu Leu Ile Tyr Gly Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Asp His Thr Tyr Pro Tyr Thr Phe Gly Gln Gly Thr Lys Leu Glu Ile
            100                 105                 110

Lys

<210> SEQ ID NO 40
<211> LENGTH: 122
<212> TYPE: PRT
<213> ORGANISM: Artificial sequence
<220> FEATURE:
<223> OTHER INFORMATION: 2282 VH domain

<400> SEQUENCE: 40

Gln Val Gln Leu Val Gln Ser Gly Ala Glu Val Lys Lys Pro Gly Ser
1               5                   10                  15

Ser Val Lys Val Ser Cys Thr Ala Ser Gly Tyr Thr Phe Thr Asp Tyr
            20                  25                  30

Tyr Met Asp Trp Val Arg Gln Ala Pro Gly Gln Gly Leu Glu Trp Met
        35                  40                  45

Gly Arg Val Asn Pro Tyr His Gly Tyr Ala Thr Tyr Asn Gln Lys Phe
    50                  55                  60

```
Lys Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Glu Glu Asn Ser Tyr Asp Gly Tyr Tyr Gly Met Asp Tyr Trp
             100                 105                 110

Gly Gln Gly Thr Leu Val Thr Val Ser Ser
        115                 120
```